United States Patent [19]

Alt et al.

[11] Patent Number: 5,821,370
[45] Date of Patent: Oct. 13, 1998

[54] HETEROCYCLIC COMPOUNDS AND THEIR PREPARATION AND USE

[75] Inventors: Charles A. Alt, Greenwood; Leander Merritt; Gary A. Rhodes, both of Indianapolis; Roger L. Robey; Eldon E. Van Meter, both of Greenwood; John S. Ward, Indianapolis, all of Ind.

[73] Assignee: Eli Lilly and Company, Indianapolis, Ind.

[21] Appl. No.: 470,787

[22] Filed: Jun. 6, 1995

Related U.S. Application Data

[60] Division of Ser. No. 443,673, Jun. 1, 1995, abandoned, which is a continuation-in-part of Ser. No. 327,766, Oct. 24, 1994, abandoned.

[51] Int. Cl.⁶ .................................................. C07D 285/10
[52] U.S. Cl. ............................................................ 548/135
[58] Field of Search ............................................. 548/135

[56] References Cited

U.S. PATENT DOCUMENTS

| | | |
|---|---|---|
| 3,247,193 | 4/1966 | Liaz . |
| 3,729,477 | 4/1973 | Wasson . |
| 4,837,241 | 6/1989 | Sauerberg et al. . |
| 5,041,455 | 8/1991 | Sauerberg et al. . |
| 5,043,345 | 8/1991 | Sauerberg et al. . |
| 5,260,314 | 11/1993 | Sauerberg et al. . |
| 5,328,923 | 7/1994 | Sauerberg et al. . |
| 5,328,924 | 7/1994 | Sauerberg et al. . |

FOREIGN PATENT DOCUMENTS

| | | |
|---|---|---|
| 733 390 | 11/1969 | Belgium . |
| 733387 | 11/1969 | Belgium . |
| 733388 | 11/1969 | Belgium . |
| 733390 | 11/1969 | Belgium . |
| 8 004 967 | 8/1980 | Belgium . |
| 8 004 967 | 9/1980 | Belgium . |
| 9 201 236 | 7/1992 | Belgium . |
| 9 201 237 | 7/1992 | Belgium . |
| 0 081 782-A | 6/1983 | European Pat. Off. . |
| 0 306 148 B1 | 8/1988 | European Pat. Off. . |
| 0 307 142 A1 | 3/1989 | European Pat. Off. . |
| 0 414 511 A1 | 8/1990 | European Pat. Off. . |
| 0 456 519 A1 | 5/1991 | European Pat. Off. . |
| 0 621 272 A1 | 4/1994 | European Pat. Off. . |
| 0 604 353-A | 6/1994 | European Pat. Off. . |
| 19 14 496-B | 9/1970 | Germany . |
| 49 13176 | 2/1974 | Japan . |
| 4 182403 | 6/1992 | Japan . |
| 484 934-A | 1/1970 | Switzerland . |
| 1 161093-A1 | 8/1969 | United Kingdom . |
| 1 174 178 | 12/1969 | United Kingdom . |
| 1 190 359 | 5/1970 | United Kingdom . |
| 1 319 403 | 7/1971 | United Kingdom . |
| 2 258 652 | 8/1991 | United Kingdom . |
| WO 84/02525 A1 | 7/1984 | WIPO . |
| WO 92/03430 | 3/1992 | WIPO . |
| WO 94/20496 | 3/1992 | WIPO . |
| WO 93/20814 A1 | 10/1993 | WIPO . |
| WO 94/18201 A1 | 8/1994 | WIPO . |
| WO 94/27996 | 8/1994 | WIPO . |
| WO 94/20495 | 9/1994 | WIPO . |
| WO 95/05174-A1 | 2/1995 | WIPO . |
| WO 95/05379-A1 | 2/1995 | WIPO . |

OTHER PUBLICATIONS

Derwent Abstracts 95–067278/09 Jan. 26, 1995.
Leonard M. Weinstock, et al., *J. Org. Chem.*, 32, 2823–2829, (1967).
Shuntaro Mataka, et al., *Heterocyclec*, 20:10, 2047–2050, (1983).
Shuntaro Mataka, et al., *Heterocycles*, 20:7, 1285–1290, (1983).
Chemical Abstracts, 70, 57854 (1964).
Chemical Abstracts, 116, 59363 (1992).
Chemical Abstracts, 118, 240003, 240004, and 240005 (1993).
Mathew, et al., *Am. J. Psychiatry.*, 137:9, 1118–1120, (1980).
Sim, M. and Houghton, H., *J. of Nervous and Mental Disease*, 143:6, 484–491, (1966).
Rapaport, et al., *Biol. Psychiatry*, 29, 658–664, (1991).
Derwent Abstracts 95–067278/09 Jan. 26, 1995.
Leonard M. Weinstock, et al., *J. Org. Chem.*, 32, 2823–2829, (1967).
Shuntaro Mataka, et al., *Heterocyclec*, 20:10, 2047–2050, (1983).
Shuntaro Mataka, et al., *Heterocycles*, 20:7, 1285–1290, (1983).
Shuntaro Mataka, et al., *Heterocycles*, 20:7, 1285–1290.

*Primary Examiner*—Robert Gerstl
*Attorney, Agent, or Firm*—Arleen Palmberg; MaCarri R. Vorndran-Jones; David E. Boone

[57] ABSTRACT

The present invention relates to therapeutically active azacyclic or azabicyclic compounds, a method of preparing the same and to pharmaceutical compositions comprising the compounds. The novel compounds are useful in treating diseases in the central nervous system caused by malfunctioning of the muscarinic cholinergic system.

2 Claims, No Drawings

HETEROCYCLIC COMPOUNDS AND THEIR PREPARATION AND USE

This application is a division of application Ser. No. 08/443,673, filed on Jun. 1, 1995, which is a continuation in part of application Ser. No. 08/327,766 filed Oct. 24, 1995, both abandoned.

FIELD OF THE INVENTION

The present invention relates to therapeutically active azacyclic or azabicyclic compounds, a method of preparing the same and to compositions for pharmaceutical or veterinary use comprising the compounds with a carrier. The novel compounds are useful as stimulants of the cognitive function of the forebrain and hippocampus of mammals and especially in the treatment of Alzheimer's disease.

BACKGROUND OF THE INVENTION

Due to the generally improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, an up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, the postsynaptic muscarinic receptors in the forebrain and hippocampus still exist. Therefore, muscarinic cholinergic agonists are useful in the treatment of Alzheimer's disease, in halting its progression, and in improving the cognitive functions of elderly people.

The compounds of this invention are also useful analgesic agents and therefore are useful in the treatment of severely painful conditions.

Furthermore, the compounds of this invention are useful in the treatment of glaucoma, psychosis, mania, bipolar disorder, schizophrenia or schizophreniform conditions, depression, sleeping disorders, epilepsy, cerebral ischemia, and gastrointestinal motility disorders.

SUMMARY OF THE INVENTION

It is an object of the invention to provide new muscarinic cholinergic compounds.

The novel compounds of the invention are heterocyclic compounds having the formula I'

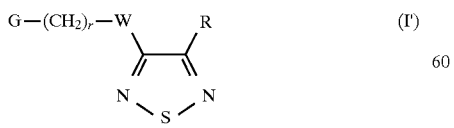

wherein

W is oxygen or sulphur;

R is hydrogen, amino, halogen, $NHR^6$, $NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl), $-Z-C_{3-10}$-cycloalkyl and $-Z-C_{4-12}$-(cycloalkylalkyl) wherein $R^4$ is $C_{1-15}$-alkyl, $C_{2-15}$-alkenyl, $C_{2-15}$-alkynyl, each of which is optionally substituted with one or more halogen(s), $-CF_3$, $-CN$, Y, phenyl or phenoxy wherein phenyl or phenoxy is optionally substituted with halogen, $-CN$, $C_{1-4}$-alkyl, $C_{1-4}$-alkoxy, $-OCF_3$, $-CF_3$, $-CONH_2$ or $-CSNH_2$; or R is phenyl or benzyloxycarbonyl, each of which is optionally substituted with halogen, $-CN$, $C_{1-4}$-alkyl, $C_{1-4}$-alkoxy, $-OCF_3$, $-CF_3$, $-CONH_2$ or $-CSNH_2$; or R is $-OR^5Y$, $-SR^5Y$, $OR^5-Z-Y$, $-SR^5ZY$, $-O-R^5-Z-R^4$ or $-S-R^5-Z-R^4$ wherein Z is oxygen or sulphur, $R^5$ is $C_{1-15}$-alkyl, $C_{2-15}$-alkenyl, $C_{2-15}$-alkynyl, and Y is a 5 or 6 membered heterocyclic group; and G is selected from one of the following azacyclic or azabicyclic ring systems:

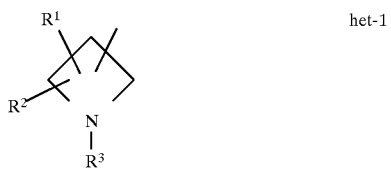

het-1

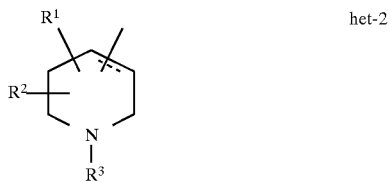

het-2

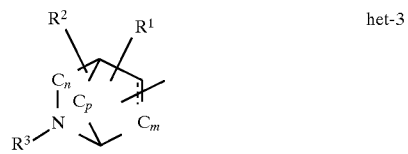

het-3

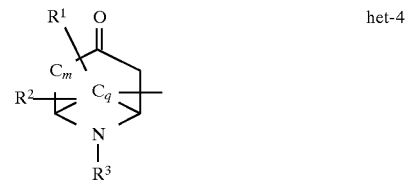

het-4

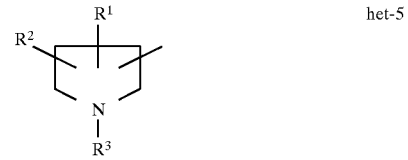

het-5

het-6

-continued

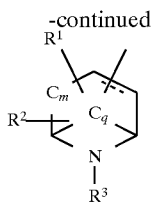

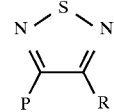

or G can optionally be substituted $C_3$–$C_8$ cycloalkyl or optionally substituted $C_{1-6}$-alkyl wherein the substitution is —$NR^6R^7$;

$R^6$ and $R^7$ independently are hydrogen, $C_{1-6}$-alkyl; or $R^6$ and $R^7$ together with the nitrogen atom optionally form a 4- to 6-member ring;

$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with —OH, —$COR^{6'}$, $CH_2$—OH, halogen, —$NH_2$, carboxy, or phenyl;

$R^3$ is hydrogen, $C_{1-5}$-alkyl, $C_{2-5}$-alkenyl or $C_{2-5}$-alkynyl;

n is 0, 1 or 2;

m is 0, 1 or 2;

p is 0, 1 or 2;

q is 1 or 2;

r is 0, 1 or 2;

......... is a single or double bond;

provided that when W is oxygen and G is alkyl, R is selected from the group consisting of hydrogen, amino, $NHR^6$, $NR^6R^7$, $R^4$, —$OR^4$, —$SR^4$, —$SOR^4$, —$SO_2R^4$, $C_{3-10}$-cycloalkyl, $C_{4-12}$-(cycloalkylalkyl), —Z—$C_{3-10}$-cycloalkyl and —Z—$C_{4-12}$-(cycloalkylalkyl), phenyl or benzyloxycarbonyl, each of which is optionally substituted with halogen, —CN, $C_{1-4}$-alkyl, $C_{1-4}$-alkoxy, —$OCF_3$, —$CF_3$, —$CONH_2$ or —$CSNH_2$; or R is —$OR^5Y$, —$SR^5Y$, $OR^5$—Z—Y, —$SR^5ZY$, —O—$R^5$—Z—$R^4$ or —S—$R^5$—Z—$R^4$ wherein Z is oxygen or sulphur, $R^5$ is $C_{1-15}$-alkyl, $C_{2-15}$-alkenyl, $C_{2-15}$-alkynyl; or a pharmaceutically acceptable salt or solvate thereof.

The invention also relates to methods of preparing the above mentioned compounds, comprising reacting a compound of formula III

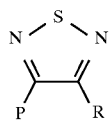

(III)

wherein P is $R^9SO_2$ or halogen; $R^9$ is $C_{1-8}$ alkyl or aryl; and

R has the meaning defined above; with G—$(CH_2)_r$—W—$h^+$ wherein $h^+$ is an alkoxide metal, G, W and r have the meanings defined above.

A further aspect of this invention provides novel compounds of formula IV and a process for preparing compounds of the formula IV

IV comprising reacting a compound of the formula III wherein P is Cl with $R^8N[(R^{10}R^{11}R^{12}Si) (R^{13}R^{14}R^{15}Si)]$ wherein R has the meaning defined supra. $R^8$ is Li, Na, or K; Si means silyl; $R^{10}$, $R^{11}$, $R^{12}$, $R^{13}$, $R^{14}$ and $R^{15'}$ are independently selected from the group consisting of ($C_1$–$C_6$)-alkyl, aryl, and aryl ($C_1$–$C_3$)alkyl; $R^{15}$ and $R^{16}$ are independently selected from the group consisting of hydrogen, $R^{10}R^{11}R^{12}Si$, and $R^{13}R^{14}R^{15'}Si$. R is selected from the group consisting of hydrogen, amino, halogen, $NHR^6$, $NR^6R^7$, $R^4$, —$OR^4$, —$SR^4$, —$SOR^4$, —$SO_2R^4$, $C_{3-10}$-cycloalkyl, $C_{4-12}$-(cycloalkylalkyl), —Z—$C_{3-10}$-cycloalkyl and —Z—$C_{4-12}$-(cycloalkylalkyl) wherein $R^4$ is $C_{1-15}$-alkyl, $C_{2-15}$-alkenyl, $C_{2-15}$-alkynyl, each of which is optionally substituted with one or more halogen(s), —$CF_3$, —CN, Y, phenyl or phenoxy wherein phenyl or phenoxy is optionally substituted with halogen, —CN, $C_{1-4}$-alkyl, $C_{1-4}$-alkoxy, —$OCF_3$, —$CF_3$, —$CONH_2$ or —$CSNH_2$; or R is phenyl or benzyloxycarbonyl, each of which is optionally substituted with halogen, —CN, $C_{1-4}$-alkyl, $C_{1-4}$-alkoxy, —$OCF_3$, —$CF_3$, —$CONH_2$ or —$CSNH_2$; or R is —$OR^5Y$, —$SR^5Y$, $OR^5$—Z—Y, —$SR^5ZY$, —O—$R^5$—Z—$R^4$ or —S—$R^5$—Z—$R^4$ wherein Z is oxygen or sulphur, $R^5$ is $C_{1-15}$-alkyl, $C_{2-15}$-alkenyl, $C_{2-15}$-alkynyl, and Y is a 5 or 6 membered heterocyclic group;

provided that when R is hydrogen, amine, or halogen, $R^{16}$ shall be selected from the group consisting of $(R^{10}R^{11}R^{12}Si)$ and $(R^{13}R^{14}R^{15'}Si)$ Finally, compounds of formula V are provided by the present invention;

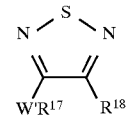

V wherein W' is selected from the group consisting of O, S and $SO_2$;

$R^{17}$ is selected from the group consisting of $C_1$–$C_6$ alkyl, aryl, $R^{19}$ substituted alkyl, and $R^{19}$ substituted aryl;

$R^{19}$ is selected from the group consisting of straight or branched $C_1$–$C_6$ alkyl, straight or branched $C_2$–$C_6$ alkenyl, halogen, halogen($C_1$–$C_6$)alkyl, halogen ($C_2$–$C_6$)alkenyl, $COR^{20}$, $C_2$–$C_{10}$ alkanoyl, $CO_2R^{20}$, ($C_1$–$C_6$ alkyl)$_2$ amino, $NO_2$, $SR^{20}$, $OR^{20}$, $C_3$–$C_8$ cycloalkyl, $C_3$–$C_8$ cycloalkyl-($C_1$–$C_3$)alkyl, $C_5$–$C_8$ cycloalkenyl, substituted $C_5$–$C_8$ cycloalkenyl, $C_5$–$C_8$ cycloalkenyl-($C_1$–$C_3$)alkyl, and $C_7$–$C_{16}$ arylalkyl; $R^{20}$ is independently selected from the group consisting of hydrogen, and $C_1$–$C_4$ alkyl; wherein the $R^{19}$ substituent may be attached at any available carbon atom;

$R^{18}$ is $R^4SO_2$, Cl, Br or I;

provided that when W' is O; and R is $C_1$–$C_5$ alkyl or aryl; then $R^{18}$ is selected from $R^4SO_2$, Br and I; or a pharmaceutically acceptable salt or solvate thereof.

It is to be understood that the invention extends to each of the stereoisomeric forms of the compounds of the present invention as well as the pure diastereomeric, pure enatiomeric, and racemic forms of the compounds of this invention.

The invention further relates to a process for preparing the intermediates of Formulas II

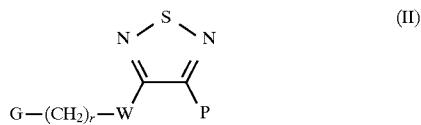 (II)

or III supra., comprising reacting $(CN)_2$ with $R^4$—S—H or $G(CH_2)_r$—W—H, wherein P, $R^4$, G, r, and W have the meaning defined above and which formed compound is subsequently reacted with $S_2Cl_2$ to form a compound of formula II or III.

As used herein the term "treating" includes prophylaxis of a physical and/or mental condition or amelioration or elimination of the developed physical and/or mental condition once it has been established or alleviation of the characteristic symptoms of such condition.

As used herein with reference to the G substituent, the —$(CH_2)_r$—W-thiadiazole moiety can be attached at any carbon atom of the azacyclic or azabicyclic ring. Further, $R^1$ and $R^2$ of the G substituent may be present at any position, including the point of attachment of the —$(CH_2)_r$—W-thiadiazole moiety.

As used herein with reference to the G substituent, the phrase "$R^6$ and $R^7$ together with the nitrogen atom optionally form a 4- to 6-member ring" means that $R^6$ and $R^7$ are each independently hydrogen, $C_1$–$C_6$ alkyl wherein the $R^6$ and $R^7$ groups may optionally join to form a 4- to 6-member ring including the nitrogen. For example, optionally joined groups include, but are not limited to:

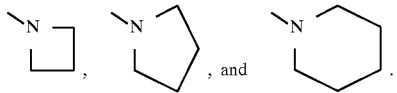

As used herein the phrase "interacting with a muscarinic cholinergic receptor" shall include compounds which block muscarinic cholinergic receptors or modulate such receptors. The phrase shall include the effect observed when compounds act as agonists, partial agonists and/or antagonists at a muscarinic cholinergic receptor.

As used herein, the term "alkoxide metal" means a metal suitable for alkoxide formation. Such alkoxide metals include, but are not limited to, $Li^+$, $K^+$, $Na^+$, $Cs^+$, and $Ca^{++}$. Especially preferred alkoxide metals include $Li^+$, $K^+$, and $Na^+$.

As used herein, the term "halogen" means Cl, Br, F, and I. Especially preferred halogens include Cl, Br, and I.

As used herein the phrase "one or more selected from" shall more preferredly refer to from 1–3 substituents. The term shall further preferredly refer to from 1–2 substituents.

The terms "$C_1$–$C_{n'}$ alkyl" wherein n can be from 2 through 15, as used herein, represent a branched or linear alkyl group having from one to the specified number of carbon atoms. Typical $C_1$–$C_6$ alkyl groups include, but are not limited to, methyl, ethyl, n-propyl, iso-propyl, butyl, iso-butyl, sec-butyl, tert-butyl, pentyl, hexyl and the like.

The terms "$C_2$–$C_{n'}$ alkenyl", wherein n' can be from 3 through 10, as used herein, represents an olefinically unsaturated branched or linear group having from 2 to the specified number of carbon atoms and at least one double bond. Examples of such groups include, but are not limited to, 1-propenyl, 2-propenyl (—$CH_2$—CH=$CH_2$), 1,3-butadienyl, (—CH=CHCH=$CH_2$), 1-butenyl (—CH=$CHCH_2CH_3$), hexenyl, pentenyl, and the like.

The term "$C_2$–$C_5$ alkynyl" refers to an unsaturated branched or linear group having from 2 to 5 carbon atoms and at least one triple bond. Examples of such groups include, but are not limited to, 1-propynyl, 2-propynyl, 1-butynyl, 2-butynyl, 1-pentynyl, and the like.

The terms "halogen($C_1$–$C_6$)alkyl" and "halogen($C_2$–$C_6$) alkenyl" refer to alkyl or alkenyl substituents having one or more independently selected halogen atoms attached at one or more available carbon atoms. These terms include, but are not limited to, chloromethyl, 1-bromoethyl, 2-bromoethyl, 1,1,1-trifluoroethyl, 1,1,2-trifluoroethyl, 1,2,2-trifluoroethyl, 2,2,2-trifluoroethyl, trifluoromethyl, trifluoroethylenyl, 3-bromopropyl, 3-bromo-1-propenyl, 2-bromopropyl, 2-bromo-1-propenyl, 3-chlorobutyl, 3-chloro-2-butenyl, 2,3-dichlorobutyl, 1-chloroethylenyl, 2-chloroethylenyl, 5-fluoro-3-pentenyl, 3-chloro-2-bromo-5-hexenyl, 3-chloro-2-bromobutyl, trichloromethyl, 1,1-dichloroethyl, 1,2-dichloroethyl, 2,2-dichloroethyl, 1,4-dichlorobutyl, 3-bromopentyl, 1,3-dichlorobutyl, 1,1-dichloropropyl, and the like.

The term "$C_2$–$C_{10}$ alkanoyl" represents a group of the formula C(O) ($C_1$–$C_9$) alkyl. Typical $C_2$–$C_{10}$ alkanoyl groups include acetyl, propanoyl, butanoyl, and the like.

The term "($C_1$–$C_6$ alkyl) amino" refers to a monoalkylamino group. Examples of such groups are methylamino, ethylamino, iso-propylamino, n-propylamino, (n-propyl) amino, (iso-propyl)amino, n-propylamino, t-butylamino, and the like.

The term "$C_3$–$C_n$ cycloalkyl" wherein n=4–8, represents cyclopropyl, cyclobutyl, cyclopentyl, cyclohexyl, cycloheptyl, and cyclooctyl.

The term "substituted($C_5$–$C_{n'}$) cycloalkyl" refers to a cycloalkyl group as described supra wherein the cycloalkyl group may be substituted with from one to four substituents independently selected from the group consisting of hydrogen, $C_1$–$C_6$ alkyl, $NO_2$, halogen, halogen($C_1$–$C_6$) alkyl, halogen($C_2$–$C_6$)alkenyl, $C_2$–$C_6$ alkenyl, $CO_2R^{20}$, ($C_1$–$C_6$ alkyl) amino, —$SR^{20}$, and $OR^{20}$; wherein $R^{20}$ is selected from the group consisting of $C_{1-15}$-alkyl, $C_{2-15}$-alkenyl, $C_{2-15}$-alkynyl.

The term "$C_3$–$C_8$ cycloalkyl-($C_1$–$C_3$)alkyl" represents an alkyl group substituted at a terminal carbon with a $C_3$–$C_8$ cycloalkyl group. Typical cycloalkylalkyl groups include cyclohexylethyl, cyclohexylmethyl, 3-cyclopentylpropyl, and the like.

The term "$C_5$–$C_8$ cycloalkenyl" represents an olefinically unsaturated ring having five to eight carbon atoms. Such groups include, but are not limited to, cyclohexyl-1,3-dienyl, cyclohexenyl, cyclopentenyl, cycloheptenyl, cyclooctenyl, cyclohexyl-1,4-dienyl, cycloheptyl-1,4-dienyl, cyclooctyl-1,3,5-trienyl and the like.

The term "substituted ($C_5$–$C_8$) cycloalkenyl" refers to a cycloalkenyl group as described supra. wherein the cycloalkenyl group may be substituted with from one to four substituents independently selected from the group consisting of hydrogen, $C_1$–$C_6$ alkyl, $NO_2$, halogen, halogen ($C_1$–$C_6$)alkyl, halogen($C_2$–$C_6$)alkenyl, $C_2$–$C_6$ alkenyl, $COR^{20}$, $C_2$–$C_{10}$ alkanoyl, $C_7$–$C_{16}$ arylalkyl, $CO_2R^{20}$, ($C_1$–$C_6$ alkyl) amino, —$SR^{20}$, and —$OR^{20}$; wherein $R^{20}$ is selected from the group consisting of $C_{1-15}$-alkyl, $C_{2-15}$-alkenyl, and $C_{2-15}$-alkynyl.

The term "$C_5$–$C_8$ cycloalkenyl-($C_1$–$C_3$)alkyl" represents a $C_1$–$C_3$ alkyl group substituted at a terminal carbon with a $C_5$–$C_8$ cycloalkenyl group.

As used herein, the phrase "5 or 6 membered heterocyclic group" means a group containing from one to four N, O or S atom(s) or a combination thereof, which heterocyclic group is optionally substituted at carbon or nitrogen atom(s) with $C_{1-6}$-alkyl, —$CF_3$, phenyl, benzyl or thienyl, or a carbon atom in the heterocyclic group together with an oxygen atom form a carbonyl group, or which heterocyclic group is optionally fused with a phenyl group. The phrase "5 or 6 membered heterocyclic group" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having 3-heteroatoms; 6-membered heterocycles with one heteroatom (e.g. pyridine, quinoline, isoquinoline, phenanthrine, 5,6-cycloheptenopyridine); 6-membered heterocycles with two heteroatoms (e.g. pyridazines, cinnolines, phthalazines, pyrazines, pyrimidines, quinazolines); 6-membered heterocycles with three heteroatoms (e.g. 1,3,5-triazine); and 6-member heterocycles with four heteroatoms. Particularly preferred are thiophenes, pyridines, and furans.

As used herein the term "carboxy" refers to a substituent having the common meaning understood by the skilled artisan, wherein the point of attachment may be through the carbon or oxygen atom of the group.

As used herein the term "aryl" means an organic radical derived from an aromatic hydrocarbon by the removal of one atom; e.g., phenyl or naphthyl. Most preferably, aryl refers to $C_6$–$C_{10}$ aryl, wherein the aryl ring system, including any alkyl substitutions, comprises from 6 to 10 carbon atoms; e.g., phenyl, 3,3-dimethylphenyl, naphthyl, and the like. The aryl radical may be substituted by one or two $C_1$–$C_6$ straight or branched alkyl. The term "aryl($C_1$–$C_3$) alkyl" refers to any aryl group which is attached to the parent moiety via the alkyl group.

As used herein the term "phosphorous(III) compound" has the art accepted meaning of the term. For example, the term includes, but is in no way limited to, triphenylphosphine, tri(p-toluyl) phosphine, tributyl phosphine, tri(p-dimethylaminiophenyl) phosphine, triethyl phosphine, and trimethyl phosphine. The artisan can choose other appropriate phosphorous(III) compounds using methods and literature references which are commonly available to the chemist artisan.

As used herein the term "diester of azodicarboxylate" has the art accepted meaning of the term. For example, the term includes, but is in no way limited to diethylazodicarboxylate, dimethylazodicarboxylate, diisopropylazodicarboxylate, and di-tertbutylazodicarboxylate. The skilled chemist can determine other appropriate diesters of azodicarboxylate using methods and literature readily available to the chemist artisan.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in *Journal of Pharmaceutical Science*, 66, 2 (1977) which are known to the skilled artisan. The compounds of this invention may form solvates with standard low molecular weight solvents using methods known to the skilled artisan.

The compounds of this invention can be prepared using the chemical processes illustrated in Scheme I. The starting materials for the illustrated process are commercially available or may be prepared using methods known to the skilled artisan.

Scheme I

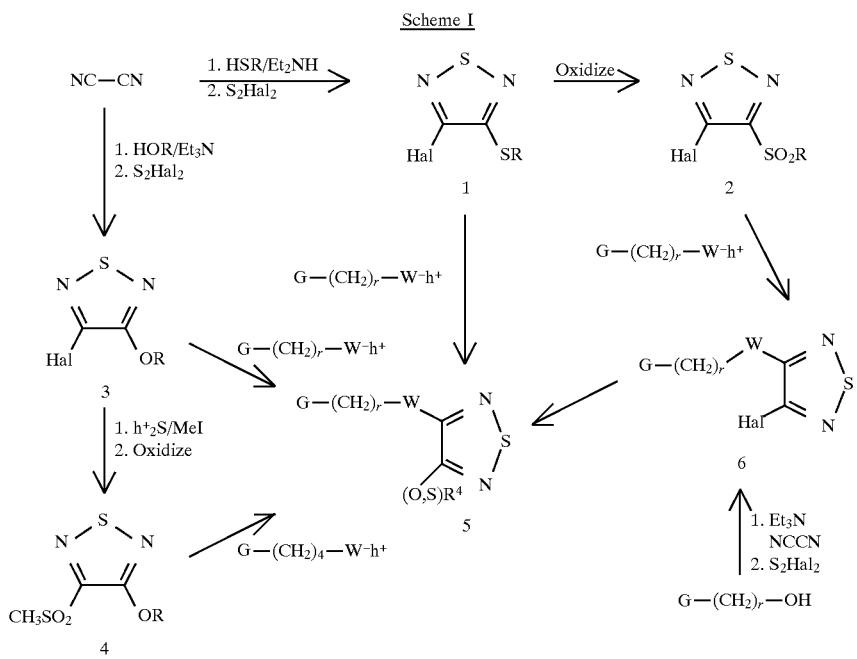

As used in Scheme I, R, $h^+$, and G are as defined supra. As used in Scheme I, the term "Hal" refers to Cl, Br, and $R^9SO_2$. Preferred oxidizing agents for the process of Scheme I include oxone and sodium periodate. Oxone is an especially preferred oxidizing agent for the process of Scheme I. compounds of Formula 3, as illustrated in Scheme I wherein the OR group is replaced by an $R^4$ group, can be prepared using methods well known in the art. See for example, U.S. Pat. No. 5,043,345.

Further, compounds of Formula I may be prepared using the process illustrated in the following Scheme II

Scheme II

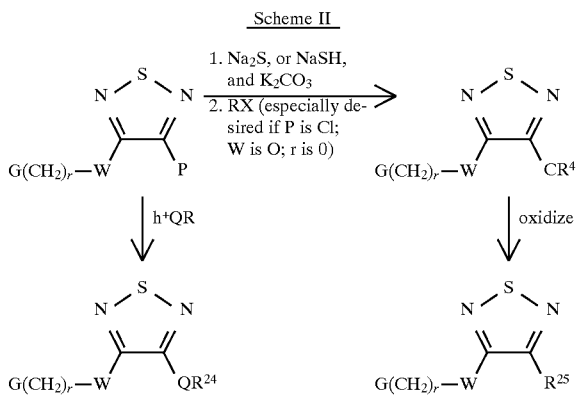

As used in Scheme II, Q may be N, O or S; $R^{24}$ is selected from the group consisting of hydrogen, $R^4$, $R^5$, $R^6$, and $R^7$; $R^{25}$ is selected from the group consisting of $SOR^4$ and $SO_2R^4$; all other meanings are as defined supra.

Additional compounds of Formula I may be prepared using the process illustrated by Scheme III.

Scheme III

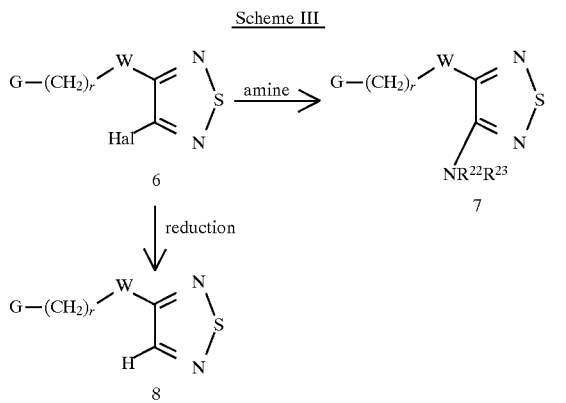

As used in Scheme III, Hal, W, r, and G are as defined supra. As used in Scheme III, $R^{22}$ and $R^{23}$ are independently selected from the group consisting of hydrogen, $R^6$ and $R^7$.

Certain intermediates of the present invention may be prepared using the process illustrated in Scheme IV.

Scheme IV

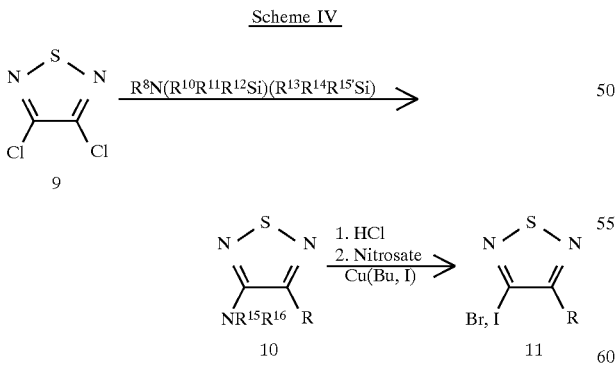

As used in Scheme IV, $R^8$, Si, $R^{10}$, $R^{11}$, $R^{12}$, $R^{13}$, $R^{14}$, $R^{15'}$, $R^{15}$ and $R^{16}$ are as defined supra. For example, $R^8N[(R^{10}R^{11}R^{12}Si)(R^{13}R^{14}R^{15'}Si)]$ may be, but is not limited to lithium bis(tri-2-propylsilyl)amide, sodium bis(trimethylsilyl)amide, potassium bis(trimethylsilyl)amide, lithium bis(tri-2-propylsilyl)amide, sodium bis (ethyldimethylsilyl)amide, potassium bis(1-propylethylmethylsilyl)amide, lithium bis(tri-phenylsilyl)amide, sodium bis(tri-phenylmethylsilyl)amide, potassium bis(2-butyl-2-propylmethylsilyl)amide, lithium (tri-2-propylsilyl)(2-butyldiethylsilyl)amide, sodium (trimethylsilyl)(triphenylsilyl)amide, potassium (dimethyl phenylsilyl)(ethyldimethylsilyl)amide, and the like. Most preferably, $R^{15}$ and $R^{16}$ are each hydrogen when the process of Scheme III is used for preparing a compound of 11 from a compound of 10. The intermediate 10 may be nitrosated using standard nitrosating procedures. A preferred nitrosating agent is isoamyl nitrite; however, other known nitrosating agents are appropriate. As used in Scheme III, the term "Cu(Br,I)" refers to copper (I) bromide, copper (II) bromide, or copper (I) iodide. The artisan will recognize that the copper (I) bromide, copper (II) bromide, or copper (I) iodide reagent shall determine the substitution on the product of the process illustrated in Scheme III.

Certain compounds of this invention may more preferably be prepared by a process using a hydroxyalkylamine (G—OH) wherein G has the meaning defined supra. in the presence of a phosphorus(III) compound and a diester of azodicarboxylate to give the 1,2,5-thiadiazoyloxyalkylamine as illustrated by Scheme V.

Scheme V

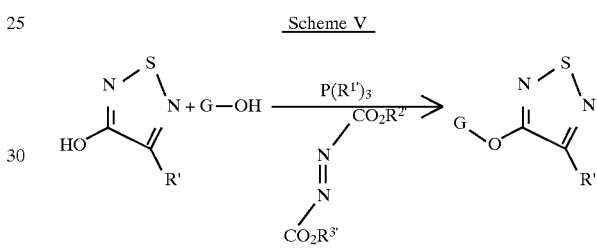

The G groups are as defined supra. The R' is selected from the group consisting of hydrogen, halogen, $NR^6R^7$, $R^4$, —$OR^4$, —$SR^4$, —$SOR^4$, —$SO_2R^4$, $C_{3-10}$-cycloalkyl, $C_{4-12}$-(cycloalkylalkyl), —Z—$C_{3-10}$-cycloalkyl and —Z—$C_{4-12}$-(cycloalkylalkyl);

$R^4$ is selected from the group consisting of $C_{1-15}$-alkyl, $C_{2-15}$-alkenyl, $C_{2-15}$-alkynyl, each of which is optionally substituted with one or more independently selected from the group consisting of halogen(s), —$CF_3$, —CN, Y, phenyl and phenoxy wherein phenyl or phenoxy is optionally substituted with one or more independently selected from the group consisting of halogen, —CN, $C_{1-4}$-alkyl, $C_{1-4}$-alkoxy, —$OCF_3$, or —$CF_3$; or R' is phenyl or benzyloxycarbonyl, each of which is optionally substituted with one or more independently selected from the group consisting of halogen, —CN, $C_{1-4}$-alkyl, $C_{1-4}$-alkoxy, —$OCF_3$, and —$CF_3$; or R' selected from the group consisting of —$OR^5Y$, —$SR^5Y$, $OR^5$—Z—Y, —$SR^5ZY$, —O—$R^5$—Z—$R^4$ and —S—$R^5$—Z—$R^4$;

Z is oxygen or sulphur;

$R^5$ is selected from the group consisting of $C_{1-15}$-alkyl, $C_{2-15}$-alkenyl, and $C_{2-15}$-alkynyl;

Y is a 5 or 6 membered heterocyclic group;

$R^{1'}$ is selected from the group consisting of phenyl, $C_{1-15}$-alkyl, $C_{2-5}$-alkenyl, $C_{2-5}$-alkynyl and $(NR^{2'})_3$;

$R^{2'}$ and $R^{3'}$ are independently selected from the group consisting of hydrogen, $C_{1-15}$-alkyl, $C_{2-5}$-alkenyl, $C_{2-5}$-alkynyl, and $C_{1-5}$-alkyl substituted with one or more selected from the group consisting of halogen and phenyl;

W is oxygen or sulphur;

$R^6$, and $R^7$ independently are $C_{1-6}$-alkyl; or $R^6$ and $R^7$ together with the nitrogen atom optionally form a 4- to 6-member ring;

$R^1$ and $R^2$ are independently selected from hydrogen, $C_{1-15}$-alkyl, $C_{2-5}$-alkenyl, $C_{2-5}$-alkynyl, $C_{1-10}$-alkoxy, and $C_{1-5}$-alkyl substituted with one or more independently selected from the group consisting of —$COR^{6'}$, halogen, and phenyl;

$R^{6'}$ is hydrogen or $C_1$-$C_3$ alkyl;

$R^3$ is selected from the group consisting of $C_{1-5}$-alkyl, $C_{2-5}$-alkenyl and $C_{2-5}$-alkynyl;

n is 0, 1 or 2;

m is 0, 1 or 2;

p is 0, 1 or 2;

q is 1 or 2;

r is 0, 1 or 2;

........ is a single or double bond.

Preferred $R^{1'}$ groups include phenyl, $C_{1-15}$-alkyl, and $(NR^{2'})_3$. The process of Scheme IV is particularly advantageous because the process provides a method for inverting the stereochemistry at the carbon bearing the hydroxyl group in G.

Another new process illustrated by Scheme VI, involves the sequential reaction of 3,4-dihydroxy-1,2,5-thiadiazole with G—OH wherein G is defined as defined supra. in the presence of a phosphorous(III) compounds and a diester of azodicarboxylate to give an unisolated hydroxy-1,2,5-thiadiazole ether I'' followed by reaction of I'' with $R^4OH$ where $R^4$ is defined as supra. with phosphorous(III) compounds and a diester of azodicarboxylate to give the diethers of 3,4-dihydroxy-1,2,5-thiadiazole which are useful as muscarinic agonists and antagonists. (See, *Org. Prep. & Procedures* 1969, 1, 255–258) The substituents illustrated in Scheme VI are as defined supra.

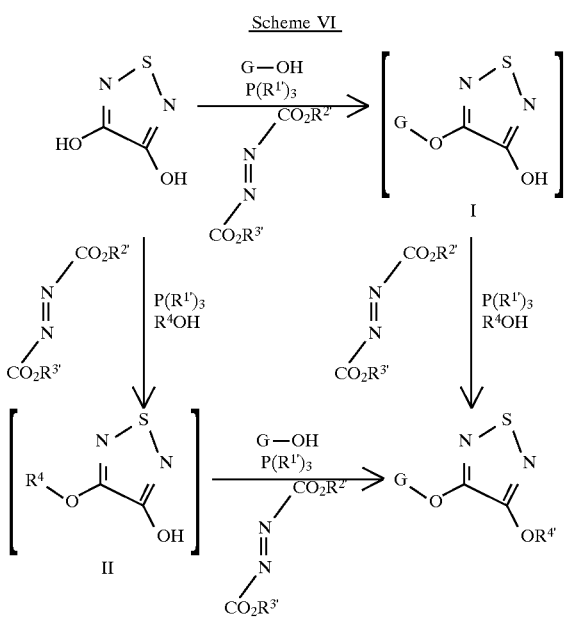

Alternatively, the order of addition of the alcohols may be reversed as shown above to give unisolated hydroxy-1,2,5-thiadiazole ether II which is subsequently converted to the same final muscarinic active compound.

The process illustrated by Scheme VII encompasses the reaction of a phenol or hydroxyheteroaryl compound with compound III in the presence of a phosphorus(III) compound and a diester of azodicarboxylate to give compound IV.

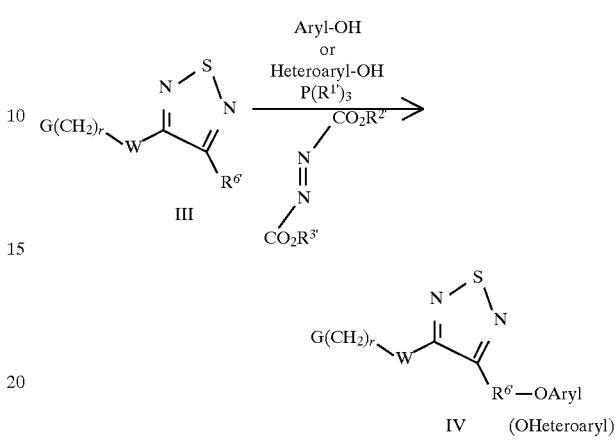

In compound III, $G(CH_2)_rW$ is as defined supra. and $R^{6'}$ is selected from the group consisting of $R^7$, —$OR^7$, —$SR^7$, —$SOR^7$, —$SO_2R^7$, $C_{3-10}$-cycloalkyl, $C_{4-12}$-(cycloalkylalkyl), —Z—$C_{3-10}$-cycloalkyl and —Z—$C_{4-12}$-(cycloalkylalkyl);

$R^7$ is $C_{1-15}$-alkyl, $C_{2-15}$-alkenyl, $C_{2-15}$-alkynyl, each of which is optionally substituted with one or more independently selected from the group consisting of halogen(s), —$CF_3$, —CN, Y, phenyl and phenoxy; wherein phenyl or phenoxy is optionally substituted with one or more selected from the group consisting of halogen, —CN, $C_{1-4}$-alkyl, $C_{1-4}$-alkoxy, —$OCF_3$, and —$CF_3$;

provided that at least one alkyl atom of $R^{6'}$ is substituted with a hydroxyl group or $R^{6'}$ is a substituent selected from the group consisting of —$OR^8Y$, —$SR^8Y$, $OR^8$—Z—Y, —$SR^8ZY$, —O—$R^8$—Z—$R^7$ and —S—$R^8$—Z—$R^7$ wherein each —$OR^8Y$, —$SR^8Y$, $OR^8$—Z—Y, —$SR^8ZY$, —O—$R^8$—Z—$R^7$ and —S—$R^8$—Z—$R^7$ is substituted with a alkylhydroxyl;

Y is a 5 or 6 membered heterocyclic group;

Z is oxygen or sulphur;

$R^8$ is $C_{1-15}$-alkyl, $C_{2-15}$-alkenyl, $C_{2-15}$-alkynyl;

aryl and heteroaryl is optionally substituted with one or more independently selected from the group consisting of halogen, —CN, $C_{1-4}$-alkyl, $C_{1-4}$-alkoxy, $C_{1-4}$-alkylthio, $C_{1-4}$-alkylsulfone, $C_{1-4}$-alkylsulfoxide, —$OCF_3$, $NO_2$, $N(R^7)_2$, and —$CF_3$; heteroaryl group is a 5 or 6 membered heterocycle containing one to four N, O, or S atoms or a combination thereof.

Another process of this invention, illustrated by Scheme VIII, is the synthesis of 3-hydroxy-4-alkylthio-1,2,5-thiadiazoles by treating 3-halo-4-alkylthio-1,2,5-thiadiazoles with aqueous alkaline metal hydroxides in the presence or absence of a dipolar aprotic solvent. In this scheme, Hal has the meanings defined supra. and M is an alkali metal, W is O or S.

Scheme VIII

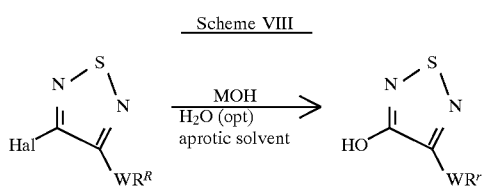

$R^R$ is hydrogen, $R^4$, $C_{3\text{-}10}$-cycloalkyl, $C_{4\text{-}12}$-(cycloalkylalkyl), $R^4$—Z—$C_{3\text{-}10}$-cycloalkyl and $R^4$—Z—$C_{4\text{-}12}$-(cycloalkylalkyl);

$R^4$ is selected from the group consisting of $C_{1\text{-}15}$-alkyl, $C_{2\text{-}15}$-alkenyl, and $C_{2\text{-}15}$-alkynyl, each of which is optionally substituted with one or more independently selected from the group consisting of halogen(s), —$CF_3$, Y, phenyl and phenoxy; wherein phenyl or phenoxy is optionally substituted with one or more selected from the group consisting of halogen, $C_{1\text{-}4}$-alkyl, $C_{1\text{-}4}$-alkoxy, and —$CF_3$; or $R^R$ is phenyl or benzyloxycarbonyl, each of which is optionally substituted with one or more selected from the group consisting of halogen, $C_{1\text{-}4}$-alkyl, $C_{1\text{-}4}$-alkoxy, and —$CF_3$; or $R^R$ is $R^4$—$OR^5Y$, $R^4$—$SR^5Y$, $R^4$—$OR^5$—Z—Y, $R^4$—$SR^5ZY$, $R^4$—O—$R^5$—Z—$R^4$ or $R^4$—S—$R^5$—Z—;

Z is oxygen or sulphur;

$R^5$ is selected from the group consisting of $C_{1\text{-}15}$-alkyl, $C_{2\text{-}15}$-alkenyl, and $C_{2\text{-}15}$-alkynyl;

Y is a 5 or 6 membered heterocyclic group; and $R^6$, and $R^7$ independently are hydrogen, $C_{1\text{-}6}$-alkyl, or $R^6$ and $R^7$ together with the nitrogen atom optionally form a 4- to 6-member ring;

$R^1$ and $R^2$ independently are hydrogen, $C_{1\text{-}15}$-alkyl, $C_{2\text{-}5}$-alkenyl, $C_{2\text{-}5}$-alkynyl, $C_{1\text{-}10}$-alkoxy, $C_{1\text{-}5}$-alkyl substituted with —OH, —$COR^{6'}$, $CH_2$—OH, halogen, —$NH_2$, carboxy, or phenyl;

$R^{6'}$ is hydrogen or $C_1$–$C_3$ alkyl;

W is O or S;

Hal is selected from Cl, Br, F, I, and if W is O then Hal may be $SO_2R^{4'}$;

$R^{4'}$ is $C_1$–$C_3$ alkyl or phenyl.

The compounds (11) are useful intermediates for the preparation of 1,2,5-thiadiazole compounds. The artisan will recognize that the intermediates 11 are useful for preparing 1,2,5-thiadiazole compounds as illustrated by the processes of Schemes I, II, and III.

When the G substituent contains a secondary nitrogen protected by a protecting group, the protecting group may be removed using standard methods known to the skilled artisan. An especially preferred protecting group is carbamate. One particularly useful reference concerning protecting groups is Greene, *Protecting Groups in Organic Synthesis*, (John Wiley & Sons, New York, 1981).

The concentration of the reactants is not critical. The art worker can alter the concentration of the reactants to achieve the desired rate of reaction and product yield.

The length of time for carrying out the processes described are not critical. As is always the case in chemistry, the rate of the reaction depends on a variety of factors, such as the temperature and the exact compound which is to be prepared. The course of the reaction may be followed using methods such as thin layer chromatography (TLC), high performance liquid chromatography (HPLC), gas chromatography (GC) and nuclear magnetic resonance spectroscopy (NMR) to detect the degree of completion of the reaction. The operator may obtain maximum yields using the process by extending the reaction time. Alternatively, the operator may wish to obtain maximum throughput by cutting off the reaction at the point at which it reaches an economical degree of completion.

When the product of a step in the following process is an oil, it may be isolated by standard methods. Such methods include distillation, flash chromatography, HPLC and the like.

As used herein the term "malfunctioning of the muscarinic cholinergic system" shall have the meaning accepted by the skilled artisan. For example the term shall refer to, but is not in any way limited to, conditions such as glaucoma, psychosis, schizophrenia or schizophreniform conditions, depression, sleeping disorders, epilepsy, and gastrointestinal motility disorders. Other such conditions include Alzheimer's Disease and incontinence.

The pharmacological properties of the compounds of the invention can be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labeled by $^3$H-Oxo. These sites have affinity of 1.8, 20 and 3000 nM, respectively. Using the present experimental conditions only the high and medium affinity sites are determined.

The inhibitory effects of compounds on $^3$H-oxo binding reflects the affinity for muscarinic acetylcholine receptors.

All preparations are performed at 0°–4° C. unless otherwise indicated. Fresh cortex (0.1–1 g) from male Wistar rats (150–250 g) is homogenized for 5–10 seconds in 10 mL 20 nM Hepes pH: 7.4, with an Ultra-Turrax homogenizer. The homogenizer is rinsed with 10 mL of buffer and the combined suspension centrifuged for 15 min. at 40,000× g. The pellet is washed three times with buffer. In each step the pellet is homogenized as before in 2×10 mL of buffer and centrifuged for 10 min. at 40,000× g.

The final pellet is homogenized in 20 mM Hepes pH: 7.4 (100 mL per g of original tissue) and used for binding assay. Aliquots of 0.5 mL is added 25 μL of test solution and 25 μL of $^3$H-Oxotremorine (1.0 nM, final concentration) mixed and incubated for 30 min. at 25° C. Non-specific binding is determined in triplicate using arecoline (1 μg/mL, final concentration) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non specific binding.

Test substances are dissolved in 10 mL water (if necessary heated on a steam-bath for less than 5 min.) at a concentration of 2.2 mg/mL. 25–75% inhibition of specific binding must be obtained before calculation of $IC_{50}$. The test value will be given as $IC_{50}$ (the concentration (nM) of the test substance which inhibits the specific binding of $^3$H-oxo by 50%).

$IC_{50}$=(applied test substance concentration) x$(C_x/C_o-C_x)$nM where $C_o$ is specific binding in control assays and $C_x$ is the specific binding in the test assay. (The calculations assume normal mass-action kinetics).

Furthermore the pharmacological properties of the compounds of the invention can also be illustrated by determining their capability to inhibit $^3$HPRZ (pirenzepine, [N-methyl-$^3$H]) binding to rat cerebral cortex membranes.

Pirenzepine binds selectively to subtype of muscarinic receptors. Historically the type is named the $M_1$-site, whereas pirenzepine sensitive site would be more appropriate. Although selective for $M_1$-sites pirenzepine also interact with $M_2$-sites.

All preparations are performed at 0°–4° C. unless otherwise indicated. Fresh cortex (0.1–1 9) from male Wistar rats (150–200 g) is homogenized for 5–10 s in 10 mL 20 mM Hepes pH: 7.4, with an Ultra-Turrax homogenizer. The homogenizer is rinsed with 2×10 mL of buffer and the combined suspension centrifuged for 15 min. at 40,000× g. The pellet is washed three times with buffer. In each step the pellet is homogenized as before in 3×10 mL of buffer and centrifuged for 10 min. at 40,000× g.

The final pellet is homogenized in 20 mM Hepes pH: 7.4 (100 mL per g of original tissue) and used for binding assay. Aliquots of 0.5 mL is added 20 µl of test solution and 25 µL of $^3$HPRZ (1.0 nM, final conc.), mixed and incubated for 60 min. at 20° C. Non-specific binding is determined in triplicate using atropine (1 µg/mL, final conc.) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non-specific binding.

Test substances are dissolved in 10 mL water, at a concentration of 0.22 mg/mL. 25–75% inhibition of specific binding must be obtained before calculation of $IC_{50}$.

The test value will be given as $IC_{50}$ (the concentration (nM) of the test substance which inhibits the specific binding of $^3$HPRZ by 50%). $IC_{50}$=(applied test substance concentration) $x(C_x/C_o-C_x)$nM where $C_o$ is specific binding in control assays and $C_x$ is the specific binding in the test assay. (The calculations assume normal mass-action kinetics).

Test results obtained by testing some compounds of the present invention will appear from the following table 1.

TABLE 1

| Compound | $^3$H-Oxo $IC_{50}$, nM | $^3$HPRZ $IC_{50}$, nM |
| --- | --- | --- |
| 12 | 73 | 86 |
| 5 | 162 | 183 |
| 6 | 17 | 32 |
| 7 | 10.7 | 26 |
| 8 | 3.1 | 7.4 |
| 9 | 11 | 25 |
| 10 | 6.1 | 22 |
| 11 | 29 | 33 |
| 13 | 1.4 | 3.7 |
| 14 | 1.3 | 1.9 |
| 15 | 1.6 | 2.3 |
| 17 | 5.2 | 8.8 |
| 18 | 101 | 73 |
| 33 | 51 | 48 |
| 35 | 23 | 33 |
| 36 | 204 | 217 |
| 31 | 32 | 12 |
| 27 | 123 | 370 |
| 28 | 37 | 25 |
| 30 | 69 | 19 |
| 26 | 11 | 37 |
| 25 | 1.8 | 2.1 |
| 29 | 34 | 20 |
| 34 | 86 | 10 |
| 22 | 23 | 7.4 |
| 23 | 55 | 18 |
| 24 | 19 | 19 |
| 32 | 77 | 45 |
| 19 | 0.36 | 7.5 |
| 20 | 2.6 | 4 |
| 21 | 4.4 | 4 |

TABLE 1-continued

| | | |
| --- | --- | --- |
| 16 | 6.4 | 2 |
| 38 | 1 | 1.9 |
| 39 | 13 | 15 |
| 40 | 1.8 | 2.5 |
| 41 | 25 | 19 |
| 42 | 14 | 9.3 |
| 43 | 29 | 33 |
| 44 | 7.1 | 15 |
| 46 | >1000 | >1000 |
| 47 | 54 | 23 |
| 48 | 14 | 27 |
| 49 | 1.8 | 1.9 |
| 50 | 92 | 351 |
| 51 | 25 | 112 |
| 52 | >1000 | 475 |
| 53 | 24 | 35 |
| 55 | 11 | 23 |
| 57 | 88 | 37 |
| 59 | 104 | 102 |
| 60 | 19 | 14 |
| 61 | 1.1 | 5.8 |
| 45 | 29 | 4.6 |
| 69 | 29 | 20 |
| 65 | 2.3 | 0.72 |
| 70 | 1.3 | 0.65 |
| 71 | 1.1 | 1.15 |
| 72 | 1.9 | 0.55 |

| Compound # | Oxo-M IC-50, nM | Pir IC-50 nM |
| --- | --- | --- |
| 73 | 4.1 | 6.5 |
| 74 | 24 | 40 |
| 75 | 65 | 128 |
| 99 | 41 | 70 |
| 100 | 873 | 846 |
| 101 | 88 | 36 |
| 102 | 378 | 187 |
| 103 | 107 | 115 |
| 104 | 107 | 115 |
| 105 | 7.9 | 65.6 |
| 106 | 9.5 | 95.4 |
| 107 | 9.6 | 22.4 |
| 108 | 9.1 | 56.1 |
| 109 | 12.3 | 58.3 |
| 110 | 13.2 | 50.4 |
| 111 | 38 | 85 |
| 112 | 16 | 153 |
| 113 | 3.6 | 23 |
| 114 | 9.3 | 43 |
| 115 | 19 | 532 |
| 116 | 14 | 33 |
| 117 | 32 | 238 |
| 118 | 7.2 | 70 |
| 119 | 17 | 124 |
| 120 | 11 | 71 |
| 121 | 12 | 146 |
| 122 | 11 | 45 |
| 123 | 42 | 106 |
| 124 | 5.8 | 54 |
| 125 | 36 | 191 |
| 126 | 19 | 72 |
| 127 | 61 | 373 |
| 128 | 6.9 | 109 |
| 129 | nd | nd |
| 131 | 5.6 | 46 |
| 132 | 11 | 66 |
| 133 | >1000 | >1000 |
| 134 | 55 | 227 |
| 135 | >1000 | >1000 |
| 136 | 2.73 | 6.42 |
| 137 | 7.39 | 2.10 |
| 138 | 0.65 | 0.47 |
| 139 | 230 | 145 |
| 142 | 38 | 74 |
| 143 | 1399 | 637 |
| 144 | 12 | 9 |
| 146 | 775 | >1000 |
| 147 | 1.1 | 1.15 |

TABLE 1-continued

| | | |
|---|---|---|
| 148 | 8 | 25 |
| 207 | 2.4 | 6 |
| 149 | 14 | 30 |
| 150 | 17 | 36 |
| 151 | 2071 | 2702 |
| 152 | 436 | 243 |
| 153 | 597 | 205 |
| 154 | 11 | 6.3 |
| 155 | 3.4 | 8.8 |
| 156 | 1 | 0.6 |
| 160 | 14 | 6.3 |
| 161 | 6.8 | 5.3 |
| 162 | 179 | 128 |
| 164 | 5.28 | 16.64 |
| 167 | 2.8 | 2.0 |
| 168 | 1.0 | 6.4 |
| 169 | 1.0 | 1.9 |
| 170 | 1.5 | 3.0 |
| 171 | 19 | 27 |
| 172 | 5.2 | 10 |
| 173 | 1.0 | 1.4 |
| 174 | 2.1 | 12 |
| 175 | 0.74 | 2.7 |
| 176 | 1.3 | 3.0 |
| 177 | 1.1 | 2.0 |
| 178 | 15 | 61 |
| 180 | 4.7 | 11 |
| 181 | 1.1 | 2.2 |
| 182 | 0.6 | 3.5 |
| 183 | 2.6 | 9.9 |
| 184 | 1.2 | 2.2 |
| 185 | 0.76 | 2.0 |
| 186 | 0.59 | 2.8 |
| 187 | 2.8 | 1.6 |
| 188 | 12 | 43 |
| 189 | 1.7 | 3.8 |
| 190 | 3.9 | 2.5 |
| 191 | 1.4 | 9.5 |
| 192 | 13 | 21 |
| 193 | 3.7 | 10 |
| 194 | 2.1 | 4 |
| 195 | 4.9 | 7.5 |
| 196 | 5.2 | 8.8 |
| 197 | 2.3 | 6.9 |
| 198 | 31 | 120 |
| 199 | 3.3 | 5.4 |
| 200 | 16 | 12 |
| 201 | 3.7 | 3.1 |
| 202 | 13 | 31 |
| 203 | 3.1 | 4.3 |
| 204 | 59 | 153 |
| 205 | 2.5 | 3.0 |
| 206 | 6.1 | 5.0 |

'nd' as used herein refers to values not yet determined.

Table II illustrates several additional formula I compounds as claimed herein.

TABLE II

| R | W | r | G* | $R^{1*}$ | $R^{2*}$ | $R^3$ | n | m | p/g** |
|---|---|---|---|---|---|---|---|---|---|
| H | S | 0 | het-6 (C-2) | H | $CH_3$ C-3 | — | 1 | 1 | 2 |
| Cl | S | 1 | het-5 (C-2) | $CH_3$ C-3 | H | H | — | — | — |
| Br | O | 2 | het-6 (C-3) | $CH_2OH$ C-2 | H | — | 1 | 1 | 2 |
| $NH_2$ | O | 1 | het-4 (C-3) | $CH_2COCH_3$ C-4 | H | H | — | 1 | 1 |
| $NHC_2H_5$ | S | 0 | het-3 (uns) (C-3) | $CH=CH_2$ C-4 | $CH_3$ C-2 | CH | 1 | 2 | 0 |
| $NCH_3CH_3$ | O | 0 | het-7 (uns) (C-3) | $C_2H_3(CH_2OH)CH_3$ C-5 | H | $C_2H_5$ | — | 2 | 1 |
| —$NHCH_3$ | S | 0 | het-1 (C-3) | $CH_3$ C-2 | H | $CH_3$ | — | — | — |
| —Br | O | 1 | het-2 (sat) (C-4) | H | H | $C_2H_5$ | — | — | — |
| —I | O | 2 | het-6 (C-4) | H | $C_6H_{13}$ C-3 | — | 2 | 0 | 1 |
| —$OCH_3$ | S | 0 | het-1 (C-3) | CHCl C-3 | H | H | — | — | — |
| —$SC_2H_5$ | S | 1 | het-2 (uns) (C-3) | $CHNH_2$ C-2 | CHBr C-4 | $CH_3$ | — | — | — |
| —$SOCH=CH_2$ | O | 0 | het-3 (sat) (C-4) | CHC(O)OH C-3 | H | $CH=CH_2$ | 0 | 2 | 2 |
| cyclohexyl | S | 1 | het-4 (C-4) | $CH_3$ C-4) | $CH_3$ C-5 | H | — | 1 | 1 |
| cylopentyl methyl- | O | 0 | het-6 (C-5) | $C\equiv C_2H_3$ C-4 | H | — | 0 | 2 | 1 |
| —S-cyclo- butyl | S | 2 | het-7 (sat) (C-4) | $CH_3$ C-3 | $C_2H_5$ C-6 | H | — | 1 | 0 |
| —O-cyclo- propylethyl | O | 0 | het-5 (C-3) | H | H | H | — | — | — |
| $OC_2H_5(CH_3)Cl$ | S | 1 | het-7 (uns) (C-5) | $OC_2H_5H$ C-4 | H | H | — | 0 | 2 |

*As used in Table I, the C-number in the second row of the description of each compound rerers to the point of attachment on the ring for the indicated variable.
**As used in Table I, the p/q column refers to the value for the appropriate variable for the designated G value. For example when G is het-7, the p/q column provides the value for q.

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients suffering from diseases in the central nervous system caused by malfunctioning of the muscarinic cholinergic system it may frequently be necessary to begin with a dosage of from about 20 to about 70 mg per day and when the condition is under control to reduce the dosage as low as from about 0.1 to about 10 mg per day. The exact dosage will depend upon the mode of administration, form in which administered, the subject to be treated and the body weight of the subject to be treated, and the preference and experience of the physician or prescribing caregiver in charge.

The route of administration may be any route, which effectively transports the active compound to the appropriate or desired site of action, such as oral or parenteral e.g. rectal, transdermal, depot, subcutaneous intravenous, intramuscular or intranasal, the oral route being preferred.

Typical compositions include a compound of formula I or a pharmaceutically acceptable acid addition salt thereof, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 0.1 to about 100 mg in a pharmaceutically acceptable carrier per unit dosage.

The compounds of this invention may be suitable for administration to an animal. Such animals include both domestic animals, for example livestock, laboratory animals, and household pets, and non-domestic animals such as wildlife. More preferredly, the animal is a vertebrate. Most preferredly, a compound of this invention shall be administered to a mammal. It is especially preferred that the animal is a domestic mammal or a human. The most preferred mammal is a human. For such purposes, a compound of this invention may be administered as a feed additive.

In order to more fully illustrate the operation of this invention, the following formulation examples are provided. The examples are illustrative only, and are not intended to limit the scope of the invention in any way.

Formulation 1

A typical tablet, appropriate for use in this method, may be prepared using conventional techniques and may contain:

|  | Amount per Tablet | Concentration by Weight (%) |
| --- | --- | --- |
| (±)-Endo-3-butylthio-4-(1-azabicyclo[3.2.1]-octyl-6-oxy)-1,2,5-thiadiazole | 5.0 mg | 4.7 |
| Lactosum | 67.8 mg Ph. Eur. | 64.2 |
| Avicel ® | 31.4 mg | 29.8 |
| Amberlite ® | 1.0 mg | 1.0 |
| magnesium stearate | 0.25 mg | 0.3 |
|  | 105.45 mg | 100 |

Formulation 2

Hard gelatin capsules are prepared using the following ingredients:

|  | Amount per Tablet | Concentration by Weight (%) |
| --- | --- | --- |
| (±)-Exo-3-butyloxy-4-(N-methyl-8-azabicyclo-[3.2.1]octyl-3-oxy)-1,2,5-thiadiazole | 0.1 mg | 0.05 |
| starch dried | 200 mg | 95.2 |
| magnesium stearate | 10 mg | 4.8 |
|  | 210.1 mg | 100 |

The above ingredients are mixed and filled into hard gelatin capsules in 210.1 mg quantities.

Formulation 3

Suspensions each containing 1 mg of medicament per 5 mL dose are as follows:

|  | Amount per 5 mL of suspension |
| --- | --- |
| (±)-3-(3-phenylethylthio)-4-(1-azabicyclo[2.2.2]octyl-3-oxy)-1,2,5-thiadiazole | 1 mg |
| sodium carboxymethyl cellulose | 50 mg |
| syrup | 1.25 mL |
| benzoic acid solution | 0.10 mL |
| flavor | q.v. |
| color | q.v. |
| water | q.s. to 5 mL |

The medicament is passed through a No. 45 mesh U.S. sieve and mixed with the sodium carboxymethyl cellulose and syrup to form a smooth paste. The benzoic acid solution, flavor and color is diluted with some of the water and added to the paste with stirring. Sufficient water is then added to produce the required volume.

The intermediates and processes of the present invention are useful for preparing compounds having beneficial muscarinic receptor activity. The compounds of the present invention have such useful muscarinic receptor activity. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some preferred characteristics of compounds of formula I are:

A) W is O;
B) r is 1 or 2;
C) G is selected from het-1 and het-5;
D) G is unsaturated;
E) G is het-4;
F) G is an azabicycle having 7 ring carbon atoms and a nitrogen atom;
G) G is het-6;
H) r is 0;
I) R is selected from halogen, —OR$^5$Y, —SR$^5$Y, —OR$^5$ZY, —SR$^5$ZY, —OR$^5$ZR$^4$, —SR$^5$ZR$^4$, —OR$^4$, and —SR$^4$;
J) W is S;
K) m is 1;
L) n is 1;
M) p is 2;
N) V is O or S;
O) G is het-2
P) G is selected from the following heterocycles:

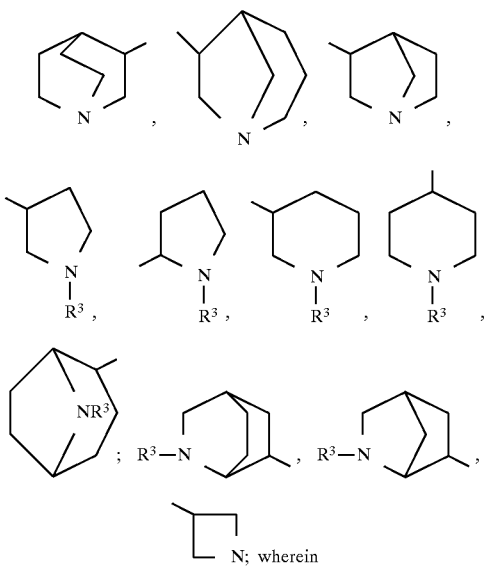

wherein the point of attachment to the —(CH$_2$)$_r$—W— group is as indicated;

Q) G groups is selected from the group consisting of

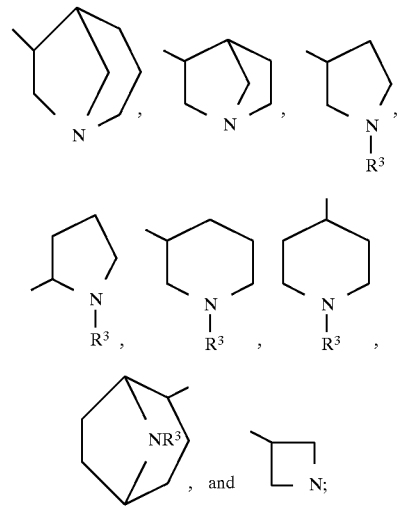

R) G is not an azabicycle;
S) G is het-3;
T) R is not OR$^4$ wherein R$^4$ is C$_1$–C$_3$ alkyl;
U) R$^4$ is C$_4$–C$_{15}$ alkyl;
V) G is an azacyclic or azabicyclic group;
W) R is selected from the group consisting of —OR$^5$Y, —SR$^5$Y, OR$^5$—Z—Y, —SR$^5$ZY, —O—R$^4$—Z—R$^5$ or —S—R$^4$—Z—R$^5$, wherein Z is oxygen or sulphur, R$^5$ is C$_{1-15}$-alkyl, C$_{2-15}$-alkenyl, C$_{2-15}$-alkynyl, Y is a 5 or 6 membered heterocyclic group containing one to four N, O or S atom(s) or a combination thereof, R$_4$ is C$_{1-5}$-alkyl, C$_{2-15}$-alkenyl, C$_{2-15}$-alkynyl;

Especially preferred compounds of formula I have the characteristics of A–E; characteristics of A, G, H, M; characteristics of G–O; A, H, R; B, I, J; J, K S; A, K, Q; J, P, L; or the characteristics of F,G–J,M.

Some preferred characteristics of the process and intermediates of this invention are:

A) W is O;
B) R$^{15}$ and R$^{16}$ are not each hydrogen;
C) R$^{10}$, R$^{11}$ and R$^{12}$ are each methyl;
D) R is selected from the group consisting of phenyl, benzyloxycarbonyl, —OR$^5$Y, —SR$^5$Y, OR$^5$—Z—Y, —SR$^5$ZY, —O—R$^4$—Z—R$^5$ or —S—R$^4$—Z—R$^5$, —SOR$^4$, C$_{3-10}$-cycloalkyl, C$_{4-12}$-(cycloalkylalkyl), —Z—C$_{3-10}$-cycloalkyl and —Z—C$_{4-12}$-(cycloalkylalkyl) wherein Z is oxygen or sulphur, R$^5$ is C$_{1-15}$-alkyl, C$_{2-15}$-alkenyl, C$_{2-15}$-alkynyl, Y is a 5 or 6 membered heterocyclic group containing one to four N, O or S atom(s) or a combination thereof, R$_4$ is C$_{1-15}$-alkyl, C$_{2-15}$-alkenyl, C$_{2-15}$-alkynyl;
E) R is selected from the group consisting of halogen, —OR$^4$, and —SR$^4$;
F) G is an azabicycle having 6 ring carbon atoms and a nitrogen atom;
G) R$^{15}$ and R$^{16}$ are selected from the group consisting of (R$^{10}$R$^{11}$R$^{12}$Si) and (R$^{13}$R$^{14}$R$^{15}$'Si)
H) R$^{18}$ is R$^4$SO$_2$;
I) W is S;
J) R is selected from the group of —OR, —SR, and I.
K) R$^{17}$ is alkyl or R$^{19}$ substituted alkyl;
L) W' is S or SO$_2$;

M) When the compound is of Formula V, the $R^{18}$ is $R^4SO_2$, Br or I;

N) R is not $OR^4$ wherein $R^4$ is $C_1$–$C_3$ alkyl;

O) $R^4$ is $C_4$–$C_{15}$ alkyl;

P) G is an azacyclic or azabicyclic group;

Q) R is selected from the group consisting of —$OR^5Y$, —$SR^5Y$, $OR^5$—Z—Y, —$SR^5ZY$, —O—$R^4$—Z—$R^5$ or —S—$R^4$—Z—$R^5$, wherein Z is oxygen or sulphur, $R^5$ is $C_{1-15}$-alkyl, $C_{2-15}$-alkenyl, $C_{2-15}$-alkynyl, Y is a 5 or 6 membered heterocyclic group containing one to four N, C or S atom(s) or a combination thereof, $R_4$ is $C_{1-15}$-alkyl, $C_{2-15}$-alkenyl, $C_{2-15}$-alkynyl;

Especially preferred characteristics of the process and intermediates of this invention are A–F; characteristics of B,C,E; characteristics of H,J,K; K,L,M; or the characteristics of B–F,I.

The invention will now be described in further detail with reference to the following examples. The examples are provided for illustrative purposes, and are not to be construed as limiting the scope of the invention in any way.

EXAMPLE 1

3-Chloro-4-(1-butylthio)-1,2,5-thiadiazole

Cyanogen (36 g, 0.69 mol) was bubbled into ether (250 mL) maintained at –10° C. To the solution was added dropwise diethylamine (3 mL) followed by dropwise addition of 1-butylthiol (47 mL, 0.64 mol) at such a rate that the temperature did not exceed –5° C. The reaction was maintained below 0° C. for 5 h then stirred at ambient overnight. Ether was distilled from the reaction until the pot temperature reached 50° C. The reaction was cooled to ambient and then added dropwise to a solution of sulfur monochloride (55 mL, 0.688 mol) in DMF (50 mL) that was cooled to 5° C. Cooling was removed and reaction was stirred overnight. The reaction was cooled in an ice-water bath and excess sulfur monochloride destroyed by careful addition of $H_2O$ while maintaining the temperature below 40° C. The liquid was decanted from the semi-solid sulfur precipitant and the sulfur residue triturated with hexane. The aqueous fraction was extracted with hexane (3×) and the combined extracts and triturants were washed with $H_2O$, aqueous $NaHCO_3$, brine, dried, and the solvent evaporated. The residue was distilled at 2 mm Hg to give a yellow liquid (24.6 g), b.p. 105°–110° C. (Compound 1).

EXAMPLE 2

3-Chloro-4-butylsulfonyl-1,2,5-thiadiazole

A solution of Oxone™ (12 g, 0.0195 mol) in $H_2O$ (60 mL) was vigorous stirred as 3-chloro-4-butylthio-1,2,5-thiadiazole (2.1 g, 0.01 mol) in THF (30 mL) was added dropwise. After 24 h, the THF was evaporated and the residue extracted with ether (3×). Extracts were washed with $H_2O$, dried, and solvent evaporated to give a clear liquid. Radial chromatography eluting with 30% EtOAc/hexane gave a colorless liquid (2.3 g). (Compound 2).

EXAMPLE 3

3-Chloro-4-ethylthio-1,2,5-thiadiazole

Cyanogen (36 g, 0.69 mol) was bubbled into ether (250 mL) maintained at –10° C. To the solution was added dropwise diethylamine (3 mL) followed by dropwise addition of ethanethiol (47 mL, 0.64 mol) at such a rate that the temperature did not exceed –5° C. The reaction was maintained below 0° C. for 5 h then stirred at ambient temperature overnight. Ether was distilled from the reaction until the pot temperature reached 50° C. The reaction was cooled to ambient and then added dropwise to a solution of sulfur monochloride (125 mL, 1.56 mol) in DMF (150 mL) that was cooled to 5° C. Cooling was removed and the reaction was stirred overnight. The reaction was cooled in an EtOH-ice bath as the excess sulfur monochloride was destroyed by dropwise addition of water while maintaining the temperature below 35° C. The liquid was decanted from the semi-solid sulfur precipitant and the sulfur residue triturated with hexane. The aqueous fraction was extracted with hexane (3×) and the combined extracts and triturants were washed with $H_2O$, aqueous $NaHCO_3$, brine, dried, and the solvent evaporated. The brown liquid residue was distilled at 3 mm Hg to give a yellow liquid (80.2 g), b.p. 91°–96° C. (Compound 3).

EXAMPLE 4

3-Chloro-4-ethylsulfonyl-1,2,5-thiadiazole

A solution of Oxone (84 g, 0.137 mol) in $H_2O$ (400 mL) was rapidly stirred as 3-chloro-4-ethylthio-1,2,5-thiadiazole (12.2 g, 0.067 mol) in THF (200 mL) was added. After stirring overnight, the THF was evaporated and the residue extracted with ether (3×). The extracts were washed with $H_2O$, aqueous $NaHCO_3$, and brine then the solvent dried and evaporated to give a clear liquid (13.6 g). (Compound 4).

EXAMPLE 5

(±)-3-Methoxy-4-(1-azabicyclo[2.2.2]octyl-3-oxy)-1,2,5-thiadiazole

A solution of 1-azabicyclo[2.2.2]octan-3-ol (1.36 g, 0.0104 mol) in THF (20 mL) was treated dropwise with 1.6M n-butyllithium in hexane (7.4 mL, 0.0118 mol). To this solution was added 3-methoxy-4-methanesulfonyl-1,2,5-thiadiazole (2.08 g, 0.0107 mol) in THF (40 mL), the reaction heated to 40° C. for 2 h, and then stirred at ambient temperature overnight. The solvent was evaporated, the residue acidified with 1N HCl, and the mixture extracted with ether. The aqueous solution was made basic and extracted with EtOAc. The extracts were washed with $H_2O$, dried, and the solvent evaporated. The residue was purified by radial chromatography (2.5% EtOH-0.25% $NH_4OH$—$CHCl_3$) to give a clear oil. The HCl salt of the oil (0.85 g) crystallized from MeOH—EtOAc, m.p. 197°–198° C. (Compound 5).

EXAMPLE 6

(±)-3-Ethoxy-4-(1-azabicyclo[2.2.2]octyl-3-oxy)-1,2,5-thiadiazole

A solution of 1-azabicyclo[2.2.2]octan-3-ol (0.75 g, 0.0059 mol) in THF (50 mL) was treated dropwise with 1.6M n-butyllithium in hexane (3.7 mL, 0.0059 mol). To this solution was added 3-ethoxy-4-methanesulfonyl-1,2,5-thiadiazole (1.0 g, 0.0048 mol) in THF (12 mL) and the reaction heated to 60° C. for 5 h. The solvent was evaporated, the residue acidified with 1N HCl, and the mixture extracted with ether. The aqueous solution was made basic and extracted with ether. The extracts were washed with $H_2O$, dried, and the solvent evaporated to give a clear oil. The HCl salt of the oil (0.47 g) crystallized from 2-propanol, m.p. 212°–213° C. (Compound 6).

EXAMPLE 7

(±)-3-Propyloxy-4-(1-azabicyclo[2.2.2]octyl-3-oxy)-
1,2,5-thiadiazole

A solution of 1-azabicyclo[2.2.2]octan-3-ol (1.1 g, 0.0087 mol) in THF (75 mL) was treated dropwise with 1.6 M n-butyllithium in hexane (5.0 mL, 0.008 mol). To this solution was added 3-propyloxy-4-methanesulfonyl-1,2,5-thiadiazole (1.3 g, 0.0059 mol) in THF (15 mL) and the reaction heated to 60° C. for 4 h. The solvent was evaporated, the residue acidified with 1N HCl, and the mixture extracted with ether. The aqueous solution was made basic and extracted with EtOAc. The extracts were washed with $H_2O$, dried, and the solvent evaporated to give a clear oil. The HCl salt of the oil (0.59 g) crystallized from 2-propanol, m.p. 218°–219° C. (Compound 7).

EXAMPLE 8

(±)-3-Butyloxy-4-(1-azabicyclo[2.2.2]octyl-3-oxy)-
1,2,5-thiadiazole

A solution of 1-azabicyclo[2.2.2]octan-3-ol (2.2 g, 0.0168 mol) in THF (25 mL) was treated dropwise with 1.6 M n-butyllithium in hexane (10.8 mL, 0.0173 mol). To this solution was added 3-butyloxy-4-methanesulfonyl-1,2,5-thiadiazole (1.98 g, 0.084 mol) in THF (25 mL) and the reaction heated to 52° C. for 3.5 h. The solvent was evaporated, the residue acidified with 1N HCl, and the mixture extracted with ether. The aqueous solution was made basic and extracted with EtOAc. The extracts were washed with $H_2O$, dried, and the solvent evaporated to give a clear oil. The HCl salt of the oil (2.0 g) crystallized from $CHCl_3$—EtOAc-ether, m.p. 204°–205° C. (compound 8).

EXAMPLE 9

(±)-3-Pentyloxy-4-(1-azabicyclo[2.2.2]octyl-3-oxy)-
1,2,5-thiadiazole

A solution of 1-azabicyclo[2.2.2]octan-3-ol (0.75 g, 0.0059 mol) in THF (50 mL) was treated dropwise with 1.6M n-butyllithium in hexane (3.7 mL, 0.0059 mol). To this solution was added 3-pentyloxy-4-methanesulfonyl-1,2,5-thiadiazole (1.0 g, 0.004 mol) in THF (10 mL) and the reaction heated to 60° C. for 4 h. The solvent was evaporated, the residue acidified with 1N HCl, and the mixture extracted with ether. The aqueous solution was made basic and extracted with ether. The extracts were washed with $H_2O$, dried, and the solvent evaporated to give a clear oil. The HCl salt of the oil (0.75 g) crystallized from EtOAc, m.p. 171°–172° C. (Compound 9).

EXAMPLE 10

(±)-3-Hexyloxy-4-(1-azabicyclo[2.2.2]octyl-3-oxy)-
1,2,5-thiadiazole

A solution of 1-azabicyclo[2.2.2]octan-3-ol (2.2 g, 0.0168 mol) in THF (25 mL) was treated dropwise with 1.6 M n-butyllithium in hexane (10.8 mL, 0.0173 mol). To this solution was added 3-hexyloxy-4-methanesulfonyl-1,2,5-thiadiazole (2.2 g, 0.004 mol) in THF (25 mL) and the reaction heated to 52° C. for 3.5 h. The solvent was evaporated, the residue acidified with 1N HCl, and the mixture extracted with ether. The aqueous solution was made basic and extracted with ether. The extracts were washed with $H_2O$, dried, and the solvent evaporated to give a clear oil. The HCl salt of the oil (1.76 g) crystallized from EtOAc, m.p. 165°–166° C. (Compound 10).

EXAMPLE 11

(±)-3-(4-Methylpentyloxy)-4-(1-azabicyclo[2.2.2]
octyl-3-oxy)-1,2,5-thiadiazole

A solution of 1-azabicyclo[2.2.2]octan-3-ol (0.75 g, 0.0059 mol) in THF (50 mL) was treated dropwise with 1.6M n-butyllithium in hexane (3.7 mL, 0.0059 mol). To this solution was added 3-(4-methylpentyloxy)-4-methanesulfonyl-1,2,5-thiadiazole (1.2 g, 0.0045 mol) in THF (10 mL) and the reaction heated to reflux for 6 h. The solvent was evaporated, the residue acidified with 1N HCl, and the mixture extracted with ether. The aqueous solution was made basic and extracted with ether. The extracts were washed with $H_2O$, dried, and the solvent evaporated to give a clear oil. The HCl salt of the oil (1.1 g) crystallized from EtOAc, m.p. 179°–180° C. (Compound 11).

EXAMPLE 12

(±)-3-Chloro-4-(1-azabicyclo[2.2.2]octyl-3-oxy)-1,2,
5-thiadiazole

A solution of 1-azabicyclo[2.2.2]octan-3-ol (1.1 g, 0.0084 mol) in THF (25 mL) was treated dropwise with 1.6 M n-butyllithium in hexane (5.4 mL, 0.0086 mol). This solution was added dropwise to a solution of 3-chloro-4-butylsulfonyl-1,2,5-thiadiazole (2.1 g, 0.0086 mol) in THF (15 mL) at such a rate that the temperature did not exceed 32° C. After stirring for 3 days, the reaction was treated with $H_2O$ (10 mL), diluted with ether (100 mL), and extracted with 1N HCl (25 mL). The aqueous solution was washed with ether, made basic, and extracted with ether. The extracts were dried, the solvent evaporated, and the residue purified by radial chromatography (2.5% EtOH-0.25% $NH_4OH$—$CHCl_3$) to give a straw colored liquid (1.1 g). The oxalate salt (0.39 g) crystallized from MeOH—EtOAc, m.p. 154°–156° C. (Compound 12).

Alternative synthesis of (±)-3-Chloro-4-(1-
azabicyclo[2.2.2]octyl-3-oxy)-1,2,5-thiadiazole:

A solution of 1-azabicyclo[2.2.2]octan-3-ol (1.2 g, 0.0092 mol) in THF (25 mL) was treated dropwise with 1.6 M n-butyllithium in hexane (5.9 mL, 0.0095 mol). The solution was cooled to −8° C. and a solution of 3-chloro-4-ethylsulfonyl-1,2,5-thiadiazole (1.83 g, 0.0086 mol) in THF (15 mL) was added dropwise. After 15 min, cooling was removed and the reaction stirred overnight. The reaction was treated with $H_2O$ (10 mL), diluted with ether (100 mL), and extracted with 1N HCl (25 mL). The aqueous solution was washed with ether, made basic, and extracted with ether. The extracts were dried and the solvent evaporated to give crude (compound 12) (1.05 g) as a brownish liquid.

Alternative synthesis of (±)-3-Chloro-4-(1-
azabicyclo[2.2.2]octyl-3-oxy)-1,2,5-thiadiazole:

A mixture of 1-azabicyclo[2.2.2]octan-3-ol (12.7 g, 0.1 mol), triethylamine (0.3 mL), and $CHCl_3$ (150 mL) was cooled to 5° C. and cyanogen (7.25 g, 0.139 mol) bubbled into the mixture. The reaction was stirred another hour then allowed to come to ambient temperature overnight. The solvent was evaporated, the residue dissolved in DMF (20 mL), and the solution added dropwise to a solution of $S_2Cl_2$ (47.3 g, 0.35 mol) in DMF (30 mL) that was cooled in an ice-water bath. After addition, cooling was removed and reaction exothermed to 32° C. After 5 h, reaction cooled and excess $S_2Cl_2$ destroyed by careful addition of $H_2O$. The reaction was diluted with more $H_2O$ (300 mL) and the aqueous solution decanted from the sulfur residue. The sulfur residue was triturated with $H_2O$ and the combined aqueous solutions evaporated to a small volume (150 mL). The solution was washed with ether and then made basic with 50% NaOH while maintaining the temperature below 30° C. The mixture was extracted with $CHCl_3$, the extracts dried, and the solvents thoroughly evaporated. The residue was suspended in ether, dried, filtered and the solvent evaporated to give (compound 12) (18.1 g) as a yellow oil that slowly solidified.

EXAMPLE 13

(±)-3-Propylthio-4-(1-azabicyclo[2.2.2]octyl-3-oxy)-1,2,5-thiadiazole

A solution of the crude compound 12 (1.67 g, 0.0068 mol) in DMF (25 mL) was treated portionwise with freshly ground flaked $Na_2S-9H_2O$ (1.8 g, 0.0075 mol). After 40 min, 1-bromopropane (1.25 g, 0.010 mol) was added and the reaction stirred overnight. The solvent was evaporated, the residue was acidified with 1N HCl, and the mixture extracted with ether. The aqueous was made basic and extracted with ether. The extracts were dried and the solvent evaporated to give a straw-colored liquid. The HCl salt (1.28 g) crystallized from $CHCl_3$—EtOAc-ether, m.p. 174°–176° C. (Compound 13).

EXAMPLE 14

(±)-3-Butylthio-4-(1-azabicyclo[2.2.2]octyl-3-oxy)-1,2,5-thiadiazole

A solution of the crude compound 12 (1.8 g, 0.0073 mol) in DMF (25 mL) was treated portionwise with freshly ground flaked $Na_2S-9H_2O$ (1.94 g, 0.0081 mol). After 1 h, 1-iodobutane (2 g, 0.011 mol) was added and the reaction stirred overnight. The solvent was evaporated, the residue was acidified with 1N HCl, and the mixture extracted with ether. The aqueous was made basic and extracted with ether. The extracts were dried and the solvent evaporated to give a straw-coloured liquid. The HCl salt (1.82 g) crystallized from $CHCl_3$—EtOAc-ether, m.p. 151°–153° C. (Compound 14).

EXAMPLE 15

(±)-3-Pentylthio-4-(1-azabicyclo[2.2.2]octyl-3-oxy)-1,2,5-thiadiazole

A solution of the crude compound 12 (1.67 g, 0.0068 mol) in DMF (25 mL) was treated portionwise with freshly ground flaked $Na_2S-9H_2O$ (1.8 g, 0.0075 mol). After 1 h, 1-bromopentane (1.53 g, 0.010 mol) was added and the reaction stirred overnight. The solvent was evaporated, the residue was acidified with 1N HCl, and the mixture extracted with ether. The aqueous was made basic and extracted with ether. The extracts were dried and the solvent evaporated to give a straw-coloured liquid. The HCl salt (1.07 g) crystallized from $CHCl_3$—EtOAc-ether, m.p. 186°–187° C. (Compound 15).

EXAMPLE 16

(S)-3-Pentylthio-4-(1-azabicyclo[2.2.2]octyl-3-oxy)-1,2,5-thiadiazole

A solution of (S)-1-azabicyclo[2.2.2]octan-3-ol (2.0 g, 0.0157 mol) in THF (40 mL) was cooled to 10° C. as 1.6M n-butyllithium in hexane (10 mL, 0.016 mol) was added dropwise. The resulting mixture was treated with 3-chloroethylsulfonyl-1,2,5-thiadiazole (3.34 g, 0.0157 mol) in THF (25 mL) and stirred for 16 h. The reaction was treated with $H_2O$ (10 mL), ether (170 mL) and extracted with 1N HCl (43 mL). The aqueous fraction was washed with ether, made basic, and extracted with ether. The extracts were dried and the solvent evaporated to give an oil (1.7 g). The oil was dissolved in DMF (25 mL), treated portionwise with freshly ground flaked $Na_2S-9H_2O$ (1.83 g, 0.0076 mol), and heated (40° C.). After 1.25 h, 1-bromopentane (1.58 g, 0.0105 mol) was added and the reaction stirred overnight. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (5% EtOH-0.5% $NH_4OH$—$CHCl_3$). The HCl salt (0.87 g) crystallized from $CHCl_3$—EtOAc-ether, m.p. 194°–195° C., $[\alpha]_D$=25.41° (EtOH). (Compound 16).

EXAMPLE 17

(±)-3-Hexylthio-4-(1-azabicyclo[2.2.2]octyl-3-oxy)-1,2,5-thiadiazole

A solution of the crude compound 12 (1.8 g, 0.0073 mol) in DMF (25 mL) was treated portionwise with freshly ground flaked $Na_2S-9H_2O$ (1.94 g, 0.0081 mol). After 1 h, 1-iodohexane (2.3 g, 0.011 mol) was added and the reaction stirred overnight. The solvent was evaporated, the residue was acidified with 1N HCl, and the mixture extracted with ether. The aqueous was made basic and extracted with ether. The extracts were dried and the solvent evaporated to give a straw-colored liquid. The HCl salt (1.0 g) crystallized from $CHCl_3$—EtOAc-ether, m.p. 165°–167° C. (Compound 17).

EXAMPLE 18

(±)-3-(3,3-Dimethylbutylthio)-4-(1-azabicyclo[2.2.2]octyl-3-oxy)-1,2,5-thiadiazole A solution of the crude (compound 12) (1.05 g, 0.0043 mol) in DMF (25 mL) was treated portionwise with freshly ground flaked $Na_2S-9H_2O$ (1.24 g, 0.0051 mol) . After 1 h, 1-bromo-3,3-dimethylbutane (1.18 g, 0.007 mol) was added and the reaction stirred overnight. The solvent was evaporated, the residue was acidified with 1N HCl, and the mixture extracted with ether. The aqueous was made basic and extracted with ether. The extracts were dried and the solvent evaporated to give a straw-colored liquid. The HCl salt (0.41 g) crystallized from $CHCl_3$—EtOAc-ether, m.p. 189°–190° C. (Compound 18).

EXAMPLE 19

(±)-3-(2-(2-Thienylthio)ethylthio)-4-(1-azabicyclo[2.2.2]octyl-3-oxy)-1,2,5-thiadiazole A solution of the crude (compound 12) (1.0 g, 0.0041 mol) in DMF (25 mL) was treated portionwise with freshly ground flaked $Na_2S-9H_2O$ (1.1 g, 0.0045 mol). After 1 h, 1-chloro-2-(2-thienylthio)ethane (1.1 g, 0.0062 mol) was added and the reaction stirred overnight. The solvent was evaporated, the residue was acidified with 1N HCl, and the mixture extracted with ether. The aqueous was made basic and extracted with ether. The extracts were dried, the solvent evaporated, and the residue purified by flash chromatography (10% EtOH-1% $NH_4OH$—$CHCl_3$) to give a liquid. The HCl salt (0.88 g) crystallized from ether, m.p. 179.5°–181° C. (Compound 19).

EXAMPLE 20

(±)-3-(2,2,3,3,3-Pentafluoropropylthio)-4-(1-azabicyclo-[2.2.2]octyl-3-oxy)-1,2,5-thiadiazole A solution of the crude (compound 12) (0.5 g, 0.002 mol) in DMF (15 mL) was treated portionwise with freshly ground flaked $Na_2S$-$9H_2O$ (0.53 g, 0.0022 mol). After 1 h, 1-methanesulfonoxy-2,2,3,3,3-pentafluoropropane (0.003 mol) was added and the reaction stirred overnight. The solvent was evaporated, the residue was acidified with 1N HCl, and the mixture extracted with ether. The aqueous was made basic and extracted with ether. The extracts were dried, the solvent evaporated, and the residue purified by flash chromatography (5% EtOH-0.5% $NH_4OH$—$CHCl_3$) to give a liquid. The HCl salt (0.016 g) crystallized from ether, m.p. 138°–140° C. (Compound 20).

EXAMPLE 21

(±)-3-(3-(2-Thienyl)propylthio)-4-(1-azabicyclo [2.2.2]octyl-3-oxy)-1,2,5-thiadiazole A solution of the crude (compound 12) (0.6 g, 0.0024 mol) in DMF (15 mL) was treated portionwise with freshly ground flaked $Na_2S$-$9H_2O$ (0.6 g, 0.0027 mol). After 1 h, 1-chloro-3-(2-thienyl)propane (0.6 g, 0.0036 mol) was added and the reaction stirred overnight. The solvent was evaporated, the residue was acidified with 1N HCl, and the mixture extracted with ether. The aqueous was made basic and extracted with ether. The extracts were dried, the solvent evaporated, and the residue purified by flash chromatography (10% EtOH-1% $NH_4OH$—$CHCl_3$) to give a liquid. The HCl salt (0.16 g) crystallized from EtOH—EtOAc, m.p. 194°–196° C. (Compound 21).

EXAMPLE 22

(±)-3-Butylthio-4-((1-azabicyclo[2.2.2]octan-3-yl)-methoxy)-1,2,5-thiadiazole

A solution of 3-hydroxymethyl-1-azabicyclo[2.2.2]octane (1.4 g, 0.01 mol) in THF (30 mL) was treated with 1.6M n-butyllithium in hexane (6.5 mL, 0.0104 mol). The mixture was cooled to 10° C., and 3-chloro-4-ethylsulfonyl-1,2,5-thiadiazole (2.21 g, 0.0104 mol) in THF (10 mL) was added dropwise. Cooling was removed and the reaction stirred overnight. The reaction was treated with $H_2O$, diluted with ether, and extracted with 1N HCl (25 mL). The acidic extracts were washed with ether, made basic, and extracted with ether. The extracts were dried and the solvent evaporated to give an orange liquid (1.82 g). The liquid was dissolved in DMF (32 mL) and treated with freshly ground flaked $Na_2S$-$9H_2O$ (2.5 g, 0.0104 mol) in portions. After 55 min, the reaction was treated with 1-iodobutane (2.6 g, 0.014 mol) and warmed to 44° C. overnight. The solvent was evaporated, the residue acidified with 1N HCl, and the mixture extracted with EtOAc-ether (1:1). The aqueous fraction was made basic and extracted with ether. The ether was dried, the solvent evaporated, and the residue purified by radial chromatography (5% EtOH-0.5% $NH_4OH$—$CHCl_3$) to give a liquid. The HCl salt (0.84 g) crystallized from EtOAc-ether, m.p. 170°–171° C. (Compound 22).

EXAMPLE 23

(±)-exo-3-Pentylthio-4-(1-azabicyclo[3.2.1]octyl-6-oxy)-1,2,5-thiadiazole and (±)-Endo-3-pentylthio-4-(1-azabicyclo[3.2.1]-octyl-6-oxy)-1,2,5-thiadiazole A solution of the endo/exo mixture of 1-azabicyclo[3.2.1] octan-6-ol (1.95 g, 0.0153 mol, ref. Sternbach, L. H.; Kaiser, S. J. Amer. Chem. Soc. 1952, 74, 2215–2218.) in THF (25 mL) was treated with 1.6M n-butyllithium in hexane (9.6 mL, 0.0153 mol). When the mixture had cooled to ambient temperature, 3-chloro-4-ethylsulfonyl-1,2,5-thiadiazole (2.96 g, 0.014 mol) in THF (15 mL) was added dropwise and the reaction stirred overnight. The reaction was treated with $H_2O$, diluted with ether, and extracted with 1N HCl (32 mL). The acidic extract was made basic, extracted with ether, the extracts dried, and the solvent evaporated to give an orange liquid (1.25 g). The liquid was dissolved in DMF (25 mL) and treated with freshly ground flaked $Na_2S$-$9H_2O$ (1.82 g, 0.0076 mol) in portions. After 40 min, 1-bromopentane (1.55 g, 0.0103 mol) was added and the reaction stirred overnight. The solvent was evaporated, the residue acidified, and the mixture extracted with ether. The aqueous fraction was made basic, extracted with ether, the extracts dried, and the solvent evaporated. The residue was purified by radial chromatography (2.5% EtOH-0.25% $NH_4OH$—$CHCl_3$) to first elute the exo isomer as a liquid. The HCl salt (0.26 g), crystallized from EtOAc, m.p. 159°–160° C. (Compound 23). Further elution provided the endo isomer as a liquid. The HCl salt (0.23 g) crystallized from EtOAc, m.p. 190°–193° C. (Compound 24).

EXAMPLE 24

(±)-endo-3-Butyloxy-4-(1-azabicyclo[2.2.1]heptyl-3-oxy)-1,2,5-thiadiazole

A solution of a mixture of (±)-endo and (±)-exo-1-azabicyclo[2.2.1]heptan3-ol (0.5 g, 0.0044 mol)(Ref. J. Org. Chem. 1969, 34, 3674–3676) in THF (20 mL) was cooled in an ice-water bath and treated dropwise with 1.6M n-butyllithium in hexane (2.8 mL, 0.0044 mol). Cooling was removed, 3-butyloxy-4-methanesulfonyl-1,2,5-thiadiazole (1.4 g, 0.0059 mol) was added, and the reaction heated to reflux for 6 h. The solvent was evaporated, the residue acidified with 1N HCl, and the mixture extracted with ether. The aqueous solution was made basic and extracted with EtOAc. The extracts were washed with $H_2O$, dried, and the solvent evaporated to give a clear oil. Radial chromatography (5% EtOH, 0.5% $NH_4OH$, $CHCl_3$) eluted the title compound as the more polar of the two UV active spots. The HCl salt of the title compound (0.5 g) crystallized from EtOAc with a quarter mole of $H_2O$, m.p. 161.5°–163° C. (Compound 25).

EXAMPLE 25

(±)-Exo-3-butyloxy-4-(1-azabicyclo[2.2.1]heptyl-3-oxy)-1,2,5-thiadiazole

Rechromatography of the mixed fractions from the isolation of (compound 25) (5% EtOH, 0.5% $NH_4OH$, $CHCl_3$) gave the less polar UV active material. The HCl salt (0.036 g) crystallized from EtOAc with a quarter mole of water, m.p. 156°–157° C. (Compound 26).

EXAMPLE 26

(±)-3-Butyloxy-4-(3-pyrrolidinyloxy)-1,2,5-thiadiazole

A suspension of NaH (0.066 g, 0.0028 mol) in THF (25 mL) was treated with 1-t-butylcarbamoyl-3-hydroxypyrrolidine (Ref. Syn. Commun. 15, 587.) (0.5 g, 0.0027 mol) and the reaction warmed to 50° C. for 30 min. After cooling to ambient temperature, 3-butyloxy-4-methanesulfonyl-1,2,5-thiadiazole (0.55 g, 0.0027 mol) in THF (5 mL) was added and the reaction heated to reflux for 2.5 h. The solvent was evaporated, the residue treated with ice-water, and the mixture extracted with ether. The extracts were washed with brine, dried, and the solvent evaporated. The residue was dissolved in ether (50 mL) and treated with a slow stream of HCl for 5 min. After stirring overnight, the reaction was extracted with cold water. The aqueous was washed with ether, made basic, and extracted with EtOAc. The extracts were washed with brine, dried, and the solvent evaporated to give a clear oil. The HCl salt (0.42 g) crystallized from EtOAc, m.p. 127°–128° C. (Compound 27).

EXAMPLE 27

(±)-3-Butyloxy-4-(1-methyl-3-pyrrolidinyloxy)-1,2,5-thiadiazole

A solution of 1-methyl-3-pyrrolidinol (0.6 g, 0.0059 mol) in THF (20 mL) was treated with 1.6M n-butyllithium in hexane (3.1 mL), 0.005 mol). To the solution was added 3-butyloxy-4-methanesulfonyl-1,2,5-thiadiazole (1.0 g, 0.0042 mol) and the reaction heated to reflux overnight. The solvent was evaporated, the residue acidified with cold 1N HCl, and the mixture extracted with ether. The aqueous fraction was made basic, extracted with EtOAc, and the extracts washed with water. The extracts were dried and the solvent evaporated to give a liquid. The HCl salt (0.7 g) crystallized from EtOAc, m.p. 157°–158° C. (Compound 28).

EXAMPLE 28

(±)-3-Butylthio-4-(1-methyl-3-piperidyloxy)-1,2,5-thiadiazole

A solution of 3-hydroxy-1-methylpiperidine (1.12 g, 0.0095 mol) in THF (25 mL) was treated with 1.6M n-butyllithium in hexane (5.9 mL, 0.0095 mol). The mixture was cooled to 8° C. and treated dropwise with 3-chloro-4-ethylsulfonyl-1,2,5-thiadiazole (1.83 g, 0.0086 mol) in THF (20 mL). The cooling was removed and the reaction stirred overnight. The mixture was treated with $H_2O$, acidified with 1N HCl and diluted with ether. The aqueous fraction was washed with ether, made basic, and extracted with ether. The extracts dried and solvent evaporated to give a brown liquid (1.95 g). The liquid was dissolved in DMF (38 mL) and treated with freshly ground flaked $Na_2S-9H_2O$ (2.98 g, 0.0124 mol) in portions. After 1 h, the mixture was treated with 1-iodobutane (3.1 g, 0.0169 mol) and stirred 64 h. The solvent was evaporated, the residue acidified with 1N HCl, and the mixture extracted with ether. The aqueous solution was made basic and extracted with ether. The extracts were dried and the solvent evaporated to give an orange liquid. Purification by radial chromatography (2.5% EtOH-0.25% $NH_4OH$—$CHCl_3$) gave a liquid whose HCl salt (1.4 g) crystallized from $CHCl_3$—EtOAc-ether, m.p. 141°–142° C. (Compound 29).

EXAMPLE 29

3-Butylthio-4-(1-methyl-4-piperidyloxy)-1,2,5-thiadiazole

A solution of 4-hydroxy-1-methylpiperidine (1.12 g, 0.0095 mol) in THF (25 mL) was treated with 1.6M n-butyllithium in hexane (5.9 mL, 0.0095 mol). The mixture was cooled to 8° C. and treated dropwise with 3-chloro-4-ethylsulfonyl-1,2,5-thiadiazole (1.83 g, 0.0086 mol) in THF (20 mL). The cooling was removed and the reaction stirred overnight. The mixture was treated with $H_2O$, acidified with 1N HCl, and diluted with ether. The aqueous fraction was washed with ether, made basic, and extracted with ether. The extracts dried and solvent evaporated to give a brown liquid (1.52 g). The liquid was dissolved in DMF (30 mL) and treated with freshly ground flaked $Na_2S-9H_2O$ (2.32 g, 0.0097 mol) in portions. After 50 min, the mixture was treated with 1-iodobutane (2.4 g, 0.013 mol) and stirred for 63 h. The solvent was evaporated, the residue acidified with dilute HCl, and the mixture extracted with ether. The aqueous fraction was made basic and extracted with ether. The extracts were dried and the solvent evaporated to give 1.3 g liquid. The HCl salt (1.3 g) crystallized from EtOAc-ether, m.p. 140°–142° C. (Compound 30).

EXAMPLE 30

(S)-3-Butyloxy-4-(1-methyl-2-pyrrolidinylmethoxy)-1,2,5-thiadiazole

A solution of (S)-1-methyl-2-pyrrolidinemethanol (0.86, 0.0075 mol) in THF (20 mL) was treated with 1.6M n-butyllithium in hexane (4.7 mL, 0.0075 mol). To the solution was added 3-butyloxy-4-methanesulfonyl-1,2,5-thiadiazole (1.2 g, 0.005 mol) and the reaction heated to reflux for 6.5 h. The solvent was evaporated, the residue acidified with cold 1N HCl, and the mixture extracted with ether. The aqueous was made basic and extracted with EtOAc. The extracts were washed with water, dried, and the solvent evaporated to give a liquid. The HCl salt (0.72 g) crystallized from EtOAc, m.p. 115°–116° C. (Compound 31).

EXAMPLE 31

(S)-3-Butyloxy-4-(2-pyrrolidinylmethoxy)-1,2,5-thiadiazole

A solution of (S)-1-butyloxycarbonyl-2-pyrrolidinemethanol (1.21, 0.006 mol) in THF (5 mL) was added to a suspension of 60% NaH in oil (0.24 g, 0.006 mol) in THF (30 mL). After 1 h, the mixture was heated to gentle reflux for 1 h. To the solution was added 3-butyloxy-4-methanesulfonyl-1,2,5-thiadiazole (1 g, 0.0042 mol) and the reaction heated to reflux overnight. The solvent was evaporated, the residue treated with cold $H_2O$, and the mixture extracted with EtOAc. The extracts were dried and treated with a stream of dry HCl for 3 min. After another hour, the solvent was evaporated, the residue treated with cold $H_2O$, and the mixture extracted with ether. The aqueous fraction was made basic and extracted with EtOAc. The extracts were washed with water, dried, and the solvent evaporated to give a liquid. The HCl salt (0.72 g) crystallized from EtOAc, m.p. 99°–100° C. (Compound 32).

EXAMPLE 32

3-Butyloxy-4-(2-(dimethylamino)ethoxy)-1,2,5-thiadiazole

A solution of 2-dimethylaminoethanol (0.67 g, 0.0075 mol) in THF (20 mL) was treated with 1.6M n-butyllithium in hexane (4.7 mL, 0.0075 mol). To the solution was added 3-butyloxy-4-methanesulfonyl-1,2,5-thiadiazole (1.2 g, 0.005 mol) and the reaction heated to reflux for 6 h. The solvent was evaporated, the residue acidified with cold 1N HCl, and the mixture extracted with ether. The aqueous was made basic and extracted with EtOAc. The extracts were

EXAMPLE 33

3-Butylthio-4-(2-(diethylamino)ethoxy)-1,2,5-thiadiazole

A solution of 2-diethylaminoethanol (1.11 g, 0.0095 mol) in THF (25 mL) was treated with 1.6M n-butyllithium in hexane (5.9 mL, 0.0095 mol). The mixture was cooled to 8° C. and treated dropwise with 3-chloro-4-ethylsulfonyl-1,2,5thiadiazole (1.83 g, 0.0086 mol) in THF (20 mL). The cooling was removed and the reaction stirred overnight. The mixture was treated with $H_2O$, acidified with 1N HCl, and diluted with ether. The aqueous fraction was washed with ether, made basic, and extracted with ether. The extracts dried and solvent evaporated to give a brown liquid (1.6 g). The liquid was dissolved in DMF (30 mL) and treated with freshly ground flaked $Na_2S-9H_2O$ (2.43 g, 0.010 mol) in portions. After 50 min, the mixture was treated with 1-iodobutane (2.52 g, 0.0137 mol) and stirred for 46 h. The solvent was evaporated, the residue acidified with dilute HCl, and the mixture extracted with ether. The aqueous fraction was made basic and extracted with ether. The extracts were dried, the solvent evaporated, and the residue purified by radial chromatography (5% EtOH-0.5% $NH_4OH$—$CHCl_3$) to give a liquid. The HCl salt (1.15 g) crystallized from EtOAc-ether, m.p. 95°–97° C. (Compound 34).

EXAMPLE 34

3-Butyloxy-4-(2-(trimethylamino)ethoxy)-1,2,5-thiadiazole iodide

A solution of (compound 33) (from 0.5 g, 0.0018 mol of the HCl salt) in EtOAc (30 mL) was treated with $CH_3I$ (0.3 mL) and stirred overnight. The precipitant was collected, washed with EtOAc, and dried to give a white solid (0.64 g), m.p. 137°–138° C. (Compound 35).

EXAMPLE 35

3-Butyloxy-4-(2-(dimethylamino)ethylthio)-1,2,5-thiadiazole

A suspension of 2-dimethylaminoethanthiol hydrochloride (0.57 g, 0.004 mol) in THF (25 mL) was treated with 1.6M n-butyllithium in hexane (5 mL, 0.008 mol). To the solution was added 3-butyloxy-4-methanesulfonyl-1,2,5-thiadiazole (0.71 g, 0.003 mol) and the reaction heated to reflux for 2 h followed by stirring at ambient temperature overnight. The solvent was evaporated, the residue acidified with cold 1N HCl, and the mixture extracted with ether. The aqueous was made basic and extracted with ether. The extracts were washed with water, dried, and the solvent evaporated. The residue was purified by radial chromatography (5% EtOH-0.5% $NH_4OH$—$CHCl_3$) to give a tan liquid. The HCl salt (0.22 g) recrystallized from EtOAc to give a white solid, m.p. 108°–109° C. (Compound 36).

EXAMPLE 36

3-Chloro-4-(1-propylthio)-1,2,5-thiadiazole

Cyanogen (34 g, 0.65 mol) was bubbled into ether (250 mL) maintained at −10° C. To the solution was added dropwise diethylamine (3 mL) followed by dropwise addition of 1-propanethiol (57 mL, 0.63 mol) in ether (25 mL) at such a rate that the temperature did not exceed −5° C. After 5 h, cooling was removed and the reaction stirred overnight. Ether was distilled from the reaction until the pot temperature reached 50° C. The reaction was cooled to ambient and added dropwise to a solution of sulfur monochloride (125 mL, 1.56 mol) in DMF (125 mL) that was cooled in an ice-water bath. Cooling was removed and the reaction allowed to exotherm to 35° C., recooled to below 30° C., then stirred overnight. The reaction was cooled in EtOH-ice and the excess sulfur monochloride carefully destroyed by dropwise addition of $H_2O$ (200 mL) such that the temperature did not exceed 30° C. The mixture was extracted with hexane, the extracts washed with brine, dried, and the solvent evaporated. The residue was distilled at 1.5 mm Hg to give a yellow liquid (98.6 g), b.p. 84°–94° C. (Compound 37).

EXAMPLE 37

(R)-3-Pentylthio-4-(1-azabicyclo[2.2.2]octyl-3-oxy)-1,2,5-thiadiazole

A solution of (R)-1-azabicyclo[2.2.2]octan-3-ol (3.0 g, 0.0236 mol) in THF (40 mL) was cooled to 10° C. as 1.6M n-butyllithium in hexane (15 mL, 0.024 mol) was added dropwise. The resulting mixture was treated with 3-chloro-4-ethylsulfonyl-1,2,5-thiadiazole (5.01 g, 0.0236 mol) in THF (5 mL) and stirred for 22 h. The reaction was treated with $H_2O$ (10 mL), ether (170 mL) and extracted with 1N HCl (35 mL). The aqueous fraction was washed with ether, made basic, and extracted with ether. The extracts were dried and the solvent evaporated to give an oil (2.35 g). The oil was dissolved in DMF (35 mL), treated portionwise with freshly ground flaked $Na_2S-9H_2O$ (2.53 g, 0.0105 mol), and heated (40° C). After 1.25 h, 1-bromopentane (2.18 g, 0.0145 mol) was added and the reaction stirred overnight at 38° C. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (5% EtOH-0.5% $NH_4OH$—$CHCl_3$), The HCl salt (1.68 g) crystallized from $CHCl_3$—EtOAc, m.p. 195°–196° C., $[\alpha]_D$=−24.6° (EtOH) (Compound 38).

EXAMPLE 38

(±)-3-(4-Methylpentylthio)-4-(1-azabicyclo[2.2.2]octyl-3-oxy)-1,2,5-thiadiazole A solution of the crude (compound 12) (1.65 g, 0.0067 mol) in DMF (25 mL) was treated portionwise with freshly ground flaked $Na_2S-9H_2O$ (1.83 g, 0.0076 mol). After 1 h, 1-bromo-4-methylpentane (1.73 g, 0.0105 mol) was added and the reaction stirred three days at 40° C. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (5% EtOH-0.5% $NH_4OH$—$CHCl_3$). The HCl salt (0.74 g) crystallized from $CHCl_3$—EtOAc-ether, m.p. 183°–185° C. (Compound 39).

EXAMPLE 39

(±)-3-(3-Phenylpropylthio)-4-(1-azabicyclo[2.2.2]octyl-3-oxy)-1,2,5-thiadiazole A solution of the crude (compound 12) (0.9 g, 0.0037 mol) in DMF (25 mL) was treated portionwise with freshly ground flaked Na$_2$S-9H$_2$O (0.97 g, 0.004 mol). After 1 h, 1-bromo-3-phenylpropane (1.11 g, 0.056 mol) was added and the reaction stirred 17 h at 50° C. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (2.5% EtOH-0.25% NH$_4$OH—CHCl$_3$). The HCl salt (0.42 g) crystallized from CHCl$_3$—EtOAc-ether, m.p. 210°–212° C. (Compound 40).

EXAMPLE 40

(±)-3-(4-Cyanobenzylthio)-4-(1-azabicyclo[2.2.2]octyl-3-oxy)-1,2 5-thiadiazole

A solution of the crude (compound 12) (1.15 g, 0.0047 mol) in DMF (25 mL) was treated portionwise with freshly ground flaked Na$_2$S-9H$_2$O (1.68 g, 0.007 mol). After 1 h, 4-cyanobenzyl bromide (1.85 g, 0.094 mol) was added and the reaction stirred 22 h. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (5% EtOH-0.5% NH$_4$OH—CHCl$_3$). The HCl salt (0.12 g) crystallized from CHCl$_3$—EtOAc-ether, m.p. 211°–213° C. (Compound 41).

EXAMPLE 41

(±)-3-(4-Fluorobenzylthio)-4-(1-azabicyclo[2.2.2]octyl-3-oxy)-1,2,5-thiadiazole

A solution of the crude (compound 12) (1.15 g, 0.0047 mol) in DMF (25 mL) was treated portionwise with freshly ground flaked Na$_2$S-9H$_2$O (1.68 g, 0.007 mol). After 1 h, 4-fluorobenzyl chloride (1.37 g, 0.094 mol) was added and the reaction stirred 22 h. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (5% EtOH-0.5% NH$_4$OH—CHCl$_3$). The HCl salt (0.89 g) crystallized from MeOH—EtOAc-ether, m.p. 236°–237° C. (Compound 42).

EXAMPLE 42

(±)-3-(2-Phenylethylthio)-4-(1-azabicyclo[2.2.2]octyl-3-oxy)-1,2,5-thiadiazole

A solution of the crude (compound 12) (1.15 g, 0.0047 mol) in DMF (25 mL) was treated portionwise with freshly ground flaked Na$_2$S-9H$_2$O (1.68 g, 0.007 mol). After 1 h, the reaction was cooled to −30° C. and treated with dropwise with 1-bromo-2-phenylethane (1.75 g, 0.095 mol) in DMF (22 mL). The cooling was removed after 1 h and the reaction stirred 22 h. The solvent was evaporated, the residue was acidified with 1N HCl, and the mixture extracted with ether. The aqueous was made basic and extracted with ether. The extracts were dried and the solvent evaporated to give a straw-colored liquid that was purified by radial chromatography (5% EtOH-0.5% NH$_4$OH—CHCl$_3$). The HCl salt (0.53 g) crystallized from MeOH—EtOAc-ether, m.p. 181°–183° C. (Compound 43).

EXAMPLE 43

(±)-3-(2-Phenyloxyethylthio)-4-(1-azabicyclo[2.2.2]octyl-3-oxy)-1,2,5-thiadiazole A solution of the crude (compound 12) (1.15 g, 0.0047 mol) in DMF (25 mL) was treated portionwise with freshly ground flaked Na$_2$S-9H$_2$O (1.68 g, 0.007 mol). After 1 h, the reaction was cooled to −50° C. and treated with dropwise with 1-bromo-2-phenyloxyethane (1.90 g, 0.0095 mol) in DMF (22 mL). The cooling was removed after 1 h and the reaction stirred 22 h. Another solution of bromo-2-phenyloxyethane (1.90 g, 0.0095 mol) in DMF (5 mL) was added in two portions with cooling to −30° C. After 2 h, the solvent was evaporated, the residue was acidified with 1N HCl, and the mixture extracted with ether. The aqueous was made basic and extracted with CHCl$_3$. The extracts were dried and the solvent evaporated to give a straw-colored liquid that was purified by radial chromatography (5% EtOH-0.5% NH$_4$OH—CHCl$_3$). The HCl salt (1.29 g) crystallized from MeOH—EtOAc-ether, m.p. 193°–194° C. (Compound 44).

EXAMPLE 44 endo-3-Butyloxy-4-(N-methyl-8-azabicyclo[3.2.1]octyl-3-oxy)-1,2,5-thiadiazole

A solution of tropine (1.36 g, 0.0094 mol) in THF (25 mL) was treated dropwise with 1.6M n-butyllithium in hexane (5.9 mL, 0.00095 mol). To this solution was added 3-butyloxy-4-methanesulfonyl-1,2,5-thiadiazole (2.04 g, 0.0086 mol) in THF (25 mL) and the reaction heated to 40° C. for 19 h. The solution was treated with H$_2$O (40 mL), 5N HCl (5.5 mL), and ether (150 mL), the aqueous layer separated and made basic. The aqueous solution was extracted with ether, the extracts dried, and the solvent evaporated to give a clear oil. The oil was purified by radial chromatography (5% EtOH-0.5% NH$_4$OH—CHCl$_3$) and the HCl salt (1.49 g) crystallized from CHCl$_3$—EtOAc-ether, m.p. 168°–169° C. (Compound 45).

EXAMPLE 45

(±)-exo-3-Butyloxy-4-(6-(N-methyl-8-azabicyclo[3.2.1]octan-3-onoxy))-1,2,5-thiadiazole A suspension of NaH (0.11 g, 0.00275 mol) in THF (25 mL) was treated with (±)-exo-6-hydroxytropinone (1.36 g, 0.0094 mol) and the reaction heated to 50° C. for 1 h. To this solution was added 3-butyloxy-4-methanesulfonyl-1,2,5-thiadiazole (0.55 g, 0.0027 mol) and the reaction heated to reflux for 2 h. The solvent was evaporated, the residue suspended in ice-water, acidified, and the mixture extracted with ether. The aqueous layer was made basic, was extracted with ether, the extracts washed with brine, dried, and the solvent evaporated to give a clear oil. The oil was purified by radial chromatography (2.5% EtOH-0.25% NH$_4$OH—CHCl$_3$) and the HCl salt (0.325 g) crystallized from EtOAc, m.p. 178°–179° C. (Compound 46).

EXAMPLE 46

(±)-exo-3-Chloro-4-(1-azabicyclo[3.2.1]octyl-6-oxy)-1,2,5-thiadiazole and (±)-endo-3-Chloro-4-(1-azabicyclo [3.2.1]octyl-6-oxy)-1,2,5-thiadiazole A solution of the endo/exo mixture of 1-azabicyclo[3.2.1]octan-6-ol (13 g, 0.102 mol, ref. Sternbach, L. H.; Kaiser, S. J. Amer. Chem. Soc. 1952, 74, 2215–2218), triethylamine (0.3 mL), and CHCl$_3$ (100 mL) was cooled to 3° C. and cyanogen (7.7 g, 0.148 mol) bubbled into the solution. After 1 h, the cooling was removed, the reaction stirred another 3 h, and the solvent evaporated. The residue was dissolved in DMF (30 mL) and added dropwise to a solution of S$_2$Cl$_2$ (47.3 g, 0.35 mol) in DMF (30 mL) that was cooled in an ice-water bath. Cooling was removed, the reaction stirred overnight, and, after further cooling, the excess $S_2Cl_2$ carefully destroyed with $H_2O$. The mixture was diluted with $H_2O$ (200 mL), the aqueous solution decanted, and the sulfur residue triturated with $H_2O$. The combined aqueous solutions were evaporated to a small volume (150 mL) and extracted with hexane. The aqueous solution was cooled, made basic with 50% NaOH, and extracted with $CHCl_3$. The extracts were dried, the solvent thoroughly evaporated, the residue suspended in ether and filtered. Evaporation of the solvent gave a brown liquid (12.76 g), a 0.8 g sample of which was purified by radial chromatography (10% EtOH-1% $NH_4OH$—$CHCl_3$). The exo isomer eluted first and was converted to an HCl salt (0.1 g) that crystallized from acetone, m.p. 226° C., dec. (compound 47). Further elution provided the endo isomer that crystallized as an HCl salt (0.2 g) from 2-propanol, m.p. 199.5°–201° C. (Compound 48).

EXAMPLE 47

(±)-endo-3-(4-cyanobenzylthio)-4-(1-azabicyclo [3.2.1]octyl-6-oxy)-1,2,5-thiadiazole A solution of the crude mixture of (compound 47) and (compound 48) (2.3 g, 0.0094 mol) in DMF (34 mL) was treated portionwise with freshly ground flaked $Na_2S$-$9H_2O$ (3.36 g, 0.014 mol). After 2 h, the reaction was cooled to −30° C. and treated with dropwise with 4-cyanobenzyl bromide (3.7 g, 0.0189 mol) in DMF (34 mL). The cooling was removed and after 1.5 h, the reaction was treated with 5N NaOH (4 mL). The solvents were evaporated, the residue dissolved in a mixture of $CHCl_3$ and $H_2O$, the $CHCl_3$ extract separated, and washed with $H_2O$. The organic extracts were dried, the solvent evaporated, and the residue purified by radial chromatography (5% EtOH-0.5% $NH_4OH$—EtOAc) to give the endo isomer. The HCl salt (0.31 g) crystallized from MeOH—EtOAc-ether, m.p. 250°–251° C. (Compound 49).

EXAMPLE 48

3-Butyloxy-4-(3-azetidinyloxy)-1,2,5-thiadiazole

A suspension of NaH (0.24 g, 0.006 mol) in THF (30 mL) was treated with 1-t-butylcarbamoyl-3-hydroxyazetidine (1.1 g, 0.006 mol), the reaction stirred 1 h, followed by addition of 3-butyloxy-4-methanesulfonyl-1,2,5-thiadiazole (1.0 g, 0.0042 mol) in THF (5 mL). The reaction was heated to reflux for 4 h, the solvent evaporated, the residue treated with ice-water, and the mixture extracted with EtOAc. The extracts were dried and treated with a slow stream of HCl for 3 min. After 0.5 h, the solvent was evaporated, the residue treated with ice-water, and the solution extracted with ether. The aqueous phase was made basic, extracted with EtOAc, the extracts washed with brine, dried, and the solvent evaporated to give a clear oil. The HCl salt (0.77 g) crystallized from 2-propanol, m.p. 167°–168.5° C. (Compound 50).

EXAMPLE 49

3-Butylthio-4-(3-azetidinyloxy)-1,2,5-thiadiazole

A suspension of NaH (0.24 g, 0.006 mol) in THF (30 mL) was treated with 1-t-butylcarbamoyl-3-hydroxyazetidine (1.6 g, 0.0092 mol), and the reaction stirred 1 h. After cooling to 8° C., 3-chloro-4-ethylsulfonyl-1,2,5-thiadiazole (1.96 g, 0.0092 mol) in THF (5 mL) was added, the reaction stirred 30 min, cooling removed for 30 min, and the reaction heated to 35° C. for 45 min. Heating was removed, the reaction stirred overnight, and the solvent evaporated. The residue was suspended in cold water, the mixture extracted with EtOAc, the extracts washed with brine, dried, and the solvent evaporated to give a tan liquid, (2.98 g). A DMF (30 mL) solution of the liquid was treated with freshly ground flaked $Na_2S$-$9H_2O$ (3.3 g, 0.0138 mol). After 1 h, 1-iodobutane (2.1 mL) was added, the reaction stirred 2 h, diluted with cold water, and extracted with ether. The ether was dried, the solvent evaporated, the residue dissolved in EtOAc, and the solution treated with a stream of dry HCl for 5 min. After 1 h, the reaction was treated with icewater and the organic solvent evaporated. The aqueous solution was extracted with ether, made basic, and extracted with EtOAc. The EtOAc extracts were dried and the solvent evaporated to give a tan liquid that was purified by radial chromatography (10% EtOH-1% $NH_4OH$—$CHCl_3$). The HCl salt (0.41 g) crystallized from EtOAc, m.p. 138°–139° C. (Compound 51).

EXAMPLE 50

(±)-trans-3-Butyloxy-4-(2-dimethylaminocyclopentyloxy)-1,2,5-thiadiazole

A suspension of NaH (0.25 g, 0.006 mol) in THF (30 mL) was treated with (±)-trans-dimethylaminocyclopentanol (0.8 g, 0.006 mol), the reaction heated to reflux 1 h, followed by addition of 3-butyloxy-4-methanesulfonyl-1,2,5-thiadiazole (1.0 g, 0.0042 mol), and the heating continued overnight. The solvent was evaporated, the residue suspended in cold water, and the mixture acidified. The solution was extracted with ether, made basic, and extracted with EtOAc. The EtOAc extracts were washed with brine, dried, the solvent evaporated, and the residue purified by radial chromatography (10% EtOH-1% $NH_4OH$—$CHCl_3$). The HCl salt (0.98 g) crystallized from EtOAc, m.p. 148°–149° C. (Compound 52).

EXAMPLE 51

(±)-3-Butylthio-4-(3-pyrrolidinyloxy)-1,2,5-thiadiazole

A suspension of NaH (0.22 g, 0.009 mol) in THF (30 mL) was treated with (±)-1-t-butylcarbamoyl-3-hydroxypyrrolidine (1.73 g, 0.0092 mol), and the reaction heated to reflux for 35 min. After cooling to 10° C., 3-chloro-4-ethylsulfonyl-1,2,5-thiadiazole (1.96 g, 0.0092 mol) in THF (5 mL) was added, cooling was removed, and the reaction heated to 35° C. for 16 h. The reaction was diluted with $H_2O$, ether added, and the ether extract separated. The ether extract was washed with $H_2O$, dried, and the solvent evaporated to give a tan liquid, (3.05 g). A DMF (42 mL) solution of the liquid was treated with freshly ground flaked $Na_2S$-$9H_2O$ (3.3 g, 0.0138 mol). After 1 h, 1-iodobutane (3.42 g, 0.0186 mol) was added, and the reaction stirred at 40° C. for 16 h. The solvent was evaporated, the residue diluted with cold water, and the mixture extracted with ether. The ether was dried, the solvent evaporated, the residue dissolved in ether, and the solution treated with a stream of dry HCl for 5 min. After 66 h, the reaction was treated with ice-water and the organic solvent evaporated. The aqueous solution was extracted with ether, made basic, and extracted with ether. The ether extracts were dried and the solvent evaporated to give a tan liquid that was purified by radial chromatography (5% EtOH-0.5% $NH_4OH$—$CHCl_3$). The HCl salt (0.67 g) crystallized from EtOAc, m.p. 99°–100.5° C. (Compound 53).

EXAMPLE 52

1-Chloro-2-(2-thio-5-trifluoromethylthienyl)ethane

A solution of 2-trifluoromethylthiophene (1.2 g, 0.0105 mol, J. Fluorine Chem. 1990, 46, 445–459) in THF (10 mL) was cooled to −40° C. as 1.6M n-butyllithium in hexane (6.5 mL, 0.0103 mol) was added dropwise. After 2 h, the reaction was cooled to −78° C. and S (0.32 g, 0.01 mol) was added and the reaction stirred 2 h. Cooling was removed and when temperature reached 0° C., the reaction was quenched with $H_2O$ and dilute NaOH. The mixture was extracted with ether, the aqueous phase acidified, and the mixture extracted with ether. The final ether extracts were dried and the solvent evaporated to give 2 g of material. This was added to a mixture of KOH (0.6 g, 0.011 mol), N(butyl)$_4$HSO$_4$ (0.3 g, 0.001 mol), and 1-bromo-2-chloroethane (1.4 g, 0.01 mol) in THF (20 mL) and the reaction stirred at ambient overnight. The mixture was poured into $H_2O$, extracted with $CH_2Cl_2$, the extracts dried, and the solvent evaporated. The residue was purified by flash chromatography (5% EtOAc-hexane) to give a liquid (0.42 g). (Compound 54).

EXAMPLE 53

(±)-3-(2-(2-Thio-5-trifluoromethylthienyl)ethylthio)-4-(1-azabicyclo[2.2.2]octyl-3-oxy)-1,2,5-thiadiazole A solution of the crude (compound 12) (0.37 g, 0.0015 mol) in DMF (8 mL) was treated portionwise with freshly ground flaked Na$_2$S-9H$_2$O (0.41 g, 0.0017 mol). After 1 h, 1-chloro-2-(2-thio-5-trifluoromethylthienyl) ethane (0.42 g, 0.0017 mol) was added and the reaction stirred overnight. The solvent was evaporated, the residue was acidified with 1N HCl, and the mixture extracted with ether. The aqueous was made basic and extracted with ether. The extracts were dried, the solvent evaporated, and the residue purified by radial chromatography (10% EtOH-1% NH$_4$OH—CHCl$_3$) to give a liquid. The oxalate salt (0.107 g) crystallized from 2-propanol, m.p. 65°–69° C. (Compound 55).

EXAMPLE 54

2-(5-(2-Thienyl)thiophene)thiol

A solution of 2-(2-thienyl)thiophene (10 g, 0.0602 mol) in THF (50 mL) was cooled to −40° C. as 1.6M n-butyllithium in hexane (37.2 mL, 0.0595 mol) was added dropwise. After 2 h, the reaction was cooled to −78° C. and S (1.8 g, 0.0575 mol) was added and the reaction stirred 2 h. Cooling was removed and when temperature reached 0° C., the reaction was quenched with $H_2O$ and dilute NaOH. The mixture was extracted with ether, the aqueous phase acidified, and the mixture extracted with ether. The final ether extracts were dried and the solvent evaporated to give 9.9 g of material. (Compound 56).

EXAMPLE 55

(±)-3-(2-(5-(2-Thienyl)thienyl)thio)-4-(1-azabicyclo[2.2.2]octyl-3-oxy)-1,2,5-thiadiazole A mixture of 2-(5-(2-thienyl)thiophene)thiol (1.2 g, 0.0061 mol), potassium t-butoxide (0.5 g, 0.0045 mol), and a trace of 18-Crown-6 in THF (90 mL) was stirred for 1.5 h. To the solution was added (compound 12) (1.0 g, 0.0041 mol) and the reaction heated to reflux overnight. The reaction was poured into $H_2O$, extracted with ether, the extracts dried, and the solvent evaporated. The residue was purified by flash chromatography (5% EtOH-0.5% NH$_4$OH—CHCl$_3$) and the oxalate salt (0.41 g) crystallized from acetone, m.p. 215° C., dec. (Compound 57).

EXAMPLE 56

1-Chloro-2-(2-(5-(2-thienyl)thienyl)thio)ethane

Crude 2-(5-(2-thienyl)thiophene)thiol (3 g, 0.0152 mol) was added to a mixture of KOH (0.93 g, 0.0166 mol), N(butyl)$_4$HSO$_4$ (0.51 g, 0.0015 mol), and 1-bromo-2-chloroethane (2.2 g, 0.0152 mol) in THF (100 mL) and the reaction stirred at ambient overnight. The mixture was poured into $H_2O$, extracted with $CH_2Cl_2$, the extracts dried, and the solvent evaporated to give the desired product (3.5 g). (Compound 58).

EXAMPLE 57

(±)-3-(2-(2-(5-(2-Thienyl)thienyl)thio)ethylthio)-4-(1-azabicyclo[2.2.2]octyl-3-oxy)-1,2,5-thiadiazole A solution of the crude (compound 12) (0.5 g, 0.002 mol) in DMF (10 mL) was treated portionwise with freshly ground flaked Na$_2$S-9H$_2$O (0.55 g, 0.0023 mol). After 1 h, 1-chloro-2-(2-(5-(2-thienyl)thienyl)thio)ethane (0.6 g, 0.0023 mol) was added and the reaction stirred overnight. The solvent was evaporated, the residue was acidified with 1N HCl, and the mixture extracted with ether. The aqueous was made basic and extracted with ether. The extracts were dried, the solvent evaporated, and the residue purified by flash chromatography (5% EtOH-0.5% NH$_4$OH—CHCl$_3$) to give a liquid. The oxalate salt (0.43 g) crystallized from acetone, m.p. 102°–105° C. (Compound 59).

EXAMPLE 58

(±)-3-(2-Thienyl)thio)-4-(1-azabicyclo[2.2.2]octyl-3-oxy)-1,2,5-thiadiazole

A mixture of 2-thiophenethiol (0.42 g, 0.0036 mol) and K$_2$CO$_3$ (0.59 g, 0.0043 mol), in DMF (20 mL) was heated at 60° C. for 3 h. To the solution was added (compound 12) (0.89 g, 0.0036 mol) and the reaction heated overnight. The reaction was poured into 1N HCl (50 mL), extracted with ether, the aqueous phase made basic, and the mixture extracted with EtOAc. The EtOAc extracts were dried, the solvent evaporated, and the residue purified by flash chromatography (5% EtOH-0.5% NH$_4$OH—CHCl$_3$). The oxalate salt (0.095 g) crystallized from acetone, m.p. 133°–136° C. (Compound 60).

EXAMPLE 59

(±)-3-(3-N-(2-Thiazolidonyl)propylthio)-4-(1-azabicyclo[2.2.2]octyl-3-oxy)1,2,5-thiadiazole A solution of the crude (compound 12) (0.5 g, 0.002 mol) in DMF (10 mL) was treated portionwise with freshly ground flaked Na$_2$S-9H$_2$O (0.55 g, 0.0023 mol). After 1 h, 1-chloro-3-N-(2-thiazolidone) propane (0.41 g, 0.0023 mol) was added and the reaction stirred overnight. The solvent was evaporated, the residue was acidified with 1N HCl, and the mixture extracted with ether. The aqueous was made basic and extracted with ether. The extracts were dried, the solvent evaporated, and the residue purified by radial chromatography (10% EtOH-1% NH$_4$OH—CHCl$_3$) to give a liquid. The oxalate salt (0.148 g) crystallized from acetone-ether, m.p. 70°–75° C. (Compound 61).

EXAMPLE 60

(±)exo-Methyl-7-hydroxy-2-azabicyclo[2.2.2]oct-5-ene-2-carboxylate

A solution of 2.1 g (8.4 mmol) methyl 7-acetoxy-7-cyano-2-azabicyclo[2.2.2]oct-5-ene-2-carboxylate (J. Org. Chem.

1989, 54, 2893) in 25 mL ethanol and 5 mL $H_2O$ was cooled in an ice bath. To this mixture was added 2.4 g (42 mmol) KOH followed by 0.65 g (17 mmol) $NaBH_4$. After 15 min. the ice bath was removed and the reaction was stirred for 16 h. The reaction was quenched by addition of 25 mL $H_2O$ and then concentrated under vacuum. To the residue was added 25 mL $H_2O$ and the mixture was extracted three times with 50 mL portions of EtOAc. The combined extracts were dried over $NaCl/Na_2SO_4$ and evaporated under vacuum. The residue was chromatographed (25% EtOAc/hexane) on silica gel to give 1.47 g of exo methyl 7-hydroxy-2-azabicyclo[2.2.2]oct-5-ene-2-carboxylate and 135 mg of endo methyl 7-hydroxy-2-azabicyclo[2.2.2]oct-5-ene-2-carboxylate. (Compound 62).

EXAMPLE 61

(±)exo-Methyl-6-hydroxy-2-azabicyclo[2.2.2]octane-2-carboxylate

A solution of 1.47 g (8 mmol) exo methyl 7-hydroxy-2-azabicyclo[2.2.2]oct-5-ene-2-carboxylate and 0.15 g 5% Pd/C in 50 mL methanol was hydrogenated at 50 psi on a Parr shaker for 5 h at room temperature. Removal of the catalyst by filtration followed by evaporation under vacuum afforded 1.43 g. (Compound 63).

EXAMPLE 62

(±)3-Butylthio-4-(exo-2-methoxycarbonyl-2-azabicyclo[2.2.2]oct-6-yloxy)-1,2,5-thiadiazole To a solution of 1.3 g (7.1 mmol) exo methyl 6-hydroxy-2-azabicyclo[2.2.2]octane-2-carboxylate and 0.80 g (7.1 mmol) potassium t-butoxide in 20 mL of THF was added 1.5 9 (7.1 mmol) 3-chloro-4-butylthio-1,2,5-thiadiazole. After stirring the mixture at room temperature for 20 h, 50 mL of brine was added and the solution was extracted five times with 50 mL portions of EtOAc. The combined extracts were dried over $NaCl/Na_2SO_4$ and evaporated under vacuum. Chromatography over silica gel (25% EtOAc/hexane) afforded 1.42 g. (Compound 64).

EXAMPLE 63

(±) 3-Butylthio-4-(exo-2-azabicyclo[2.2.2]oct-6-yloxy)-1,2,5-thiadiazole

Trimethylsilyliodide 0.70 mL (4.9 mmol) was added to a solution of 3-butylthio-4-(exo-2-methoxycarbonyl-2-azabicyclo[2.2.2]oct-6-yloxy)-1,2,5-thiadiazole in 10 mL of $CH_2Cl_2$. After stirring for 5 h at room temperature, the solution was evaporated under vacuum. 10 mL of saturated $NaHCO_3$ was added and the solution was extracted three times with 20 mL portions of EtOAc. The combined extracts were dried over $NaCl/Na_2SO_4$ and evaporated under vacuum. The residue was chromatographed over silica gel (10% EtOH, 1% $NH_4OH$—$CHCl_3$) and the resulting oil converted to its oxalate salt. Recrystallization from EtOH/EtOAc afforded 789 mg (mp. 148°–150° C.). (Compound 65).

EXAMPLE 64

3-Amino-4-butylthio-1,2,5-thiadiazole

A 1.04 g sample of 3-chloro-4-butylthio-1,2,5-thiadiazole was dissolved in 20 mL of THF and added to a 50 mL reaction vessel. The mixture was cooled to 0° C. A 10 mL sample of sodium bis(trimethylsilyl)amide in THF (1.0M) was added dropwise to the reaction vessel. The mixture was stirred at 0° C. The reaction was quenched using 50 mL water upon desired completion of reaction. The pH of the mixture was adjusted to 2.0 using HCl. The mixture was stirred for 15 min. and then adjusted to pH=11 using NaOH. The mixture was extracted using ether. The organic layers were combined, dried, and filtered. The filtrate was concentrated to dryness. The resulting product was purified using column chromatography. Yield: 1.07 g (65%). The N,N-bis (trimethylsilyl)-3-amino-4-butylthio-1,2,5-thiadiazole was suspended in 3N HCl and heated to about 50° C. The mixture was stirred for 3 h. The pH was adjusted to 11 using NaOH. The mixture was extracted using t-butylmethyl ester. The organics were combined, dried, filtered and concentrated to dryness. Yield: 0.43 g (45%). (Compound 66). The process substantially as described was repeated to yield 82% of the desired 3-amino-4-butylthio-1,2,5-thiadiazole.

EXAMPLE 65

3-Bromo-4-butylthio-1,2,5-thiadiazole

A 0.42 g sample of cupric bromide, 0.28 isoamyl nitrite and 6 mL acetonitrile were added to a 25 mL reaction vessel. The mixture was warmed to 65° C. The acetonitrile mixture was added to a 4 mL acetonitrile solution containing 0.30 g 4-amino-3-butylthio-1,2,5-thiadiazole. The mixture was stirred for 30 min. at 65°. The mixture was cooled to room temperature and quenched with 50 mL of 1N HCl. The organic layers were combined, dried, filtered and concentrated to dryness. Yield: 0.38 g (94%). The resulting material was purified using column chromatography to yield 0.30 g (73%) of material. (Compound 67).

The process substantially as described above was completed using copper(I) iodide (0.61 9) to provide 3-iodo-4-butylthio-1,2,5-thiadiazole. Yield: 0.23 g (48%). (Compound 68).

EXAMPLE 66

(±)3-(2,2,3,3,4,4,4-heptafluorobutyloxy)-4-[-3-(1-azabicyclo[2.2.2]octyloxy)]-1,2,5-thiadiazole A solution of potassium t-butoxide (1.6 g, 0.0143 mol) in THF (12 mL) was treated with 2,2,3,3,4,4,4-heptafluorobutanol (2 mL, 0.016 mol). After 5 min, Compound 12 (0.75 g, 0.003 mol) was added, the reaction stirred 2 h followed by heating to reflux for 1.5 h. After stirring at ambient temperature overnight and heating to reflux for another 1.5 h, the solvent was evaporated, the residue suspended in $H_2O$, and the mixture extracted with EtOAc. The extracts were dried, the solvent evaporated, and the residue purified by radial chromatography (20% EtOH-2% $NH_4OH$—$CHCl_3$) to give an oil. The hydrochloride salt crystallized from EtOAc with a half mole of $H_2O$ as a flocculent white solid (0.43 g), m.p. 168.5°–169.5° C. (Compound 69).

EXAMPLE 67

(±)3-(1-Butylthio)-4-[endo--6-(1-azabicyclo[3,2,1]octyloxy)]-1,2,5-thiadiazole

A solution of potassium t-butoxide (0.62 g, 0.0055 mol) in THF (12 mL) was treated with endo-1-azabicyclo[3.2.1]octan-6-ol (0.64 g, 0.005 mol). After 5 min, 3-chloro-4-(1-butylthio)-1,2,5-thiadiazole (1.2 g, 0.0057 mol) was added. After stirring overnight, the solvent was evaporated, the residue diluted with $H_2O$, acidified, and extracted with ether.

The aqueous phase was made basic and extracted with EtOAc, the extracts dried, washed with brine, dried, and the solvent evaporated. The residue was purified by radial chromatography (20% EtOH-2% NH$_4$OH—CHCl$_3$). The HCl salt crystallized from EtoAc to give a white solid (0.68 g), m.p. 201°–202° C. dec. (Compound 70).

EXAMPLE 68

(±)3-(3-Phenylpropylthio)-4-[endo--6-(1-azabicyclo [3.2.1]octyloxy)]-1,2,5-thiadiazole A solution of Compound 48 (0.9 g, 0.0037 mol) in DMF (25 mL) was treated portionwise with freshly ground flaked Na$_2$S-9H$_2$O (0.97 g, 0.004 mol). After 2 h, the reaction was treated with dropwise with 1-bromo-3-phenylpropane (1.11 g, 0.0059 mol), the reaction stirred 3.25 h, followed by dropwise addition of additional 1-bromo-3-phenylpropane (1.11 g, 0.0059 mol) in DMF (5 mL). After stirring overnight, the solvents were evaporated, the residue suspended in H$_2$O, acidified, and the mixture extracted with ether. The aqueous phase was made basic, extracted with CHCl$_3$, the extracts dried, and the solvent evaporated. The residue purified by radial chromatography (MeOH:EtOAc:NH$_4$OH/15:30:1) to give an oil. The HCl salt (0.41 g) crystallized from CHCl$_3$-EtOAc-ether, m.p. 178°–179° C. (Compound 72)

EXAMPLE 69

(±)3-[3-(4-Fluorophenyl)propylthio]-4-[-3-(1-azabicyclo[2.2.2]octyloxy)]-1,2,5-thiadiazole A solution of the crude Compound 12 (1.15 g, 0.0047 mol) in DMF (20 mL) was treated portionwise with freshly ground flaked Na$_2$S-9H$_2$O (1.68 g, 0.007 mol). After 1 h, 1-chloro-3-(4-fluorophenyl)propane (1.63 g, 0.0095 mol) in DMF (2 mL) was added dropwise and the reaction stirred 2.5 days. The reaction was then treated with additional 1-chloro-3-(4-fluorophenyl)propane (0.815 g, 0.0047 mol) and warmed at 35° C. for 6 h. The solvent was evaporated, the residue was acidified with 1N HCl, and the mixture extracted with ether. The aqueous was made basic and extracted with ether. The extracts were dried, the solvent evaporated, and the residue purified by radial chromatography (MeOH:EtOAc:NH$_4$OH/15:30:1). The HCl salt (0.19 g) crystallized from CHCl$_3$—EtOAc-ether, m.p. 189°–191° C. (Compound 73)

EXAMPLE 70

(±)3-{3-[4-(Trifluoromethyl)phenyl]propylthio}-4-[-3-(1-azabicyclo[2.2.2]octyloxy)]-1,2,5-thiadiazole A solution of the Compound 12 (1.15 g, 0.0047 mol) in DMF (20 mL) was treated portionwise with freshly ground flaked Na$_2$S-9H$_2$O (1.68 g, 0.007 mol). After 2 h, the reaction was cooled to −35° C., treated dropwise with 1-bromo-3-[4-(trifluoromethyl)phenyl)propane (2.53 g, 0.0095 mol) in DMF (30 mL), and the reaction stirred 2 h. Cooling was removed, reaction stirred 3.5 h, and again cooled to −35° C. The reaction was then treated with additional 1-bromo-3-[4-(trifluoromethyl)phenyl)propane (1.75 g, 0.0043 mol) in DMF (5 mL), cooling removed, and reaction stirred over night. Additional 1-bromo-3-[4-(trifluoromethyl)phenyl)propane (0.75 g, 0.0028 mol) in DMF (5 mL) was added and stirring continued for 1.5 h. The solvent was evaporated, the residue suspended in H$_2$O, and the mixture extracted with ether. The extracts were dried, the solvent evaporated, and the residue purified by radial chromatography (MeOH:EtOAc:NH$_4$OH/15:30:1). The HCl salt (0.32 g) crystallized from CHCl$_3$-EtOAc-ether, m.p. 182°–184° C. (Compound 74)

EXAMPLE 71

3-(1-Butylamino)-4-[(+,−)-3-(1-azabicyclo[2.2.2] octyloxy)]-1,2,5-thiadiazole

A mixture of Compound 12 (1.15 g, 0.0047 mol) and 1-butylamine (20 mL) was heated to reflux for 22 h. The solvent was evaporated, residue suspended in H$_2$O, the mixture acidified, and extracted with ether. The aqueous phase was made basic, extracted with EtOAc, extracts dried, and solvent evaporated. Purification by radial chromatography (MeOH:EtOAc:NH$_4$OH/15:30:1) and conversion to a HCl salt gave a solid partial hydrate (0.046 g), m.p. 193°–195° C. (Compound 75)

EXAMPLE 72

Cyanogen butyloxyimide

A solution of 1-butanol (92 mL, 1 mol) and triethylamine (3 mL) was cooled to −8° C. and cyanogen (58 g, 1.12 mol) was slowly bubbled through the solution while maintaining the temperature below 2° C. The reaction mixture was then distilled at 7 mm Hg to give a clear liquid (119.4 g) b.p. 43°–49° C. (Compound 76).

EXAMPLE 73

3-Chloro-4-butyloxy-1,2,5-thiadiazole

A solution of DMF (400 mL) and sulfur monochloride (230 mL) was cooled to 5° C. and Compound 76 (119.4 g, 0.95 mol) was added dropwise such that the temperature did not exceed 10° C. Cooling was removed and the reaction was stirred over night. The reaction was cooled in an ice-water bath and the excess sulfur monochloride destroyed by dropwise addition of H$_2$O such that the temperature did not exceed 30° C. The liquid was decanted from the semi-solid sulfur precipitant and the sulfur residue triturated with hexane. The aqueous fraction was extracted with hexane (3×) and the combined extracts and triturants were washed with H$_2$O, aqueous NaHCO$_3$, brine, dried, and the solvent evaporated. The yellow liquid residue was distilled at 14 mm Hg to give a clear liquid (153 g), b.p. 120°–125° C. (Compound 77)

EXAMPLE 74

3-Methylthio-4-butyloxy-1,2,5-thiadiazole

A solution of Compound 77 (6 g, 0.031 mol) in DMF (75 mL) was rapidly stirred as ground flaked Na$_2$S-9 H$_2$O (8 g, 0.034 mol) was added. After 1 h, CH$_3$I (3 mL, 0.048 mol) was added and the reaction stirred 30 min. Ice-water (150 mL) was added to the reaction and the mixture extracted with hexane (3×). The extracts were washed with H$_2$O (2×), dried and the solvent evaporated to give a clear liquid (6.04 g). (Compound 78)

EXAMPLE 75

3-Methylsulfonyl-4-butyloxy-1,2,5-thiadiazole

To a solution of Oxone (18.4 g, 0.03 mol) in H$_2$O (100 mL) was added dropwise Compound 78 (3 g, 0.0147 mol) in THF (45 mL). After stirring overnight, the organics were evaporated and the residue extracted with ether (3×). The extracts were washed with $H_2O$ (2×), dried, and the solvent evaporated. The residue was purified by radial chromatography eluting with 50% EtOAc-hexane to give a clear colorless liquid (2.93 g) that solidified on standing, m.p. 39°–40° C. (Compound 79)

EXAMPLE 76

3-Methylthio-4-hexyloxy-1,2,5-thiadiazole

A solution of 3-chloro-4-hexyloxy-1,2,5-thiadiazole (CA 60, 2796e, 1964) (1.1 g, 0.005 mol) in DMF (30 mL) was rapidly stirred as ground flaked $Na_2S$-9 $H_2O$ (1.5 g, 0.00625 mol) was added. After stirring overnight, $CH_3I$ (2 mL) was added and the reaction stirred 30 min. Ice-water (150 mL) was added to the reaction and the mixture extracted with ether (2×). The extracts were washed with $H_2O$ (2×), dried and the solvent evaporated to give a clear liquid (1.025 g). (Compound 80)

EXAMPLE 77

3-Methylsulfonyl-4-hexyloxy-1,2,5-thiadiazole

To a solution of Oxone (18.4 g, 0.03 mol) in $H_2O$ (100 mL) was added dropwise Compound 80 (3.4 g, 0.0147 mol) in THF (50 mL). After stirring for three days, the organics were evaporated and the residue extracted with ether (3×). The extracts were washed with $H_2O$ (2×), dried, and the solvent evaporated. The residue was purified by radial chromatography eluting with 50% EtOAc-hexane to give a clear colorless liquid (3.58 g). (Compound 81)

EXAMPLE 78

Cyanogen propyloxyimide

A solution of 1-propanol (40 mL, 0.536 mol) and triethylamine (1.5 mL) was cooled to –8° C. and cyanogen (36 g, 0.69 mol) was slowly bubbled through the solution while maintaining the temperature below 2° C. The reaction mixture was then distilled at 20 mm Hg to give a clear liquid (59 g) b.p. 63°–64° C. (Compound 82)

EXAMPLE 79

3-Chloro-4-propyloxy-1,2,5-thiadiazole

A solution of DMF (180 mL) and sulfur monochloride (120 mL, 1.5 mol) was cooled to 5° C. and Compound 82 (59 g, 0.527 mol) was added dropwise such that the temperature did not exceed 10° C. Cooling was removed and the reaction was stirred over night. The reaction was cooled in an ice-water bath and the excess sulfur monochloride destroyed by dropwise addition of $H_2O$ such that the temperature did not exceed 30° C. The liquid was decanted from the semi-solid sulfur precipitant and the sulfur residue triturated with hexane. The aqueous fraction was extracted with hexane (3×) and the combined extracts and triturants were washed with $H_2O$, aqueous $NaHCO_3$, brine, dried, and the solvent evaporated. The yellow liquid residue was distilled at 15 mm Hg to give a clear liquid (79.9 g), b.p. 103°–106° C. (Compound 83)

EXAMPLE 80

3-Methylthio-4-propyloxy-1,2,5-thiadiazole

A solution of Compound 83 (11.1 g, 0.062 mol) in DMF (150 mL) was rapidly stirred as ground flaked $Na_2S$-9 $H_2O$ (16.4 g, 0.068 mol) was added. After 1 h, $CH_3I$ (6 mL, 0.096 mol) was added and the reaction stirred 30 min. Ice-water (300 mL) was added to the reaction and the mixture extracted with hexane (3×). The extracts were washed with $H_2O$ (2×), dried and the solvent evaporated to give a clear liquid (11.02 g). (Compound 84)

EXAMPLE 81

3-Methylsulfonyl-4-propyloxy-1,2,5-thiadiazole

To a solution of Oxone (20 g, 0.0325 mol) in $H_2O$ (100 mL) was added dropwise Compound 84 (3 g, 0.0158 mol) in THF (50 mL). After stirring overnight, the organics were evaporated and the residue extracted with ether (3×). The extracts were washed with $H_2O$ (2×), dried, and the solvent evaporated to give a colorless oil. The residue was purified by radial chromatography eluting with 40% EtOAc-hexane to give a clear colorless liquid (3.09 g) that solidified on standing. Recrystallization from hexane gave a white solid, m.p. 30°–31° C. (Compound 85)

EXAMPLE 82

Cyanogen methoxyimide

A solution of methanol (25 mL, 0.618 mol) and triethylamine (1.5 mL) was cooled to –8° C. and cyanogen (38 g, 0.73 mol) was slowly bubbled through the solution while maintaining the temperature below 2° C. The reaction mixture was then distilled at 45 mm Hg to give a clear liquid (51 g) b.p. 48°–53° C. (Compound 86)

EXAMPLE 83

3-Chloro-4-methoxy-1,2,5-thiadiazole

A solution of DMF (180 mL) and sulfur monochloride (120 mL, 1.5 mol) was cooled to 5° C. and Compound 86 (51 g, 0.607 mol) was added dropwise such that the temperature did not exceed 15° C. Cooling was removed and the reaction was stirred over night. The reaction was cooled in an ice-water bath and the excess sulfur monochloride destroyed by dropwise addition of $H_2O$ such that the temperature did not exceed 30° C. The solution was further diluted with $H_2O$ (350 mL) and steam distilled until almost all of the distillate was homogeneous. The distillate was extracted with hexane (3×) and the combined extracts washed with $H_2O$, aqueous $NaHCO_3$, brine, dried, and the solvent distilled off until the volume was 200 mL. The hot mixture was filtered and cooled to give white crystals (53 g). (Compound 87)

EXAMPLE 84

3-Methylthio-4-methoxy-1,2,5-thiadiazole

A solution of Compound 87 (9.4 g, 0.0623 mol) in DMF (150 mL) was rapidly stirred as ground flaked Na2S-9 $H_2O$ (16.4 g, 0.068 mol) was added. After 1 h, $CH_3I$ (6 mL, 0.096 mol) was added and the reaction stirred 30 min. Ice-water (300 mL) was added to the reaction and the mixture extracted with hexane (3×). The extracts were washed with $H_2O$ (2×), dried and the solvent carefully evaporated to give a clear liquid (4.4 g). (Compound 88)

EXAMPLE 85

3-Methylsulfonyl-4-methoxy-1,2,5-thiadiazole

To a solution of Oxone (34 g, 0.0552 mol) in $H_2O$ (170 mL) was added dropwise Compound 88 (4.4 g, 0.027 mol)

in THF (80 mL). After stirring 5 h, the organics were evaporated and the residue extracted with ether (3x). The extracts were washed with $H_2O$ (2x), dried, and the solvent evaporated to give a flocculant white solid. Recrystallization from ether gave a white solid (2.76 g), m.p. 110.5°–111.5° C. (Compound 89)

EXAMPLE 86

3-Chloro-4-pentyloxy-1,2,5-thiadiazole

A solution of 1-pentanol (60 mL, 0.55 mol) and triethylamine (1.5 mL) was cooled to −8° C. and cyanogen (36 g, 0.69 mol) was slowly bubbled through the solution while maintaining the temperature below 2° C. The reaction was then stirred another hour at −5° C. then added dropwise to a solution of DMF (180 mL) and sulfur monochloride (120 mL, 1.5 mol) that was cooled to 5° C. while maintaining the temperature of the DMF solution below 10° C. Cooling was removed and the reaction was stirred over night. The reaction was cooled in an ice-water bath and the excess sulfur monochloride destroyed by dropwise addition of $H_2O$ such that the temperature did not exceed 30° C. The liquid was decanted from the semi-solid sulfur precipitant and the sulfur residue triturated with hexane. The aqueous fraction was extracted with hexane (3x) and the combined extracts and triturants were washed with $H_2O$, aqueous $NaHCO_3$, brine, dried, and the solvent evaporated. The yellow liquid residue was distilled at 9 mm Hg to give a clear liquid (92.7 g), b.p. 129°–135° C. (Compound 90)

EXAMPLE 87

3-Methylthio-4-pentyloxy-1,2,5-thiadiazole

A solution of Compound 90 (12.8 g, 0.06 mol) in DMF (150 mL) was rapidly stirred as ground flaked $Na_2S$-9 $H_2O$ (16.4 g, 0.068 mol) was added. After 1 h, $CH_3I$ (6 mL, 0.096 mol) was added and the reaction stirred 30 min. Ice-water (300 mL) was added to the reaction and the mixture extracted with hexane (3x). The extracts were washed with $H_2O$ (2x), dried and the solvent evaporated to give a clear liquid (12.6 g). (Compound 91)

EXAMPLE 88

3-Methylsulfonyl-4-pentlyoxy-1,2,5-thiadiazole

To a solution of Oxone (72 g, 0.117 mol) in $H_2O$ (350 mL) was added dropwise Compound 91 (12.4 g, 0.0569 mol) in THF (180 mL). After stirring overnight, the organics were evaporated and the residue extracted with ether (3x). The extracts were washed with $H_2O$ (2x), dried, and the solvent evaporated to give a colorless oil. The residue was purified by flash chromatography eluting with 40% EtOAc-hexane to give a clear colorless liquid (13 g). (Compound 92)

EXAMPLE 89

3-Chloro-4-ethoxy-1,2,5-thiadiazole

A solution of ethanol (60 mL, 1.02 mol) and triethylamine (1.5 mL) was cooled to −8° C. and cyanogen (59 g, 1.13 mol) was slowly bubbled through the solution while maintaining the temperature below 2° C. The reaction was then added dropwise to a solution of DMF (275 mL) and sulfur monochloride (225 mL, 2.81 mol) that was cooled to 5° C. while maintaining the temperature of the DMF solution below 10° C. Cooling was removed and the reaction was stirred over night. The reaction was cooled in an ice-water bath and the excess sulfur monochloride destroyed by dropwise addition of $H_2O$ such that the temperature did not exceed 30° C. Additional $H_2O$ (400 mL) was added and the reaction internally steam distilled until the distillate was almost homogeneous. The distillate was extracted with hexane (3x) and the combined extracts washed with H2O, aqueous $NaHCO_3$, brine, dried, and the solvent carefully evaporated. The liquid residue was distilled at 21 mm Hg to give a clear liquid (154.3 g), b.p. 88°–93° C. (Compound 93)

EXAMPLE 90

3-Methylthio-4-ethoxy-1,2,5-thiadiazole

A solution of Compound 93 (16.5 g, 0.1 mol) in DMF (250 mL) was rapidly stirred as ground flaked $Na_2S$-9 $H_2O$ (27 g, 0.113 mol) was added. After 1 h, $CH_3I$ (9.5 mL, 0.153 mol) was added and the reaction stirred 1 h. Ice-water (400 mL) was added to the reaction and the mixture extracted with hexane (3x). The extracts were washed with $H_2O$ (2x), dried and the solvent evaporated to give a clear liquid (12.5 g). (Compound 94)

EXAMPLE 91

3-Methylsulfonyl-4-ethoxy-1,2,5-thiadiazole

To a solution of Oxone (90 g, 0.146 mol) in $H_2O$ (435 mL) was added dropwise 19 (12.5 g, 0.071 mol) in THF (220 mL). After stirring overnight, the organics were evaporated and the residue extracted with ether (3x). The extracts were washed with $H_2O$ (2x), dried, and the solvent evaporated to give a white solid. Recrystallization from ether gave a white solid (9.9 g), m.p. 94°–95° C. (Compound 95)

EXAMPLE 92

3-Chloro-4-(4-methylpentyloxy)-1,2,5-thiadiazole

A solution of 4-methylpentan-1-ol (25 mL, 0.245 mol) and triethylamine (1 mL) was cooled to −8° C. and cyanogen (14 g, 0.27 mol) was slowly bubbled through the solution while maintaining the temperature below 2° C. The reaction was then stirred another hour at −5° C. then added dropwise to a solution of DMF (75 mL) and sulfur monochloride (49 mL) that was cooled to 5° C. while maintaining the temperature of the DMF solution below 10° C. Cooling was removed and the reaction was stirred over night. The reaction was cooled in an ice-water bath and the excess sulfur monochloride destroyed by dropwise addition of H2O such that the temperature did not exceed 35° C. The liquid was decanted from the semi-solid sulfur precipitant and the sulfur residue triturated with hexane. The aqueous fraction was extracted with hexane (3x) and the combined extracts and triturants were washed with $H_2O$, aqueous $NaHCO_3$, brine, dried, and the solvent evaporated. The yellow liquid residue was distilled at 4.5 mm Hg to give a clear liquid (40.45 g), b.p. 120°–124° C. (Compound 96)

EXAMPLE 93

3-Methylthio-4-(4-methylpentyloxy)-1,2,5-thiadiazole

A solution of Compound 96 (22 g, 0.1 mol) in DMF (250 mL) was rapidly stirred as ground flaked $Na_2S$-9 $H_2O$ (27 g, 0.113 mol) was added. After 1 h, $CH_3I$ (9.5 mL, 0.153 mol) was added and the reaction stirred 30 min. Ice-water (300 mL) was added to the reaction and the mixture extracted with hexane (3x). The extracts were washed with $H_2O$ (2x), dried and the solvent evaporated to give a clear liquid (21.6 g). (Compound 97)

EXAMPLE 94

3-Methylsulfonyl-4-(4-methylpentyloxy)-1,2,5-thiadiazole

To a solution of Oxone (119 g, 0.193 mol) in $H_2O$ (600 mL) was added dropwise Compound 97 (21.6 g, 0.093 mol) in THF (300 mL). After stirring overnight, the organics were evaporated and the residue extracted with ether (3×). The extracts were washed with $H_2O$ (2×), dried, and the solvent evaporated to give a colorless oil. The residue was purified by HPLC (8 L gradient, hexane to 40% EtOAc-hexane) to give a clear colorless liquid (19.7 g). (Compound 98)

EXAMPLE 95

3-(1-Butyloxy)-4-[endo-(+,−)-6-(1-azabicyclo[3.2.1] octyloxy)]-1,2,5-thiadiazole A solution of potassium t-butoxide (0.62 g, 0.0055 mol) in THF (12 mL) was treated with endo-(+,−)-1-azabicyclo [3.2.1]octan-6-ol (0.64 g, 0.005 mol). After 5 min, 3-chloro-4-(1-butyloxy)-1,2,5-thiadiazole (1.5 g, 0.0072 mol) was added. After stirring overnight, the solvent was evaporated, the residue diluted with $H_2O$, acidified, and extracted with ether. The aqueous phase was made basic and extracted with EtOAc, the extracts dried, washed with brine, dried, and the solvent evaporated. The residue was purified by radial chromatography (20% EtOH-2% $NH_4OH$—$CHCl_3$). The HCl salt crystallized from EtOAc to give a white solid (0.21 g), m.p. 172°–173° C. dec. (Compound 71)

EXAMPLE 96

(±)-3-(2-Methylthioethyl)-4-(1-azabicyclo[2.2.2] octyl-3-oxy)-1,2,5-thiadiazole

A solution of 3-(2-methylthioethyl)-4-hydroxy-1,2,5-thiadiazole (0.45 g) and triphenylphosphine (0.7 g) was cooled in ice-water as diethyldiazodicarboxylate (0.4 mL) was added dropwise. After addition, (±)-1-azabicyclo[2.2.2] octan-3-ol (0.33 g) was added, cooling removed, and reaction stirred for 1 hour. The solvent was evaporated, residue suspended in water, the mixture acidified and washed with ether. The aqueous solution was made basic and extracted with EtOAc. The extracts were dried, the solvent evaporated, the residue purified by radial chromatography eluting with 10%-EtOH-1%-$NH_4OH$—$CHCl_3$, and the product converted to a HCl salt. Recrystallization from acetone gave 0.6 g white crystals, m.p. 177°–178° C. (Compound 99).

The following compounds were synthesized in substantially the same manner as Compound 99.

EXAMPLE 97

(±)-3-(1-Azabicyclo[2.2.2]octyl-3-oxy)-1,2,5-thiadiazole

A sample of 3-Hydroxy-1,2,5-thiadiazole (0.28 g), triphenylphospine (0.7 g), diethyldiazodicarboxylate (0.4 mL), and (±)-1-azabicyclo[2.2.2]octan-3-ol (0.33 g) gave the hydrochloride salt of (±)-3-(1-azabicyclo[2.2.2]octyl-3-oxy)-1,2,5-thiadiazole, m.p. 240° C. dec. (0.36 g). (Compound 100).

EXAMPLE 98

(±)-3-Hexyl-4-(1-azabicyclo[2.2.2]octyl-3-oxy)-1,2,5-thiadiazole

A sample of 3-Hexyl-4-Hydroxy-1,2,5-thiadiazole (0.93 g), triphenylphospine (1.31 g), diethyldiazodicarboxylate (0.8 mL), and (±)-1-azabicyclo[2.2.2]octan-3-ol (0.64 g) gave the hydrochloride salt of (±)-3-hexyl-4-(1-azabicyclo [2.2.2]octyl-3-oxy)-1,2,5-thiadiazole, m.p. 163°–164° C. dec. (1.11 g). (Compound 101).

EXAMPLE 99

(±)-3-Butylsulfonyl-4-(1-azabicyclo[2.2.2]octyl-3-oxy)-1,2,5-thiadiazole

A solution of potassium t-butoxide (1.2 g) in THF (50 mL) was treated with (±)-1-azabicyclo[2.2.2]octan-3-ol (1.3 g). After 10 min, the reaction was cooled in ice-water and Compound 1 (2.3 g) was added in one portion. Cooling was removed and after two hours the solution was heated to reflux for 4 hours. The solvent was evaporated, residue suspended in water, the mixture acidified and extracted with ether. The aqueous fraction was made basic and extracted with EtOAc. The extracts were washed with water brine, dried, and the solvent evaporated to give Compound 14 (1.95 g). The oil was dissolved in dilute 0.5N HCl (17 mL), cooled in ice-water, and a solution of Oxone (6 g) in water (25 mL) was added over 5 min. Cooling was removed and after 4 hours excess oxidizing agent was destroyed with $NaHSO_3$. The reaction was cooled in ice-water, made basic with 5N NaOH, and extracted with EtOAc. The extracts were washed with brine, dried, and the solvent evaporated to give (±)-3-butylsulfonyl-4-(1-azabicyclo[2.2.2]octyl-3-oxy) -1,2,5-thiadiazole as a yellow oil (1.6 g). The HCl salt crystallized from 2-propanol as a white solid, m.p. 180°–181° C. (Compound 102)

EXAMPLE 100

(±)-3-Propylsulfonyl-4-(1-azabicyclo[2.2.2]octyl-3-oxy)-1,2,5-thiadiazole

Using substantially the same procedure as for Compound 102, (±)-1-azabicyclo[2.2.2]octan-3-ol (4 g) and Compound 37 (4.9 g) gave (±)-3-propylsulfonyl-4-(1-azabicyclo[2.2.2] octyl-3-oxy)-1,2,5-thiadiazole (4.2 g) as a tan liquid that solidified on standing, m.p. 77°–78° C. (Compound 103).

EXAMPLE 101

(±)-3-(4,4,4-Trifluorobutyloxy)-4-(1-azabicyclo [2.2.2]octyl-3-oxy)-1,2,5-thiadiazole A solution of 4,4,4-trifluorobutanol (0.75 g) in THF (20 mL) was cooled to 0° C. and potassium t-butoxide (0.65 g) was added. After 5 min, a solution of Compound 102 (0.6 g) in THF (5 mL) was added and the reaction stirred one hour. The reaction was quenched with 5N HCl (1.5 mL) and the solvent evaporated. The residue was suspended in water and extracted with ether. The aqueous phase was made basic and extracted with EtOAc. The extracts were dried, the solvent evaporated, and the residue purified by radial chromatography eluting with 20%-EtOH-1%-$NH_4OH$—$CHCl_3$ to give a clear oil. The HCl salt was recrystallized from EtOAc-ether to give a white solid, m.p. 122°–124° C. (0.43 g). (Compound 104).

The following compounds were prepared in substantially the same manner:

EXAMPLE 102

(±)-3-(2-butynyloxy)-4-(1-azabicyclo[2.2.2]octyl-3-oxy)-1,2,5-thiadiazole

Using substantially the same procedure used in the preparation Compound 104, 2-butynol (0.45 g) and Compound 102 (0.6 g) gave after chromatography, (±)-3-(2-butynyloxy)-4-(1-azabicyclo[2.2.2]octyl-3-oxy)-1,2,5-thiadiazole (0.45 g) as an HCl salt that crystallized from 2-propanol, m.p. 200°–201° C. (Compound 105)

EXAMPLE 103

(±)-3-(Cyclopropylmethoxy)-4-(1-azabicyclo[2.2.2]octyl-3-oxy)-1,2,5-thiadiazole

Using substantially the same procedure used in the preparation Compound 104, cyclopropylmethanol (0.5 mL) and Compound 102 (0.6 g) gave after chromatography, (±)-3-(Cyclopropylmethoxy)-4-(1-azabicyclo[2.2.2]octyl-3-oxy)-1,2,5-thiadiazole (0.49 g) as an HCl salt that crystallized from acetone, m.p. 217°–218° C. (Compound 106)

EXAMPLE 104

(±)-3-(3-Phenylpropynyloxy)-4-(1-azabicyclo[2.2.2]octyl-3-oxy)-1,2,5-thiadiazole Using substantially the same procedure used in the preparation of Compound 104, 3-phenylpropynol (0.85 g) and Compound 102 (0.66 g) gave after chromatography (±)-3-(3-phenylpropynyloxy)-4-(1-azabicyclo[2.2.2]octyl-3-oxy)-1,2,5-thiadiazole as an HCl salt (0.66 g) that crystallized from ether-CHCl$_3$, m.p. 184°–186° C. (Compound 107)

EXAMPLE 105

(±)-3-(3-Butenyloxy)-4-(1-azabicyclo[2.2.2]octyl-3-oxy)-1,2,5-thiadiazole

Using substantially the same procedure used in the preparation Compound 104, 3-butenol (0.5 mL) and Compound 102 (0.6 g) gave after chromatography, (±)-3-(3-butenyloxy)-4-(1-azabicyclo[2.2.2]octyl-3-oxy)-1,2,5-thiadiazole (0.47 g) as an HCl salt that crystallized from acetone, m.p. 198°–199° C. (Compound 108).

EXAMPLE 106

(±)-3-(trans-2-Butenyloxy)-4-(1-azabicyclo[2.2.2]octyl-3-oxy)-1,2,5-thiadiazole

Using substantially the same procedure used in the preparation Compound 104, trans-2-butenol (0.45 g) and Compound 102 (0.6 g) gave after chromatography, (±)-3-(trans-2-butenyloxy)-4-(1-azabicyclo[2.2.2]octyl-3-oxy)-1,2,5-thiadiazole (0.51 g) as an HCl salt that crystallized from 2-propanol, m.p. 182.5°–184° C. (Compound 109).

EXAMPLE 107

(±)-3-(cis-2-Butenyloxy)-4-(1-azabicyclo[2.2.2]octyl-3-oxy)-1,2,5-thiadiazole

Using substantially the same procedure used in the preparation Compound 104, cis-2-butenol (0.45 g) and Compound 102 (0.5 g) gave after chromatography, (±)-3-(cis-2-butenyloxy)-4-(1-azabicyclo[2.2.2]octyl-3-oxy)-1,2,5-thiadiazole (0.34 g) as an HCl salt that crystallized from acetone, m.p. 178°–179° C. (Compound 110).

EXAMPLE 108

(±)-3-(2-Methoxyethoxy)-4-(1-azabicyclo[2.2.2]octyl-3-oxy)-1,2,5-thiadiazole

Using substantially the same procedure used in the preparation Compound 104, 2-methoxyethanol (0.45 g) and Compound 102 (0.5 g) gave after chromatography, (±)-3-(2-methoxyethoxy)-4-(1-azabicyclo[2.2.2]octyl-3-oxy)-1,2,5-thiadiazole (0.32 g) as an HCl salt that crystallized from acetone, m.p. 131°–134° C. (Compound 111).

EXAMPLE 109

(±)-3-(2-Phenoxyethoxy)-4-(1-azabicyclo[2.2.2]octyl-3-oxy)-1,2,5-thiadiazole

Using substantially the same procedure used in the preparation of Compound 104, 2-phenoxyethanol (0.55 g) and Compound 102 (0.4 g) gave (±)-3-(2-phenoxyethoxy)-4-(1-azabicyclo[2.2.2]octyl-3-oxy)-1,2,5-thiadiazole as an HCl salt (0.43 g) that crystallized from ether-CHCl$_3$, m.p. 213°–215° C. (Compound 112).

EXAMPLE 110

(±)-3-(3-Butynoxy)-4-(1-azabicyclo[2.2.2]octyl-3-oxy)-1,2,5-thiadiazole

Using substantially the same procedure used in the preparation of Compound 104, 3-butynol (0.27 g) and Compound 102 (0.4 g) gave after chromatography (±)-3-(3-butynoxy)-4-(1-azabicyclo[2.2.2]octyl-3-oxy)-1,2,5-thiadiazole as an HCl salt (0.19 g) that crystallized from ether-CHCl$_3$, m.p. 207°–208° C. (Compound 113).

EXAMPLE 111

(±)-3-(2-Cyclopropylethoxy)-4-(1-azabicyclo[2.2.2]octyl-3-oxy)-1,2,5-thiadiazole Using substantially the same procedure used in the preparation Compound 104, 2-cyclopropylethanol (0.52 g) and Compound 102 (0.5 g) gave after chromatography, (±)-3-(2-cyclopropylethoxy)-4-(1-azabicyclo[2.2.2]octyl-3-oxy)-1,2,5-thiadiazole (0.48 g) as an HCl salt that crystallized from acetone, m.p. 192°–193° C. (Compound 114).

EXAMPLE 112

(±)-3-(2-(Methylthio)ethoxy)-4-(1-azabicyclo[2.2.2]octyl-3-oxy)-1,2,5-thiadiazole Using substantially the same procedure used in the preparation Compound 104, 2-(methylthio)ethanol (0.52 mL) and Compound 102 (0.5 g) gave after chromatography, (±)-3-(2-(methylthio)ethoxy)-4-(1-azabicyclo[2.2.2]octyl-3-oxy)-1,2,5-thiadiazole (0.4 g) as an HCl salt that crystallized from acetone, m.p. 187°–188° C. (Compound 115)

EXAMPLE 113

(±)-3-(3-Chloropropoxy)-4-(1-azabicyclo[2.2.2]octyl-3-oxy)-1,2,5-thiadiazole

Using substantially the same procedure used in the preparation Compound 104, 3-chloropropanol (0.5 mL) and Compound 102 (0.4 g) gave after chromatography, (±)-3-(3-chloropropoxy)-4-(1-azabicyclo[2.2.2]octyl-3-oxy)-1,2,5-thiadiazole (0.25 g) as an HCl salt that crystallized from acetone-EtOAc, m.p. 167°–168° C. (Compound 116).

EXAMPLE 114

(±)-3-(4-Fluorobutyloxy)-4-(1-azabicyclo[2.2.2]octyl-3-oxy)-1,2,5-thiadiazole

Using substantially the same procedure used in the preparation Compound 104, 4-fluorobutanol (0.6 g) and Compound 102 (0.4 g) gave after chromatography, (±)-3-(4-fluorobutyloxy)-4-(1-azabicyclo[2.2.2]octyl-3-oxy)-1,2,5-thiadiazole (0.34 g) as an HCl salt that crystallized from acetone-EtOAc, m.p. 180.5°–181.5° C. (Compound 117).

EXAMPLE 115

(±)-3-(2-[4-Chlorophenoxy]ethoxy)-4-(1-azabicyclo[2.2.2]octyl-3-oxy)-1,2,5-thiadiazole Using substantially the same procedure used in the preparation of Compound 104, 2-(4-chlorophenoxy)ethanol (0.77 g) and Compound 102 (0.4 g) gave after chromatography (±)-3-(2-[4-chlorophenoxy]ethoxy)-4-(1-azabicyclo[2.2.2]octyl-3-oxy)-1,2,5-thiadiazole as an HCl salt (0.44 g) that crystallized from ether-CHCl$_3$, m.p. 224°–226° C. (Compound 118).

EXAMPLE 116

(±)-3-(3-[2-Methoxy-5-pyridyl]propyloxy)-4-(1-azabicyclo[2.2.2]octyl-3-oxy)-1,2,5-thiadiazole Using substantially the same procedure used in the preparation of Compound 104, 3(2-methoxy-5-pyridyl)propanol (0.75 g) and Compound 102 (0.4 g) gave after chromatography (±)-3-(3-[2-methoxy-5-pyridyl]propyloxy)-4-(1-azabicyclo[2.2.2]octyl-3-oxy)-1,2,5-thiadiazole as an HCl salt (0.48 g) that crystallized from ether-CHCl$_3$, m.p. 148°–150° C. (Compound 119).

EXAMPLE 117

(±)-3-(trans-3-Chloro-2-propenyloxy)-4-(1-azabicyclo[2.2.2]octyl-3-oxy)-1,2,5-thiadiazole Using substantially the same procedure used in the preparation Compound 104 except that the reaction was conducted at −15° C., trans-3-chloro-2-propenol (0.5 g) and Compound 102 (0.4 g) gave after chromatography, (±)-3-(trans-3-chloro-2-propenyloxy)-4-(1-azabicyclo[2.2.2]octyl-3-oxy)-1,2,5-thiadiazole (0.33 g) as an HCl salt that crystallized from acetone, m.p. 176.5°–177.5° C. (Compound 120).

EXAMPLE 118

(±)-3-(2-[4-Fluorophenoxy]ethoxy)-4-(1-azabicyclo[2.2.2]octyl-3-oxy)-1,2,5-thiadiazole Using substantially the same procedure used in the preparation of Compound 104, 2-(4-fluorophenoxy)ethanol (0.53 g) and Compound 102 (0.4 g) gave after chromatography (±)-3-(2-[4-fluorophenoxy]ethoxy)-4-(1-azabicyclo[2.2.2]octyl-3-oxy)-1,2,5-thiadiazole as an HCl salt (0.43 g) that crystallized from ether-CHCl$_3$, m.p. 187°–189° C. (Compound 121).

EXAMPLE 119

(±)-3-(4-Pentenyloxy)-4-(1-azabicyclo[2.2.2]octyl-3-oxy)-1,2,5-thiadiazole

Using substantially the same procedure used in the preparation Compound 104, 4-pentenol (0.6 mL) and Compound 102 (0.4 g) gave after chromatography, (±)-3-(4-pentenyloxy)-4-(1-azabicyclo[2.2.2]octyl-3-oxy)-1,2,5-thiadiazole (0.37 g) as an HCl salt that crystallized from EtOAc, m.p. 165°–166° C. (Compound 122).

EXAMPLE 120

(±)-3-(3-Fluoropropyloxy)-4-(1-azabicyclo[2.2.2]octyl-3-oxy)-1,2,5-thiadiazole

Using substantially the same procedure used in the preparation Compound 104, 3-fluoropropanol (0.4 g) and Compound 102 (0.4 g) gave after chromatography, (±)-3-(3-fluoropropyloxy)-4-(1-azabicyclo[2.2.2]octyl-3-oxy)-1,2,5-thiadiazole (0.3 g) as an HCl salt that crystallized from acetone, m.p. 206°–207° C. (Compound 123).

EXAMPLE 121

(±)-3-(Cyclobutylmethoxy)-4-(1-azabicyclo[2.2.2]octyl-3-oxy)-1,2,5-thiadiazole

Using substantially the same procedure used in the preparation Compound 104, cyclobutylmethanol (0.6 mL) and Compound 102 (0.4 g) gave after chromatography, (±)-3-(cyclobutylmethoxy)-4-(1-azabicyclo[2.2.2]octyl-3-oxy)-1,2,5-thiadiazole (0.33 g) as an HCl salt that crystallized from acetone, m.p. 212°–213° C. (Compound 124).

EXAMPLE 122

(±)-3-(3,3,3,2,2-Pentafluoropropyloxy)-4-(1-azabicyclo[2.2.2]octyl-3-oxy)-1,2,5-thiadiazole Using substantially the same procedure used in the preparation of Compound 104, 3,3,3,2,2-heptafluoropropanol (0.69 g) and Compound 102 (0.4 g) gave after chromatography (±)-3-(3,3,3,2,2-heptafluoropropyloxy)-4-(1-azabicyclo[2.2.2]octyl-3-oxy)-1,2,5-thiadiazole as an HCl salt (0.44 g) that crystallized from ether-CHCl$_3$, m.p. 185°–186° C. (Compound 125).

EXAMPLE 123

(±)-3-(2-[Phenylthio]ethoxy)-4-(1-azabicyclo[2.2.2]octyl-3-oxy)-1,2,5-thiadiazole Using substantially the same procedure used in the preparation of Compound 104, 2-(phenylthio)ethanol (0.71 g) and Compound 102 (0.4 g) gave after chromatography (±)-3-(2-[phenylthio]ethoxy)-4-(1-azabicyclo[2.2.2]octyl-3-oxy)-1,2,5-thiadiazole as an HCl salt (0.37 g) that crystallized from ether-CHCl$_3$, m.p. 187°–189° C. (Compound 126).

EXAMPLE 124

(±)-3-(2-[1-Napthyloxy]ethoxy)-4-(1-azabicyclo[2.2.2]octyl-3-oxy)-1,2,5-thiadiazole Using substantially the same procedure used in the preparation of Compound 104, 2-(1-napthyloxy)ethanol (0.839 g) and Compound 102 (0.4 g) gave after chromatography (±)-3-(2-[1-napthyloxy]ethoxy)-4-(1-azabicyclo[2.2.2]octyl-3-oxy)-1,2,5-thiadiazole as an HCl salt (0.51 g) that crystallized from ether-CHCl$_3$, m.p. 223°–225° C. (Compound 127).

EXAMPLE 125

(±)-3-(2-[4-Bromophenoxy]ethoxy)-4-(1-azabicyclo[2.2.2]octyl-3-oxy)-1,2,5-thiadiazole Using substantially the same procedure used in the preparation of Compound 104, 2-(4-bromophenoxy)ethanol (0.97 g) and Compound 102 (0.4 g) gave after chromatography (±)-3-(2-[4-bromophenoxy]ethoxy)-4-(1-azabicyclo[2.2.2]octyl-3-oxy)-1,2,5-thiadiazole as an HCl salt (0.53 g) that crystallized from ether-CHCl$_3$, m.p. 223°–224° C. (Compound 128).

EXAMPLE 126

(±)-3-(2-Hydroxyethoxy)-4-(1-azabicyclo[2.2.2]octyl-3-oxy)-1,2,5-thiadiazole

A solution of ethylene glycol (9 mL) and potassium t-butoxide (1.5 g) was treated with Compound 102 (0.8 g).

After stirring over night, the reaction was heated to 55° C. for 1 h. The reaction was then cooled, diluted with water, and extracted with EtOAc. The extracts were washed with brine, dried, and the solvent evaporated to give a clear liquid. The liquid was purified by radial chromatography eluting with 20%-EtOH-2%-NH$_4$OH—CHCl$_3$ and then crystallized from ether to give a white solid (0.45 g), m.p. 119.5°–120.5° C. (Compound 129)

EXAMPLE 127

3-Butylthio-4-hydroxy-1,2,5-thiadiazole

A solution of Compound 1 (20.9 g), DMSO (20 mL) and 2N NaOH (205 mL) was headed to reflux overnight. The solution was cooled to 15° C. and concentrated HCl was added until the pH was 1. The solid was collected, washed with water, and dried to give a solid (17.68 g). Recrystallization from heptane gave white crystals, m.p. 72°–72.5° C. (Compound 130).

EXAMPLE 128

(±)exo-3-Butylthio-4-(1-azabicyclo[2.2.1]heptyl-3-oxy)-1,2,5-thiadiazole

A solution of triphenylphosphine (0.7 g) and Compound 130 (0.5 g) in THF (20 mL) was cooled in ice-water. Diethyl diazodicarboxylate (0.4 mL) was added dropwise followed by addition of (±)endo-3-hydroxy-1-azabicyclo[2.2.1] heptane (0.29 g). Cooling was removed and after 1 h the solvent was evaporated. The residue was suspended in cold water, acidified, and extracted with ether. The aqueous fraction was made basic and extracted with EtOAc. The extracts were dried, the solvent evaporated, and the residue purified by radial chromatography eluting with 5%-EtOH-0.5% NH$_4$OH—CHCl$_3$ to give a clear oil. The HCl salt crystallized from EtOAc as white crystals (0.44 g), m.p. 147°–148° C. (Compound 131).

EXAMPLE 129

(±)-3-(2-[3-{1,2,5-Thiadiazoyloxy}]ethoxy)-4-(1-azabicyclo[2.2.2]octyl-3-oxy)-1,2,5-thiadiazole A solution of triphenylphosphine (0.35 g) and 3-hydroxy-1,2,5-thiadiazole (0.14 g) in THF (15 mL) was cooled in ice-water. Diethyl diazodicarboxylate (0.21 g) was added dropwise followed by (±)-3-(2-hydroxyethoxy)-4-(1-azabicyclo[2.2.2]octyl-3-oxy)-1,2,5-thiadiazole (0.35 g). Cooling was removed, reaction was stirred 1 h, and the solvent was evaporated. The residue was suspended in cold water, acidified, and extracted with ether. The aqueous fraction was made basic and extracted with EtOAc. The extracts were washed with brine, dried, the solvent evaporated, and the residue purified by radial chromatography eluting with 10%-EtOH-1% NH$_4$OH—CHCl$_3$ to give a clear oil. The HCl salt crystallized from acetone as a white powder (0.34 g), m.p. 178°–179° C. (Compound 132).

EXAMPLE 130

(±)-exo-3-Butyloxy-4-(7-azabicyclo[2.2.1]heptyl-3-oxy)-1,2,5-thiadiazole

A solution of exo-7-azabicyclo[2.2.1]heptan-3-ol (0.4 g)(Ref. J. Org. Chem. 1994, 59, 1771) in THF (25 mL) was cooled in ice-water and treated dropwise with 1.6M n-butyllithium in hexane (3.5 mL). Cooling was removed and, after 15 min, compound 79 (0.65 g) was added. After another 45 min, the reaction was heated to reflux over night. The solvent was evaporated, the residue suspended in water, the mixture acidified, and extracted with ether. The aqueous fraction was made basic and extracted with EtOAc. The extracts were dried, the solvent evaporated, and the residue purified by radial chromatography eluting with 5%-EtOH-0.5% NH$_4$OH—CHCl$_3$ then 10%-EtOH-1% NH$_4$OH—CHCl$_3$ to give a clear oil. The HCl salt crystallized from EtOAc-ether as floculant white crystals (0.4 g), m.p. 116°–117° C. (Compound 133).

EXAMPLE 131

(±)-3-Butyloxy-4-(3-piperidinyloxy)-1,2,5-thiadiazole

A suspension of (±)-3-hydroxypiperidine hydrochloride (0.5 g) in THF (20 mL) was treated dropwise with 1.6M n-butyllithium in hexane (4.6 mL). After 1 h, compound 79 (0.6 g) was added and the reaction was heated to reflux for 6.5 h. The solvent was evaporated, the residue suspended in cold water, acidified, and extracted with ether. The aqueous fraction was made basic and extracted with CHCl$_3$. The extracts were dried, the solvent evaporated, and the residue purified by radial chromatography eluting with 10%-EtOH-1% NH$_4$OH—CHCl$_3$ to give a clear oil. The HCl salt crystallized from EtOAc as a white solid (0.38 g), m.p. 124°–125° C. (Compound 134).

EXAMPLE 132

3-Butyloxy-4-(cis-1R-2-aminocyclopentanoxy)-1,2,5-thiadiazole

A suspension of cis-1R-2-aminocyclopentanol hydrochloride (0.35 g) in THF (25 mL) was cooled in ice-water as 1.6M n-butyllithium in hexane (3.2 mL) was added. Cooling was removed and after 30 min, compound 79 (0.3 g) was added and the reaction was heated to reflux for 1 h. Additional compound 79 (0.3 g) was added and the reaction heated to reflux over night. The solvent was evaporated, the residue suspended in ice-water, acidified, and extracted with ether. The aqueous fraction was made basic, extracted with CHCl$_3$, the extracts dried, the solvent evaporated, and the residue purified by raidal chromatography eluting with 10%-EtOH-1% NH$_4$OH—CHCl$_3$ to give a straw colored oil. The HCl salt crystallized ether as a tan solid (0.19 g), m.p. 105°–106.5° C. (Compound 135).

EXAMPLE 133

(±)-endo-3-Hexyloxy-4-(1-azabicyclo[3.2.1]octyl-6-oxy)-1,2,5-thiadiazole

A solution of potassium tert-butoxide (0.65 g) in THF (15 mL) was treated with (±)-endo-1-azabicyclo[3.2.1]octan-6-ol (0.64 g). After 10 min, 3-chloro-4-hexyloxy-1,2,5-thiadiazole (1.4 g) was added and the reaction stirred for 3 days. The solvent was evaporated, the residue suspended in ice-water, the mixture acidified, and extracted with ether. The aqueous fraction was made basic, extracted with EtOAc, the extracts dried and the solvent evaporated. The residue was purifed by radial chromatography eluting with 20%-EtOH-2%-NH$_4$OH—CHCl$_3$ to give a clear oil (0.5 g). The HCl salt crystallized from EtOAc to give a white solid, m.p. 160°–161° C. (Compound 136).

The resolved enantiomers of endo-1-azabicyclo[3.2.1] octan-6-ol were obtained by the reduction of the resolved ketones (reference the Novo patent) as described in reference.

EXAMPLE 134

(5S,6S)-endo-3-Butylthio-4-(1-azabicyclo[3.2.1] octyl-6-oxy)-1,2,5-thiadiazole

A solution of potassium tert-butoxide (0.65 g) in THF (25 mL) was treated with (5S,6S)-endo-1-azabicyclo[3.2.1]

octan-6-ol (0.65 g). After 5 min, the reaction was cooled in ice-water and compound 1 (1.2 g) was added. Cooling was removed and the reaction was stirred over night. The solvent was evaporated, the residue suspended in ice-water, and the mixture acidified and extracted with ether. The aqueous fraction was made basic, extracted with EtOAc, the extracts dried, the solvent evaporated, and the residue purified by radial chromatography eluting with 20%-EtOH-2% NH$_4$OH—CHCl$_3$ to give an oil. The HCl salt crystallized from EtOAc as floculant white crystals (0.59 g), m.p. 201° C., [α]$_D$=11.44° (EtOH). (Compound 137).

EXAMPLE 135

(5R, 6R)-endo-3-Butylthio-4-(1-azabicyclo[3.2.1]octyl-6-oxy)-1,2,5-thiadiazole Using the procedure described for the preparation of Compound 137, (5R,6R)-endo-1-azabicyclo[3.2.1]octan-6-ol (0.65 g), potassium tert-butoxide (0.65 g) and compound 1 (1.2 g) gave floculant white crystals of the HCl salt of 334559 (0.62 g), m.p. 201°–202° C., [α]$_D$=−12.33° (EtOH). (Compound 138)

EXAMPLE 136

1-Azabicyclo[4.3.0]nona-6,8-diene-5-one

A solution of Ethyl-4-(N-pyrrolo)butanoate (ref. Tetrahedron Letters 1994, 35, 3905) (3.64 g) in CH$_2$Cl$_2$ (400 mL) was treated dropwise with 1M BBr$_3$ in CH$_2$Cl$_2$ (60 mL)). After 30 min, the reaction was quenched with water (50 mL) and neutralized with aqueous NaHCO$_3$. The organics were separated, washed with aqueous NaHCO$_3$, brine, dried, and the solvent evaporated. The residue was purified by hplc using a 10%-EtOAc-hexane to 30% EtOAc-hexane gradient to give an oil (5.2 g). (Compound 139).

EXAMPLE 137

(±)-cis+trans-1-Azabicyclo[4.3.0]nonan-5-ols

A mixture of Compound 139 (5.2 g), 5% Rh/Al$_2$O$_3$ (1.3 g), in EtOH (95 mL) was treated with H$_2$ at 60 psi for 2 h. Another aliquote of 5% Rh/Al$_2$O$_3$ (1.3 g) was added and hydrogenation was continued over night. The catalyst was removed and solvent evaporated to give an oil (4.2 g) that had appropriate mass spectrum for the alcohols, m/e=141. (Compound 140).

EXAMPLE 138

(±)-trans-3-Butylthio-4-(1-azabicyclo[4.3.0]nonyl-5-oxy)-1,2 5-thiadiazole

A solution of Compound 140 (0.7 g) in THF (20 mL) was treated with potassium tert-butoxide (0.6 g). After 5 min, compound 1 (1.1 g) was added, the reaction stirred 1 h, then heated to reflux 1 h. The solvent was evaporated, the residue suspended in ice-water, and the mixture acidified. After extracting with ether, the aqueous fraction was made basic and extracted with EtOAc. The EtOAc extracts were dried, the solvent evaporated, and the residue purified by radial chromatography eluting with 5%-EtOH-0.5% NH$_4$OH—CHCl$_3$ to give an oil. The HCl salt crystallized from EtOAc as a white solid (0.21 g), m.p. 162°–163° C. (Compound 141).

EXAMPLE 139

(±) -cis-3-Butylthio-4-(1-azabicyclo[4.3.0]nonyl-5-oxy)-1,2,5-thiadiazole

Further elution during the chromatographic purification of Compound 141 gave another clear oil. The HCl crystallized from EtOAc as a white solid (0.18 g), m.p. 125°–126° C. (Compound 142).

EXAMPLE 140

(±)-trans-3-Butylthio-4-(2-dimethylaminocyclopentyloxy)-1,2,5-thiadiazole

A solution of potassium tert-butoxide (0.7 g) in THF (20 mL) was treated with (±)-trans-2-dimethylaminocyclopentanol (0.8 g). After 10 min, the reaction was cooled in ice-water and compound 1 (1.25 g) was added. Cooling was removed and the reaction was stirred over night. After heating to reflux for 2 h, the solvent was evaporated, the residue suspended in ice-water, and the mixture acidified. The mixture was extracted with ether and the aqueous phase made basic. Extraction with EtOAc, drying of the extracts, evaporation of the solvent, and purification by radial chromatography eluting with 10%-EtOH-1% NH$_4$OH—CHCl$_3$ gave a tan liquid. The HCl salt crystallized from EtOAc-ether to give a white solid (0.55 g), m.p. 124°–125° C. (Compound 143).

EXAMPLE 141

3-Butylthio-4-(2-dimethylaminoethoxy)-1,2,5-thiadiazole

A solution of potassium tert-butoxide (0.6 g) in THF (20 mL) was treated with 2-dimethylaminoethanol (0.5 mL). After 5 min, compound 1 (1.05 g) was added and the reaction stirred 2 h. The solvent was evaporated, residue suspended in ice-water, and the mixture acidified. The mixture was extracted with ether then the aqueous fraction made basic. Extraction with EtOAc, drying of the extracts, evaporation of the solvent, and purification of the residue by radial chromatography eluting with 5%-EtOH-0.5% NH$_4$OH—CHCl$_3$ gave an oil. The HCl salt crystallized from EtOAc as a white solid (0.47 g), m.p. 104°–105° C. (Compound 144).

EXAMPLE 142

(±)-trans-3-Butylthio-4-(N-tert-butylcarboxy-4-hydroxy-pyrollidin-3-oxy)-1,2,5-thiadiazole A mixture of NaOH (0.12 g) and DMF (15 mL) was treated with Compound 130 (0.95 g) and the reaction stirred 1 h. The solution was treated with 3,4-epoxy-N-tert-butylcarboxypyrollidine (0.8 g) and the solution heated at 60° C. over night. The temperature of the reaction was then increased to 110° C. for 7.5 h. The solvent was evaporated, the residue suspended in ice-water, and the mixture extracted with EtOAc. The extracts were washed with water, brine, the extracts dried, and the solvent evaporated. The residue was purified by radial chromatography eluting with 50% EtOAc-hexane to give an oil (0.44 g). (Compound 145).

EXAMPLE 143

(±)-trans-3-Butylthio-4-(4-hydroxy-pyrollidin-3-oxy)-1,2,5-thiadiazole

A solution of Compound 145 (0.44 g) in EtOAc (15 mL) was cooled in ice-water as a stream of dry HCl was introduced for 2 min. Cooling was removed and after 5 min the solvent was evaporated. The residue was dissolved in cold water, extracted with ether, and the aqueous phase made basic. The aqueous was extracted with EtOAc, the extracts dried, the solvent evaporated, and the residue purified by radial chromatography eluting with 20%-EtOH-2%

NH$_4$OH—CHCl$_3$ to give a white solid. The HCl salt crystallized from acetone-ether as a white solid (0.23 g), m.p. 106°–108° C. (Compound 146).

EXAMPLE 144

(±)-endo-3-Butyloxy-4-(1-azabicyclo[3.2.1]octyl-6-oxy)-1,2,5-thiadiazole

A solution of potassium tert-butoxide (0.62 g) in THF (10 mL) was treated with (±)-endo-1-azabicyclo[3.2.1]octan-6-ol (0.64 g). After 5 min, the reaction was cooled in ice-water, compound 77 (1.5 g) was added, cooling was removed, and the reaction stirred over night. The solvent was evaporated, the residue suspended in ice-water, the mixture acidified, and the mixture extracted with ether. The aqueous fraction was made basic, extracted with EtOAc, the extracts dried, the solvent evaporated, and the residue purified by radial chromatography eluting with 20%-EtOH-2% NH$_4$OH—CHCl$_3$. The HCl salt crystallized from EtOAc to give a white solid (0.21 g), m.p. 172°–173° C. (Compound 147).

EXAMPLE 145

(±)-3-(4-Phenylbutylthio)-4-(1-azabicyclo[2.2.2]octyl-3-oxy)-1,2,5-thiadiazole

Using substantially the same procedure used in the preparation of compound 40, compound 12 (1.15 g) and 1-iodo-4-phenylbutane (4.92 g) gave (±)-3-(4-phenylbutylthio)-4-(1-azabicyclo[2.2.2]octyl-3-oxy)-1,2,5-thiadiazole as a HCl salt (0.59 g) crystallizing from ether-EtOAc-CHCl$_3$, m.p. 136°–139° C. (Compound 148).

EXAMPLE 146

(±)-3-(3-Phenyl-2-propenylthio)-4-(1-azabicyclo[2.2.2]octyl-3-oxy)-1,2,5-thiadiazole Using substantially the same procedure used for the preparation of compound 44, compound 12 (1.15 g) and cinnamyl bromide (3.73 g) gave (±)-3-(3-phenyl-2-propenylthio)-4-(1-azabicyclo[2.2.2]octyl-3-oxy)-1,2,5-thiadiazole as an HCl salt (0.095 g) crystallizing from ether-EtOAc-CHCl$_3$, m.p. 211°–213° C. (Compound 149).

EXAMPLE 147

(±)-3-(3-[4-Fluorophenyl]propan-3-onethio)-4-(1-azabicyclo[2.2.2]octyl-3-oxy)-1,2,5-thiadiazole Using substantially the same procedure used in the preparation of compound 40, compound 12 (1.15 g) and 1-chloro-3-(4-fluorophenyl)propan-3-one (3.52 g) gave (±)-3-(3-[4-Fluorophenyl]propan-3-onethio)-4-(1-azabicyclo[2.2.2]octyl-3-oxy)-1,2,5-thiadiazole as a HCl salt (0.375 g) crystallizing from ether-EtOAc-CHCl$_3$, m.p. 203°–204° C. (Compound 150).

EXAMPLE 148

(±)-3-(3-[N-phenothiazinyl]propylthio)-4-(1-azabicyclo[2.2.2]octyl-3-oxy)-1,2,5-thiadiazole Using substantially the same procedure used in the preparation of compound 13, compound 12 (1.15 g) and 1-bromo-3-(N-phenothiazinyl)propane (1.25 g) gave (±)-3-(3-[N-phenothiazinyl]propylthio)-4-(1-azabicyclo[2.2.2]octyl-3-oxy)-1,2,5-thiadiazole as a HCl salt (0.35 g) crystallizing from EtOAc, m.p. 194°–196° C. (Compound 151).

EXAMPLE 149

(±)-3-(3-[4-Fluorophenyl]-3-[4-fluorophenoxy]propylthio)-4-(1-azabicyclo[2.2.2]octyl-3-oxy)-1,2,5-thiadiazole Using substantially the same procedure used in the preparation of compound 13, compound 12 (1.15 g) and 1-chloro-3-(4-fluorophenyl)-3-(4-fluorophenoxy)propane (2.6 g) gave (±)-3-(3-[4-fluorophenyl]-3-[4-fluorophenoxy]propylthio)-4-(1-azabicyclo[2.2.2]octyl-3-oxy)-1,2,5-thiadiazole as an oxalate salt (0.42 g) crystallizing from EtOAc-ether, m.p. 87°–96° C. (Compound 152).

EXAMPLE 150

(±)-3-(3-Phenyl-3-[4-trifluoromethylphenoxy]propylthio)-4-(1-azabicyclo[2.2.2]octyl-3-oxy)-1,2,5-thiadiazole Using substantially the same procedure used in the preparation of compound 13, compound 12 (1.15 g) and 1-chloro-3-phenyl-3-(4-trifluoromethylphenoxy)propane (2.0 g) gave (±)-3-(3-phenyl-3-[4-trifluoromethylphenoxy]propylthio)-4-(1-azabicyclo[2.2.2]octyl-3-oxy)-1,2,5-thiadiazole as an oxalate salt (0.198 g) crystallizing from CHCl$_3$-ether, m.p. 74°–83° C. (Compound 153).

EXAMPLE 151

(±)-3-(4,4,4-trifluorobutylthio)-4-(1-azabicyclo[2.2.2]octyl-3-oxy)-1,2,5-thiadiazole Using substantially the same procedure used in the preparation of compound 13, compound 12 (1.15 g) and bromo-4,4,4-trifluorobutane (1.81 g) gave (±)-3-(4,4,4-trifluorobutylthio)-4-(1-azabicyclo[2.2.2]octyl-3-oxy)-1,2,5-thiadiazole as a HCl salt (1.43 g) crystallizing from CHCl$_3$-ether, m.p. 128°–130° C. (Compound 154).

EXAMPLE 152

(±)-3-(3-[3-pyridyl]propylthio)-4-(1-azabicyclo[2.2.2]octyl-3-oxy)-1,2,5-thiadiazole Using substantially the same procedure used in the preparation of compound 13, compound 12 (1.15 g) and bromo-3-(3-pyridyl)propane (1.42 g) gave (±)-3-(3-[3-pyridyl]propylthio)-4-(1-azabicyclo[2.2.2]octyl-3-oxy)-1,2,5-thiadiazole as a HCl salt (0.92 g) crystallizing from CHCl$_3$-ether-EtOAc, m.p. 202°–204° C. (Compound 155).

EXAMPLE 153

(±)-endo-3-(2-Phenoxyethylthio)-4-(1-azabicyclo[3.2.1]octyl-6-oxy)-1,2,5-thiadiazole Using substantially the same procedure used in the preparation of compound 72, compound 48 (1.15 g) and bromo-2-phenoxyethane (3.8 g) gave (±)-endo-3-(2-phenoxyethylthio)-4-(1-azabicyclo[3.2.1]octyl-6-oxy)-1,2,5-thiadiazole as a HCl salt (0.11 g) crystallizing from CHCl$_3$-ether-EtOAc, m.p. 144°–146° C. (Compound 156).

Alternate procedure for the preparation of (±)-exo-methyl-6-hydroxy-2-azabicyclo[2.2.2]octane-2-carboxylate (±)-exo-methyl-2-azabicyclo[2.2.2]oct-5-en-7-one-2-carboxylate Postassium hydroxide (39.9 g/712 mmol) was added to a solution of methyl 7-acetoxy-7-cyano-2-azabicyclo[2.2.2]

oct-5-ene-2-carboxylate (*J. Org. Chem.* 1989, 54, 2893) (35.6 g/142 mmol), ethanol (450 mL), and water (90 mL). Stirred at room temperature for 2 hours. Removed the ethanol by evaporation then extracted the aqueous residue with ethyl acetate. The organic extracts were dried over magnesium sulfate then evaporated. Purified by preprative HPLC over silica gel eluting with 10 to 100% ethyl acetate in hexanes to yield (±)-exo-methyl 2-azabicyclo[2.2.2]oct-5-en-7-one-2-carboxylate (9.2 g/50.8 mmol).

(±)-exo-Methyl-2-azabicyclo[2.2.2]oct-6-one-2-carboxylate

A sample of (±)-exo-Methyl 2-azabicyclo[2.2.2]oct-5-en-7-one-2-carboxylate (9.2 g/50.8 mmol) was hydrogenated with 5% palladium on carbon (0.5 g) in methanol (150 mL) at 35 PSIG and room temperature for 1 hour. Filtered off the catalyst and evaporated the filtrate to yield (±)-exo-methyl-2-azabicyclo[2.2.2]oct-6-one-2-carboxylate (9 g).

(±)-exo-Methyl-6-hydroxy-2-azabicyclo[2.2.2]octane-2-carboxylate

Sodium borohydride (1.4 g/36.1 mmol) was added to a mixture of (±)-exo-methyl-2-azabicyclo[2.2.2]oct-6-one-2-carboxylate (6 g/32.8 mmol) and cerium trichloride heptahydrate (13.4 g/36.1 mmol) in methanol (55 mL) at 0° C. Stirred at room temperature overnight. The reaction was evaporated, the residue was taken up in water then extracted with ethyl acetate. The organic extracts were dried over magnesium sulfate then evaporated. The residue was purified by flash chromatography over silica gel eluting with 25% ethyl acetate in hexanes to yield (±)-exo-methyl-6-hydroxy-2-azabicyclo[2.2.2]octane-2-carboxylate (3.6 g/19.5 mmol).

(±)-endo-Methyl-6-hydroxy-2-azabicyclo[2.2.2]octane-2-carboxylate

Separation of (±)-exo-methyl-6-hydroxy-2-azabicyclo[2.2.2]octane-2-carboxylate and (±)-endo-methyl-6-hydroxy-2-azabicyclo[2.2.2]octane-2-carboxylate, Compound 62, was achieved by hplc over silica gel eluting with a 10% to 80% EtOAc-hexane gradient.

EXAMPLE 154

(±)-exo-3-Propythio-4-(2-methoxycarbonyl-2-azabicyclo[2.2.2]octyl-6-oxy)-1,2,5-thiadiazole Sodium hydride (19.5 mmol) was added to a solution of (±)-exo-methyl-6-hydroxy-2-azabicyclo[2.2.2]octane-2-carboxylate (3.6 g/19.5 mmol) in tetrahydrofuran (200 mL) at room temperature. The reaction was stirred for 1 hour whereupon 3-chloro-4-propylthio-1,2,5-thiadiazole (3.8 g/19.5 mmol) in tetrahydrofuran (50 mL) was added to the reaction and stirred for 16 hours at room temperature. The reaction was poured into water and extracted with ethyl acetate. The organic extracts were dried over magnesium sulfate then evaporated. The residue was purified by preprative HPLC over silica gel eluting with 5 to 50% ethyl acetate in hexanes to yield [exo] (±)-exo-3-Propythio-4-(2-methoxycarbonyl-2-azabicyclo[2.2.2]octyl-6-oxy)-1,2,5-thiadiazole (2.1 g/6.1 mmol). (Compound 157).

EXAMPLE 155

(±)-exo-3-Propylsulfonyl-4-(2-methoxycarbonyl-2-azabicyclo[2.2.2]octyl-6-oxy)-1,2,5-thiadiazole A solution of Oxone® (7.6 g/12.4 mmol) in water (30 mL) was added to a solution of (±)-exo-3-propythio-4-(2-methoxycarbonyl-2-azabicyclo[2.2.2]octyl-6-oxy)-1,2,5-thiadiazole (2.1 g/6.1 mmol), water (10 mL), and tetrahydrofuran (20 mL). Stirred at room temperature for 16 hours. The reaction was extracted with diethyl ether (3×50 mL). The organic extracts were washed with water, saturated aqueous sodium bicarbonate, water, dried over magnesium sulfate, then evaporated to yield (±)-exo-3-propylsulfonyl-4-(2-methoxycarbonyl-2-azabicyclo[2.2.2]octyl-6-oxy)-1,2,5-thiadiazole (2.4 g). (Compound 158).

EXAMPLE 156

(±)-exo-3-(4,4,4-Trifluorobutyloxy)-4-(2-methoxycarbonyl-2-azabicyclo[2.2.2]octyl-6-oxy)-1,2,5-thiadiazole Sodium hydride (4.1 mmol) was added to a solution of 4,4,4-trifluorobutanol in tetrahydrofuran (35 mL) at room temperature. Stirred for 2 hours where upon (±)-exo-3-propylsulfonyl-4-(2-methoxycarbonyl-2-azabicyclo[2.2.2]octyl-6-oxy)-1,2,5-thiadiazole (1.0 g/2.7 mmol) in tetrahydrofuran (5 mL) was added to the reaction. The reaction was refluxed for 16 hours. The reaction was poured into brine then extracted with ethyl acetate (3×75 mL). The organic extracts were dried over magnesium sulfate to yield (±)-exo-3-(4,4,4-trifluorobutyloxy)-4-(2-methoxycarbonyl-2-azabicyclo[2.2.2]octyl-6-oxy)-1,2,5-thiadiazole (1.0 g/2.5 mmol). (Compound 159).

EXAMPLE 157

(±)-exo-3-(4,4,4-Trifluorobutyloxy)-4-(2-azabicyclo[2.2.2]octyl-6-oxy)-1,2,5-thiadiazole Trimethylsilyl iodide (0.4 mL/3.0 mmol) was added to a solution of (±)-exo-3-(4,4,4-trifluorobutyloxy)-4-(2-methoxycarbonyl-2-azabicyclo[2.2.2]octyl-6-oxy)-1,2,5-thiadiazole (1.0 g/2.5 mmol) and dichloromethane (30 mL). The reaction was refluxed for 16 hours then poured into methanol (25 mL), stirred at room temperature for 15 minutes, then evaporated. The residue was purified by radial chromatography on silica gel eluting with 2% ethanol/10% triethylamine in ethyl acetate to yield (±)-exo-3-(4,4,4-trifluorobutyloxy)-4-(2-azabicyclo[2.2.2]octyl-6-oxy)-1,2,5-thiadiazole which was isolated as the oxalate salt to yield 251 mg (mp=115°–120° C.). (Compound 160).

EXAMPLE 158

(±)-exo-3-(Hexyloxy)-4-(2-azabicyclo[2.2.2]octyl-6-oxy)-1,2,5-thiadiazole

Substantially the same procedure used to prepare Compound 160 with substitution of hexanol for 4,4,4-trifluorobutanol gave (±)-exo-3-(hexyloxy)-4-(2-azabicyclo[2.2.2]octyl-6-oxy)-1,2,5-thiadiazole oxalate (mp=128°–30° C.). (Compound 161).

EXAMPLE 159

(±)-endo-3-(4,4,4-Trifluorobutyloxy)-4-(2-azabicyclo[2.2.2]octyl-6-oxy)-1,2,5-thiadiazole From (±)-endo-methyl-6-hydroxy-2-azabicyclo[2.2.2]octane-2-carboxylate was obtained (±)-endo-3-(4,4,4-trifluorobutyloxy)-4-(2-azabicyclo[2.2.2]octyl-6-oxy)-1,2,5-thiadiazole using substantially the same procedure used to synthesize Compound 160. The compound was isolated as the oxalate salt (mp=151°–153° C.). (Compound 162).

EXAMPLE 160

(±)-exo-3-(2-[Fluorophenoxy]ethylthio)-4-(2-methoxycarbonyl-2-azabicyclo[2.2.2]octyl-6-oxy)-1,2,5-thiadiazole Sodium sulfide nonahydrate (1 g/4.1 mmol) was added to (±)-exo-3-propylsulfonyl-4-(2-methoxycarbonyl-2- azabicyclo[2.2.2]octyl-6-oxy)-1,2,5-thiadiazole (1.3 g/3.5 mmol) in dimethylformamide (25 mL) at 100° C. Stirred for 2 hours whereupon 2-bromoethyl 4-fluorophenyl ether (0.9 g/4.2 mmol) in dimethylformamide (5 mL) was added to the reaction. Stirred for 1 hour at 100° C. then 16 hours at room temperature. The reaction was poured into brine then extracted with ethyl acetate (3×150 mL). The organic extracts were combined and dried over magnesium sulfate then evaporated. The residue was purified by radial chromatography over silica gel eluting with 30% ethyl acetate in hexanes to yield (i)-exo-3-(2-[fluorophenoxy]ethylthio)-4-(2-methoxycarbonyl-2-azabicyclo[2.2.2]octyl-6-oxy)-1,2,5-thiadiazole (0.9 g/2.1 mmol). (Compound 163).

EXAMPLE 161

(±)-exo-3-(2-[Fluorophenoxy]ethylthio)-4-(2-azabicyclo[2.2.2]octyl-6-oxy)-1,2,5-thiadiazole Trimethylsilyl iodide (0.4 mL/2.5 mmol) was added to a solution of (±)-exo-3-(2-[fluorophenoxy]ethylthio)-4-(2-methoxycarbonyl-2-azabicyclo[2.2.2]octyl-6-oxy)-1,2,5-thiadiazole (0.9 g/2.1 mmol) and dichloromethane (50 mL). The reaction was refluxed for 16 hours then poured into methanol (25 mL), stirred at room temperature for 15 minutes, then evaporated. The residue was purified by radial chromatography on silica gel eluting with 2% ethanol/10% triethylamine in ethyl acetate to yield (±)-exo-3-(2-[fluorophenoxy]ethylthio)-4-(2-azabicyclo[2.2.2]octyl-6-oxy)-1,2,5-thiadiazole which was isolated as the oxalate salt to yield 222 mg (mp=145°–149° C.). (Compound 164).

EXAMPLE 162

(±)-endo-3-Propylthio-4-(1-azabicyclo[3.2.1]octyl-6-oxy)-1,2,5-thiadiazole

A sample of (±)-endo-1-Azabicyclo[3.2.1]octan-6-ol (5.1 g, 40 mmoles) was added to a solution of potassium t-butoxide (5.4 g, 48 mmoles) in 120 ml THF and cooled in an ice bath. Compound 37 (8.0 g, 41 mmoles was added and the reaction stirred for 3 hr at room temperature. Ethyl acetate was added, the organic layer washed with water, dried over sodium sulfate and condensed to yield 10.0 g of crude product. HPLC purification eluting with 5% ethanol/chloroform with 0.5% ammonium hydroxide yielded 8 g of (±)-endo-3-propylthio-4-(1-azabicyclo[3.2.1]octyl-6-oxy)-1,2,5-thiadiazole as an oil, 71%. (Compound 165).

EXAMPLE 164

(±)-endo-3-Pronylsulfonyl-4-(1-azabicyclo[3.2.1]octyl-6-oxy)-1,2,5-thiadiazole

A solution of (±)-endo-3-propylthio-4-(1-azabicyclo[3.2.1]octyl-6-oxy)-1,2,5-thiadiazole (5.7 g) in 1N HCl (24 mL) was cooled in ice-water and Oxone (36.8 g) in $H_2O$ (75 mL) was added dropwise over 5 min. Cooling was removed and after 5 h, excess oxidant was destroyed with $NaHSO_3$. The reaction was poured into ice and the pH adjusted to 12. The mixture was extracted with EtOAc, the extracts washed with water, the solvent dried, and the solvent evaporated to give analytically pure (±)-endo-3-propylsulfonyl-4-(1-azabicyclo[3.2.1]octyl-6-oxy)-1,2,5-thiadiazole as an oil (4.6 g). (Compound 166).

EXAMPLE 164

(±)-endo-3-(4,4,4-Trifluorobutoxy)-4-(1-azabicyclo[3.2.1]octyl-6-oxy)-1,2,5-thiadiazole A solution of 4,4,4-trifluorobutanol (0.32 g) in THF (15 mL) was cooled in ice-water and treated with potassium tert-butoxide (0.4 g). A solution of Compound 166 (0.4 g) in THF (10 mL) was added dropwise to the reaction and the mixture stirred 1 h. The reaction was diluted with cold water, the pH adjusted to 12, and the mixture extracted with EtOAc. The extracts were dried and the solvent evaporated. The residue was treated with dry HCl in ether and the resulting crystals collected, washed with ether, and dried to give a white solid (0.16 g), m.p. 155°–156° C. (Compound 167).

The following compounds were obtained by substantially the same procedure substituting the appropriate alcohol for the 4,4,4-trifluorobutanol.

EXAMPLE 165

(±)-endo-3-(2-Butynyloxy)-4-(1-azabicyclo[3.2.1]octyl-6-oxy)-1,2 5-thiadiazole

Obtained from Compound 166 and 2-butynol as the HCl salt in 89% yield, m.p. 200–201. (Compound 168).

EXAMPLE 166

(±)-endo-3-(trans-2-Butenyloxy)-4-(1-azabicyclo[3.2.1]octyl-6-oxy)-1,2,5-thiadiazole Obtained from Compound 166 and trans-2-butenol as the HCl salt in 54% yield, m.p. 160°–161° C. (Compound 169).

EXAMPLE 167

(±)-endo-3-(2-Methylthioethoxy)-4-(1-azabicyclo[3.2.1]octyl-6-oxy)-1,2,5-thiadiazole Obtained from Compound 166 and 2-methylthioethanol as the HCl salt in 85% yield, m.p. 169°–170° C. (Compound 170).

EXAMPLE 168

(±)-endo-3-(2-(4-Methyl-1,3-thiazol-5-yl)ethoxy)-4-(1-azabicyclo[3.2.1]octyl-6-oxy)-1,2,5-thiadiazole Obtained from Compound 166 and 2-(4-methyl-1,3-thiazol-5-yl)ethanol as the HCl salt in 73% yield, m.p. 171°–172° C. (Compound 171).

EXAMPLE 169

(±) -endo-3-(4-Methylthiobenzyloxy)-4-(1-azabicyclo[3.2.1]octyl-6-oxy)-1,2,5-thiadiazole Obtained from Compound 166 and 4-methylthiobenzyl alcohol as the HCl salt in 28% yield, m.p. 155°–156° C. (Compound 172).

EXAMPLE 170

(±)-endo-3-(2-Thienylmethoxy)-4-(1-azabicyclo[3.2.1]octyl-6-oxy)-1,2,5-thiadiazole Obtained from Compound 166 and 2-thiophenemethanol as the HCl salt in 29% yield, m.p. 134°–135° C. (Compound 173).

EXAMPLE 171

(±)-endo-3-(2-Cyclohexenyloxy)-4-(1-azabicyclo[3.2.1]octyl-6-oxy)-1,2,5-thiadiazole Obtained from Compound 166 and 2-cyclohexenol as the HCl salt in 55% yield, m.p. 179°–180° C. (Compound 174).

EXAMPLE 172

(±)-endo-3-(3-Pentynyloxy)-4-(1-azabicyclo[3.2.1]
octyl-6-oxy)-1,2,5-thiadiazole Obtained from Compound 166 and 3-pentynol as the HCl salt in 40% yield, m.p. 118°–119° C. (Compound 175).

EXAMPLE 173

(±)-endo-3-(3-Hexynyloxy)-4-(1-azabicyclo[3.2.1]
octyl-6-oxy)-1,2,5-thiadiazole

Obtained from Compound 166 and 3-hexynol as the HCl salt in 27% yield, m.p. 134°–135° C. (Compound 176).

EXAMPLE 174

(±)-endo-3-(3-Chloropropoxy)-4-(1-azabicyclo
[3.2.1]octyl-6-oxy)-1,2,5-thiadiazole Obtained from Compound 166 and 3-chloropropanol as the HCl salt in 48% yield, m.p. 131°–132° C. (Compound 177).

EXAMPLE 175

(±)-endo-3-[2-(2-Napthalyl)ethoxy]-4-(1-azabicyclo
[3.2.1]octyl-6-oxy)-1,2,5-thiadiazole Obtained from Compound 166 and 2-(2-napthalyl)ethanol as the HCl salt in 34% yield, m.p. 134°–139° C. (Compound 178).

EXAMPLE 176

(±)-endo-3-(4-Methyl-3-pentenyloxy)-4-(1-
azabicyclo[3,2,1]octyl-6-oxy)-1,2,5-thiadiazole Obtained from Compound 166 and 4-methyl-3-pentenol as the HCl salt in 98% yield, m.p. 113°–114° C. (Compound 180).

EXAMPLE 177

(±)-endo-3-(cis-2-Butenyloxy)-4-(1-azabicyclo
[3.2.1]octyl-6-oxy)-1,2,5-thiadiazole Obtained from Compound 166 and cis-2-butenol as the HCl salt in 37% yield, m.p. 151°–152° C. (Compound 181).

EXAMPLE 178

(±)-endo-3-(Cyclopropylmethoxy)-4-(1-azabicyclo
[3.2.1]octyl-6-oxy)-1,2,5-thiadiazole Obtained from Compound 166 and cyclopropylmethanol as the HCl salt in 50% yield, m.p. 165°–166° C. (Compound 182).

EXAMPLE 179

(±)-endo-3-(2-Methoxyethoxy)-4-(1-azabicyclo
[3.2.1]octyl-6-oxy)-1,2,5-thiadiazole Obtained from Compound 166 and 2-methoxyethanol as the HCl salt in 25% yield, m.p. 123°–124° C. (Compound 183).

EXAMPLE 180

(±)-endo-3-(3-Butenyloxy)-4-(1-azabicyclo[3.2.1]
octyl-6-oxy)-1,2,5-thiadiazole

Obtained from Compound 166 and 3-butenol as the HCl salt in 20% yield, m.p. 168°–169° C. (Compound 184).

EXAMPLE 181

(±)-endo-3-(2-Cyclopropylethoxy)-4-(1-azabicyclo
[3.2.1]octyl-6-oxy)-1,2,5-thiadiazole Obtained from Compound 166 and 2-cyclopropylethanol as the HCl salt in 76% yield, m.p. 152°–153° C. (Compound 185).

EXAMPLE 182

(±)-endo-3-(3-Butynyloxy)-4-(1-azabicyclo[3.2.1]
octyl-6-oxy)-1,2,5-thiadiazole

Obtained from Compound 166 and 3-butynol as the HCl salt in 65% yield, m.p. 198°–199° C. (Compound 186).

EXAMPLE 183

(±)-endo-3-(4,4,4,3,3,2,2-Heptafluorobutoxy)-4-(1-
azabicyclo[3.2.1]octyl-6-oxy)-1,2 5-thiadiazole Obtained from Compound 166 and 4,4,4,3,3,2,2-heptafluorobutanol as the HCl salt in 23% yield, m.p. 192°–193° C. (Compound 187).

EXAMPLE 184

(±)-endo-3-[2-(3-Trifluoromethylphenyl)ethoxy]-4-
(1-azabicyclo[3.2.1]octyl-6-oxy)-1,2,5-thiadiazole Obtained from Compound 166 and 2-(3-trifluoromethylphenyl)ethanol as the HCl salt in 38% yield, m.p. 118°–120° C. (Compound 188).

EXAMPLE 185

(±)-endo-3-[2-(2-Thienyl)ethoxy]-4-(1-azabicyclo
[3.2.1]octyl-6-oxy)-1,2,5-thiadiazole Obtained from Compound 166 and 2-(2-thienyl)ethanol as the HCl salt in 63% yield, m.p. 119°–120° C. (Compound 189).

EXAMPLE 186

(±)-endo-3-(3,3,3,2,2,Pentafluoropropoxy)-4-(1-
azabicyclo[3.2.1]octyl-6-oxy)-1,2 5-thiadiazole Obtained from Compound 166 and 3,3,3,2,2-pentafluoropropanol as the HCl salt in 77% yield, m.p. 208°–209° C. (Compound 190).

EXAMPLE 187

(±)-endo-3-(2-Phenoxyethoxy)-4-(1-azabicyclo
[3.2.1]octyl-6-oxy)-1,2,5-thiadiazole Obtained from Compound 166 and 2-phenoxyethanol as the HCl salt in 80% yield, m.p. 165°–166° C. (Compound 191).

EXAMPLE 188

(±)-endo-3-(4-n-Butylbenzyloxy)-4-(1-azabicyclo
[3.2.1]octyl-6-oxy)-1,2,5-thiadiazole Obtained from Compound 166 and 4-n-butylbenzyl alcohol as the HCl salt in 18% yield, m.p. 168°–169° C. (Compound 192).

EXAMPLE 189

(±)-endo-3-[3-(4-Methoxyphenyl)propoxy]-4-(1-
azabicyclo[3.2.1]octyl-6-oxy)-1,2,5-thiadiazole Obtained from Compound 166 and 3-(4-methoxyphenyl)propanol as the HCl salt in 54% yield, m.p. 161°–162° C. (Compound 193).

EXAMPLE 190

(±)-endo-3-(4-Fluorobenzyloxy)-4-(1-azabicyclo [3.2.1]octyl-6-oxy)-1,2,5-thiadiazole Obtained from Compound 166 and 4-fluorobenzyl alcohol as the HCl salt in 71% yield, m.p. 163°–164° C. (Compound 194).

EXAMPLE 191

(±)-endo-3-(2,4-Difluorobenzyloxy)-4-(1-azabicyclo [3.2.1]octyl-6-oxy)-1,2,5-thiadiazole Obtained from Compound 166 and 2,4-difluorobenzyl alcohol as the HCl salt in 17% yield, m.p. 168°–169° C. (Compound 195).

EXAMPLE 192

(±)-endo-3-[4-(Trifluoromethoxy)benzyloxy]-4-(1-azabicyclo[3.2.1]octyl-6-oxy)-1,2,5-thiadiazole Obtained from Compound 166 and 4-trifluoromethoxybenzyl alcohol as the HCl salt in 8% yield, m.p. 185°–186° C. (Compound 196).

EXAMPLE 193

(±)-endo-3-(4-Fluorobutoxy)-4-(1-azabicyclo[3.2.1] octyl-6-oxy)-1,2,5-thiadiazole Obtained from Compound 166 and 4-fluorobutanol as the HCl salt in 56% yield, m.p. 142°–143° C. (Compound 197).

EXAMPLE 194

(±)-endo-3-(4-tert-Butylbenzyloxy)-4-(1-azabicyclo [3.2.1]octyl-6-oxy)-1,2,5-thiadiazole Obtained from Compound 166 and 4-tert-butylbenzyl alcohol as the HCl salt in 40% yield, m.p. 192°–194° C. (Compound 198).

EXAMPLE 195

(±)-endo-3-(1-Cyclopropylethoxy)-4-(1-azabicyclo [3.2.1]octyl-6-oxy)-1,2,5-thiadiazole Obtained from Compound 166 and (±)-1-cyclopropylethanol as the HCl salt in 39% yield, m.p. 171°–172° C. (Compound 199).

EXAMPLE 196

(±)-endo-3-(2-Cyclohexylethoxy)-4-(1-azabicyclo [3.2.1]octyl-6-oxy)-1,2,5-thiadiazole Obtained from Compound 166 and 2-cyclohexylethanol as the HCl salt in 15% yield, m.p. 139°–141° C. (Compound 200).

EXAMPLE 197

(±)-endo-3-(3-Methyl-2-butenyloxy)-4-(1-azabicyclo [3.2.1]octyl-6-oxy)-1,2,5-thiadiazole Obtained from Compound 166 and 3-methyl-2-butenol as the HCl salt in 60% yield, m.p. 149°–150° C. (Compound 201).

EXAMPLE 198

(±)-endo-3-(4-Cyclohexylbutoxy)-4-(1-azabicyclo [3.2.1]octyl-6-oxy)-1,2,5-thiadiazole Obtained from Compound 166 and 4-cyclohexylbutanol in as the HCl salt 9% yield, m.p. 130°–132° C. (Compound 202).

EXAMPLE 199

(±)-endo-3-(3-Butyn-2-oxy)-4-(1-azabicyclo[3.2.1] octyl-6-oxy)-1,2,5-thiadiazole Obtained from Compound 166 and (±)-3-butyn-2-ol in 58% yield as the HCl salt, m.p. 179°–180° C. (Compound 203).

EXAMPLE 200

(±)-endo-3-(3-Methyl-3-phenylbutoxy)-4-(1-azabicyclo[3.2.1]octyl-6-oxy)-1,2,5-thiadiazole Obtained from Compound 166 and 3-methyl-3-phenylbutanol as the HCl salt in 34% yield, m.p. 145°–147° C. (Compound 204).

EXAMPLE 201

(±)-endo-3-(3-Fluoropropoxy)-4-(1-azabicyclo [3.2.1]octyl-6-oxy)-1,2,5-thiadiazole Obtained from Compound 166 and 3-fluoropropanol as the HCl salt in 72% yield, m.p. 147°–148° C. (Compound 205).

EXAMPLE 202

(±)-endo-3-[3-(2-Thienyl)propoxy]-4-(1-azabicyclo [3.2.1]octyl-6-oxy)-1,2,5-thiadiazole Obtained from Compound 166 and 3-(2-thienyl)propanol in 75% yield, m.p. 140°–142° C. (Compound 206).

EXAMPLE 203

(±)-3-(2-[4-Fluorophenoxy]ethylthio)-4-(1-azabicyclo[2.2.2]octyl-3-oxy)-1,2,5-thiadiazole Using substantially the same procedure used for the preparation of compound 44, compound 12 (1.15 g) and 1-bromo-(4-fluorophenoxy)ethane (3.65 g) gave (±)-3-(2-[4-fluorophenoxy]ethylthio)-4-(1-azabicyclo[2.2.2]octyl-3-oxy)-1,2,5-thiadiazole as an HCl salt (1.55 g) crystallizing from ether-EtOAc-CHCl$_3$, m.p. 160°–161° C. (Compound 207).

EXAMPLE 204

(±)-3-(2-Methylthioethyl)-4-(1-azabicyclo[2.2.2] octyl-3-oxy)-1,2,5-thiadiazole

A solution of 3-(2-methylthioethyl)-4-hydroxy-1,2,5-thiadiazole (0.45 g) and triphenylphosphine (0.7 g) was cooled in ice-water as diethyldiazodicarboxylate (0.4 mL) was added dropwise. After addition, (±)-1-azabicyclo[2.2.2] octan-3-ol (0.33 g) was added, cooling removed, and reaction stirred for 1 hour. The solvent was evaporated, residue suspended in water, the mixture acidified and washed with ether. The aqueous solution was made basic and extracted with EtOAc. The extracts were dried, the solvent evaporated, the residue purified by radial chromatography eluting with 10%-EtOH-1%-NH$_4$OH—CHCl$_3$, and the product converted to a HCl salt. Recrystallization from acetone gave 0.6 g white crystals, m.p. 177°–178° C. (Compound 208).

The following compounds were synthesized in substantially the same manner as Compound 208.

EXAMPLE 205

(±)-3-(1-azabicyclo[2.2.2]octyl-3-oxy)-1,2,5-thiadiazole

A sample of 3-Hydroxy-1,2,5-thiadiazole (0.28 g), triphenylphospine (0.7 g), diethyldiazodicarboxylate (0.4 mL), and (±)-1-azabicyclo[2.2.2]octan-3-ol (0.33 g) gave the hydrochloride salt of (±)-3-(1-azabicyclo[2.2.2]octyl-3-oxy)-1,2,5-thiadiazole, m.p. 240° C. dec. (0.36 g). (Compound 209).

EXAMPLE 206

(±)-3-Hexyl-4-(1-azabicyclo[2.2.2]octyl-3-oxy)-1,2,5-thiadiazole

A sample of 3-Hexyl-4-Hydroxy-1,2,5-thiadiazole (0.93 g), triphenylphospine (1.31 g), diethyldiazodicarboxylate (0.8 mL), and (±)-1-azabicyclo[2.2.2]octan-3-ol (0.64 g) gave the hydrochloride salt of (±)-3-hexyl-4-(1-azabicyclo[2.2.2]octyl-3-oxy)-1,2,5-thiadiazole, m.p. 163°–164° C. dec. (1.11 g). (Compound 210).

EXAMPLE 207

3-Butylthio-4-hydroxy-1,2,5-thiadiazole

A solution of Compound 1 (20.9 g), DMSO (20 mL) and 2N NaOH (205 mL) was headed to reflux overnight. The solution was cooled to 15° C. and concentrated HCl was added until the pH was 1. The solid was collected, washed with water, and dried to give a solid (17.68 g). Recrystallization from heptane gave white crystals, m.p. 72°–72.5° C. (Compound 211).

EXAMPLE 208

(±)-3-(2-[3-{1,2,5-Thiadiazoyloxy}]ethoxy)-4-(1-azabicyclo[2.2.2]octyl-3-oxy)-1,2,5-thiadiazole A solution of triphenylphosphine (0.35 g) and 3-hydroxy-1,2,5-thiadiazole (0.14 g) in THF (15 mL) was cooled in ice-water. Diethyl diazodicarboxylate (0.21 g) was added dropwise followed by (±)-3-(2-hydroxyethoxy)-4-(1-azabicyclo[2.2.2]octyl-3-oxy)-1,2,5-thiadiazole (0.35 g). Cooling was removed, reaction was stirred 1 h, and the solvent was evaporated. The residue was suspended in cold water, acidified, and extracted with ether. The aqueous fraction was made basic and extracted with EtOAc. The extracts were washed with brine, dried, the solvent evaporated, and the residue purified by radial chromatography eluting with 10%-EtOH-1% NH$_4$OH—CHCl$_3$ to give a clear oil. The HCl salt crystallized from acetone as a white powder (0.34 g), m.p. 178°–179° C. (Compound 212).

EXAMPLE 209

(±)Exo-3-Butylthio-4-(1-azabicyclo[2.2.1]heptyl-3-oxy)-1,2,5-thiadiazole

A solution of triphenylphosphine (0.7 g) and 317260 (0.5 g) in THF (20 mL) was cooled in ice-water. Diethyl diazodicarboxylate (0.4 mL) was added dropwise followed by addition of (±)endo-3-hydroxy-1-azabicyclo[2.2.1]heptane (0.29 g). Cooling was removed and after 1 h the solvent was evaporated. The residue was suspended in cold water, acidified, and extracted with ether. The aqueous fraction was made basic and extracted with EtOAc. The extracts were dried, the solvent evaporated, and the residue purified by radial chromatography eluting with 5%-EtOH-0.5% NH$_4$OH—CHCl$_3$ to give a clear oil. The HCl salt crystallized from EtOAc as white crystals (0.44 g), m.p. 147°–148° C. (Compound 213).

EXAMPLE 210

(±)-endo-3-[2-(4-Chlorophenyl)ethoxy]-4-(1-azabicyclo[3.2.1]octyl-6-oxy)-1,2,5-thiadiazole Obtained from Compound 166 and 2-(4-chlorophenyl) ethanol in 50% yield, HCl salt m.p. 136°–138° C. (Compound 214).

EXAMPLE 211

(±)-endo-3-[2-(4-Fluorophenyl)ethoxy]-4-(1-azabicyclo[3.2.1]octyl-6-oxy)-1,2,5-thiadiazole Obtained from Compound 166 and 2-(4-fluorophenyl) ethanol in 61% yield, HCl salt m.p. 135°–136° C. (Compound 215).

EXAMPLE 212

(±)-endo-3-[2-(3-Methylphenyl)ethoxy]-4-(1-azabicyclo[3.2.1]octyl-6-oxy)-1,2,5-thiadiazole Obtained from Compound 166 and 2-(3-methylphenyl) ethanol in 57% yield, HCl salt m.p. 114°–115° C. (Compound 216).

EXAMPLE 213

(±)-endo-3-(2-Phenylethoxy)-4-(1-azabicyclo[3.2.1]octyl-6-oxy)-1,2,5-thiadiazole Obtained from Compound 166 and 2-phenylethanol in 70% yield, HCl salt m.p. 135°–136° C. (Compound 217).

EXAMPLE 214

(±)-endo-3-[2-(3-Thienyl)ethoxy]-4-(1-azabicyclo[3.2.1]octyl-6-oxy)-1,2,5-thiadiazole Obtained from Compound 166 and 2-(3-thienyl)ethanol in 62% yield, HCl salt m.p. 142°–144° C. (Compound 218).

EXAMPLE 215

(±)-endo-3-Benzyloxy-4-(1-azabicyclo[3.2.1]octyl-6-oxy)-1,2,5-thiadiazole

Obtained from Compound 166 and benzyl alcohol in 71% yield, HCl salt m.p. 180°–181° C. (Compound 219).

EXAMPLE 216

(±)-endo-3-(4-Trifluoromethylbenzyloxy)-4-(1-azabicyclo[3.2.1]octyl-6-oxy)-1,2,5-thiadiazole Obtained from Compound 166 and 4-trifluoromethylbenzyl alcohol in 76% yield, maleate salt m.p. 174°–175° C. (Compound 220).

EXAMPLE 217

(5S, 6S)-endo-3-(4-Fluorobenzyloxy)-4-(1-azabicyclo[3.2.1]octyl-6-oxy)-1,2,5-thiadiazole Obtained from (5S,6S)-Compound 166 and 4-fluorobenzyl alcohol in 33% yield, HCl salt m.p. 181°–182° C. (Compound 221).

EXAMPLE 218

(5R, 6R)-endo-3-(4-Fluorobenzyloxy)-4-(1-azabicyclo[3.2.1]octyl-6-oxy)-1,2,5-thiadiazole Obtained from (5R,6R)-Compound 166 and 4-fluorobenzyl alcohol in 68% yield, maleate salt m.p. 106°–107° C. (Compound 222).

EXAMPLE 219

(5S, 6S)-endo-3-(4-Trifluoromethoxybenzyloxy)-4-(1-azabicyclo[3.2.1]octyl-6-oxy)-1,2,5-thiadiazole Obtained from (5S,6S)-Compound 166 and 4-trifluoromethoxybenzyl alcohol in 52% yield, HCl salt m.p. 138°–140° C. (Compound 223).

EXAMPLE 220

(5R, 6R)-endo-3-(4-Trifluoromethoxybenzyloxy)-4-(1-azabicyclo[3.2.1]octyl-6-oxy)-1,2,5-thiadiazole Obtained from (5R,6R)-Compound 166 and 4-trifluoromethoxybenzyl alcohol in 71% yield, maleate salt m.p. 114°–115° C. (Compound 224).

EXAMPLE 221

(5R, 6R) -endo-3-(2-Cyclopropylethoxy)-4-(1-azabicyclo[3.2.1]octyl-6-oxy)-1,2,5-thiadiazole Obtained from (5R,6R)-Compound 166 and 2-cyclopropylethanol in 84% yield, maleate salt m.p. 111°–112° C. (Compound 225).

EXAMPLE 222

(5S, 6S) -endo-3-(2-Cyclopropylethoxy)-4-(1-azabicyclo[3.2.1]octyl-6-oxy)-1,2,5-thiadiazole Obtained from (5S,6S)-Compound 166 and 2-cyclopropylethanol in 78% yield, maleate salt m.p. 109°–110° C. (Compound 226).

EXAMPLE 223

(5R, 6R)-endo-3-(3-Methyl-2-butenyloxy)-4-(1-azabicyclo[3.2.1]octyl-6-oxy)-1,2,5-thiadiazole Obtained from (5R,6R)-Compound 166 and 3-methyl-2-butenol in 81% yield, maleate salt m.p. 141°–142 ° C. (Compound 227).

EXAMPLE 224

(±)-endo-3-(2-Cyclopropylideneethoxy)-4-(1-azabicyclo[3.2.1]octyl-6-oxy)-1,2,5-thiadiazole Obtained from Compound 166 and 2-cyclopropylideneethanol in 67% yield, maleate salt m.p. 100°–101° C. (Compound 228).

EXAMPLE 225

(±)-endo-3-(3-Cyclopropylpropoxy)-4-(1-azabicyclo[3.2.1]octyl-6-oxy)-1,2,5-thiadiazole Obtained from Compound 166 and 3-cyclopropylpropanol in 62% yield, maleate salt m.p. 114°–115° C. (Compound 229).

EXAMPLE 226

(±)-endo-3-(1-Cyclopropylethoxy)-4-(1-azabicyclo[3.2.1]octyl-6-oxy)-1,2,5-thiadiazole Obtained from Compound 166 and 1-cyclopropylethanol in 78% yield, maleate salt m.p. 161°–162° C. (Compound 230).

EXAMPLE 227

(±)exo-3-(1-Azabicyclo[2.2.1]heptyl-3-oxy)-1,2,5-thiadiazole

Prepared in the same manner as Compound 131. (±)Exo-3-(1-azabicyclo[2.2.1]heptyl-3-oxy)-1,2,5-thiadiazole was obtained from 3-hydroxy-1,2,5-thiadiazole (0.14 g), triphenylphosphine (0.35 g), diethyldiazodicarboxylate (0.21 mL) and (±)-endo-1-azabicyclo[2.2.1]heptane-3-ol (0.15 g) as a hydrochloride salt (0.096 g), m.p. 223° C., dec. (Compound 231).

EXAMPLE 228

(±)-3-(3-[3-Trifluoromethyl-4-chlorophenyl]propoxy)-4-(1-azabicyclo[2.2.2]octyl-3-oxy)-1,2,5-thiadiazole Using the same procedure used in the preparation of Compound 103, (3-trifluoromethyl-4-chlorophenyl)propanol and Compound 102 gave after chromatography (±)-3-(3-[3-trifluoromethyl-4-chlorophenyl]propoxy)-4-(1-azabicyclo[2.2.2]octyl-3-oxy)-1,2,5-thiadiazole as an HCl salt, m.p. 144°–146° C. (Compound 232).

EXAMPLE 229

(±)-3-(3-Phenylpropoxy)-4-(1-azabicyclo[2.2.2]octyl-3-oxy)-1,2,5-thiadiazole

Using the same procedure used in the preparation of Compound 103, 3-phenylpropanol and Compound 102 gave after chromatography (±)-3-(3-phenylpropoxy)-4-(1-azabicyclo[2.2.2]octyl-3-oxy)-1,2,5-thiadiazole as an HCl salt, m.p. 194°–196° C. (Compound 233).

EXAMPLE 230

(R)-3-(2-Cyclopropylethoxy)-4-(1-azabicyclo[2.2.2]octyl-3-oxy)-1,2,5-thiadiazole Using the same procedure used in the preparation Compound 114, 2-cyclopropylethanol and Compound 102 that had been prepared from (R)-1-azabicyclo[2.2.2]octan-3-ol gave after chromatography, (R)-3-(2-cyclopropylethoxy)-4-(1-azabicyclo[2.2.2]octyl-3-oxy)-1,2,5-thiadiazole as an HCl salt that crystallized from acetone, m.p. 189°–190° C. (Compound 234).

EXAMPLE 231

3-Ethoxy-4-hydroxy-1,2,5-thiadiazole

A mixture of Compound 93 (8.2 g), 2N NaOH (100 mL), and DMSO (10 mL) was heated to reflux over night. The reaction was cooled and extracted with ether. The aqueous fraction was acidified with conc. HCl and cooled 30 min in ice-water. The solid was collected from the resulting mixture by filtration and washed with a small amount of cold water to give white crystals (4.4 g). Recrystallization from heptane gave white flakes, m.p. 104.5°–105.5° C. (Compound 235).

EXAMPLE 232

3-Propylthio-4-hydroxy-1,2,5-thiadiazole

A mixture of 3-chloro-4-propylthio-1,2,5-thiadiazole (Compound 37) (10 g), 2N NaOH (100 mL), and DMSO (10 mL) was heated to reflux for 24 h. The solution was cooled and extracted with ether. The aqueous fraction was acidified with conc. HCl and cooled in ice-water for 3 h. The resulting solid was collected, washed with a small amount of cold water to give a white solid (8.15 g). Recrystallization from heptane gave white crystals, m.p. 84°–85° C. (Compound 236).

We claim:

1. A process for preparing a compound of formula II:

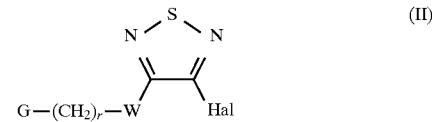

wherein Hal is Cl, Br, or $R^9SO_2$;

$R^9$ is straight or branched chain alkyl or aryl;

W is oxygen or sulphur;

G is selected from one of the following azacyclic or azabicyclic ring systems:

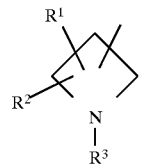 het-1

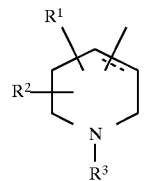 het-2

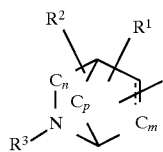 het-3

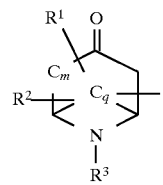 het-4

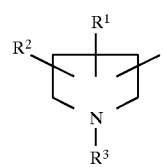 het-5

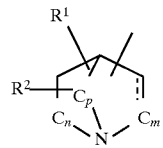 het-6

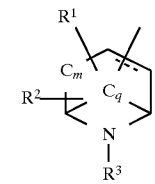 het-7 or G is optionally substituted $C_3$–$C_8$ cycloalkyl or $C_{1-6}$-alkyl wherein the substitution is —$NR^6R^7$;

$R^6$ and $R^7$ independently are hydrogen or $C_{1-6}$-alkyl, or $R^6$ and $R^7$ together form a $C_3$–$C_5$-alkylene group which together with the nitrogen atom form a 4- to 6-membered group;

$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with —OH, —$COR^{6'}$, $CH_2$—OH, halogen, —$NH_2$, carboxy, or phenyl;

$R^3$ is hydrogen, $C_{1-5}$-alkyl, $C_{2-5}$-alkenyl or $C_{2-5}$-alkynyl;

$R^{6'}$ is hydrogen or $C_{1-6}$-alkyl;

m, n, p, and r are independently 0, 1 or 2;

q is 1 or 2; and

═══════ is a single or double bond;

provided that: 1) when W is oxygen, G cannot be alkyl; and 2) one of m, n, or p must be other than 0; comprising a) reacting $(CN)_2$ with a compound of the formula $G(CH_2)_r$—W—H; and b) reacting with the product of step (a) with $S_2Hal_2$.

2. A process for preparing a compound of formula III:

 (III)

wherein Hal is Cl, Br or $R^9SO_2$;

$R^9$ is straight or branched chain alkyl or aryl;

$R^1$ is —$SR^4$, —$OR^5Y$, —$SR^5Y$, $OR^5$—Z—Y, —$SR^5ZY$, —O—$R^5$—Z—$R^4$ or —S—$R^5$—Z—$R^4$;

$R^4$ is $C_{1-15}$-alkyl, $C_{2-15}$-alkenyl, or $C_{2-15}$-alkynyl, each of which is optionally substituted with one or more halogen(s), —$CF_3$, —CN, Y, phenyl or phenoxy wherein phenyl or phenoxy is optionally substituted with halogen, —CN, $C_{1-4}$-alkyl, $C_{1-4}$-alkoxy, —$OCF_3$, —$CF_3$, —$CONH_2$ or —$CSNH_2$;

Z is oxygen or sulphur;

$R^5$ is $C_{1-15}$-alkylene, $C_{2-15}$-alkenylene, or $C_{2-15}$-alkynylene;

and Y is a 5 or 6 membered heterocyclic group; comprising a) reacting $(CN)_2$ with a compound selected from $R^4$—S—H, $YR^5VH$, Y—Z—$R^5VH$ or $R^4$—Z—$R^5$—VH; wherein V is O or S; and b) reacting the product of step (a) with $S_2Hal_2$.

* * * * *